United States Patent [19]

Rogers et al.

[11] Patent Number: 5,041,567

[45] Date of Patent: Aug. 20, 1991

[54] ANTIBACTERIAL MONIC ACID DERIVATIVES

[75] Inventors: Norman H. Rogers, Horsham; Peter J. O'Hanlon, Redhill; Graham Walker, Guildford; Michael J. Crimmin, Horsham, all of England

[73] Assignee: Beecham Group plc, England

[21] Appl. No.: 276,910

[22] Filed: Nov. 28, 1988

Related U.S. Application Data

[62] Division of Ser. No. 469,819, Feb. 25, 1983, Pat. No. 4,812,470.

[30] Foreign Application Priority Data

Feb. 27, 1982 [GB] United Kingdom ............... 8205842
Oct. 28, 1982 [GB] United Kingdom ............... 8230800

[51] Int. Cl.$^5$ .................. C07D 404/06; C07D 299/22
[52] U.S. Cl. ...................................... 549/414; 549/416; 549/419; 548/203; 548/206; 548/214; 548/255; 548/247
[58] Field of Search ................ 549/414, 416; 514/460

[56] References Cited

U.S. PATENT DOCUMENTS 4,200,635  4/1980  Rogers ............................... 549/414
4,812,470  3/1989  Rogers et al. ...................... 514/365

OTHER PUBLICATIONS

CA 113(5):40243q, The Chemistry of Pseudomonic aud. Part II, J. Chem. Soc. Perkintrans, 1, (11), 2059–63.
CA 100(15): 120778q, Antibacterial 1-norman-2-yl hetcidcyclo Compounds, Roger et al. EP 87953A2 Sep. 7, 1983.

Primary Examiner—Mukund J. Shah
Assistant Examiner—Jyothsna Denkat
Attorney, Agent, or Firm—Rosenman & Colin

[57] ABSTRACT

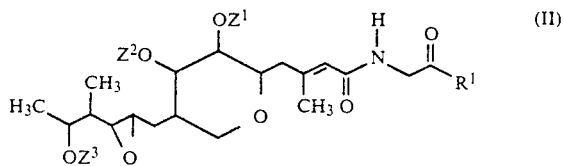

wherein $R^1$ is unsubstituted or substituted phenyl, have been prepared which have antibacterial and/or antimycoplasmal activity.

10 Claims, No Drawings

ANTIBACTERIAL MONIC ACID DERIVATIVES

CROSS-REFERENCE

This is a division of Ser. No. 469,819 now U.S. Pat. No. 4,812,470 filed Feb. 25, 1983.

The present invention relates to a class of compounds having antibacterial and/or antimycoplasmal activity, to processes for their production and to their use in human and veterinary medicine.

Accordingly, the present invention provides a compound of formula (I):

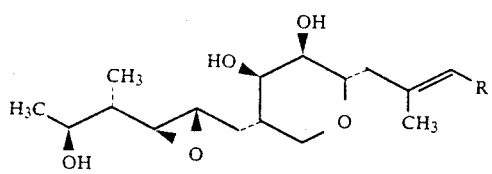

wherein
R is a group

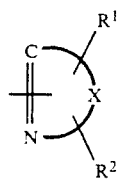

R¹ and R² are the same or different and each is selected from hydrogen; phenyl, $C_{1-20}$ alkyl, $C_{2-8}$ alkenyl, $C_{2-8}$ alkynyl or heterocyclyl each of which may optionally be substituted and $C_{3-7}$ cycloalkyl, X is a divalent group —Y—C=C—, and
Y is oxygen or sulphur.

Suitable heterocyclyl groups have 5 or 6-membered heterocyclic rings containing from 1 to 3 heteroatoms selected from oxygen, nitrogen and sulphur, for instance thienyl.

Suitable substitutents for a phenyl or heterocyclyl group include halogen, $C_{1-6}$ alkyl, $C_{1-6}$ alkoxy, hydroxy, carboxy, $C_{1-6}$ alkoxycarbonyl, carbamoyl, mono- or di-$(C_{1-6})$ alkyl carbamoyl, sulphamoyl, mono- and di-$(C_{1-6})$ alkyl sulphamoyl, cyano, nitro, amino, mono- and di-$(C_{1-6})$alkylamino, $C_{1-6}$ acylamino, ureido, $C_{1-6}$ alkoxycarbonylamino, 2,2,2-trichloroethoxy-carbonylamino, $C_{1-6}$ alkanoyl, $C_{1-6}$ alkylthio, $C_{1-6}$ alkanesulphinyl, and $C_{1-6}$ alkanesulphonyl.

Suitable substituents for alkyl, alkenyl and alkynyl groups include halogen, carboxy, $C_{1-6}$ alkoxycarbonyl, carbamoyl, mono- or di-$(C_{1-6})$alkyl carbamoyl, sulphamoyl, mono- and di-$(C_{1-6})$alkylsulphamoyl, amino, mono- and di-$(C_{1-6})$alkylamino, $C_{1-6}$ acylamino, ureido, $C_{1-6}$ alkoxycarbonylamino, 2,2,2-trichloroethoxy carbonylamino, aryl, heterocyclyl, hydroxy, $C_{1-6}$ alkoxy, oxo, aroyl, 2-thenoyl, $C_{1-6}$ alkylthio, $C_{1-6}$ alkanesulphinyl, $C_{1-6}$ alkanesulphonyl, hydroxyimino, hydrazono, benzohydroximoyl, 2-thiophenecarbohydroximoyl.

Compounds of formula (I) have a tri-substituted double bond and this may be in either the E or Z configuration giving rise to two geometrically isomeric forms. The present invention encompasses both such isomers individually and admixed in any proportions. In general, greater biological activity is associated with the E isomer and for this reason the E isomer is preferred.

Compounds of formula (I) having the E configuration have been named "1-normon-2-yl-heterocycles". The absolute stereochemistry of the 1-normon-2-yl radical is as shown in formula (I).

It will be appreciated that R, i.e. the group

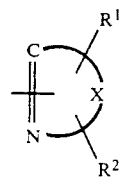

represents the residues of four related heterocyclic systems, viz:

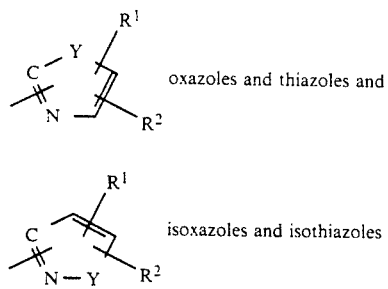

oxazoles and thiazoles and isoxazoles and isothiazoles

All these are encompassed by the invention.
Preferably R is a group

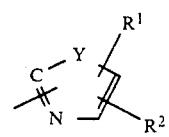

Preferably Y is oxygen.
Preferably R¹ and R² are different and more preferably R² is hydrogen.

Most preferably R is substituted or unsubstituted oxazolyl.

The 1-normon-2-yl moiety may be bonded to any carbon atom of R, but preferably it is bonded to a carbon atom adjacent the nitrogen atom.

Most preferably the group R is substituted or unsubstituted 2-oxazolyl.

Preferably R¹ is bonded to a carbon atom adjacent to the atom Y.

Most preferably the compound of formula (I) is a compound of formula (IA):

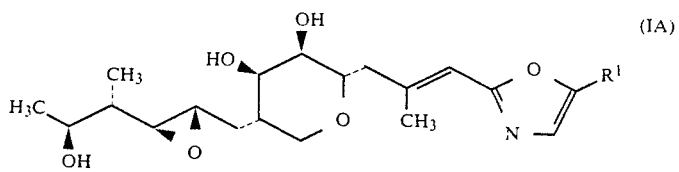
(IA)

wherein R¹ is as defined above.

The present invention also provides a process for producing a compound of formula (IA) which process comprises cyclising a compound of formula (II):

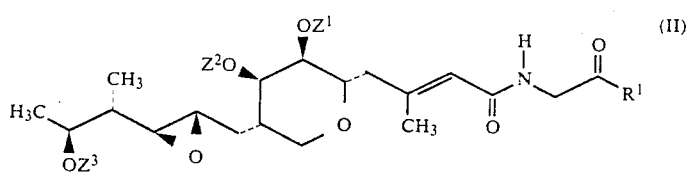
(II)

wherein
R¹ is as defined in relation to formula (I); and
$Z^1$, $Z^2$ and $Z^3$ are the same or different and each is hydrogen or a hydroxyl-protecting group to form a compound of formula (IA) and, where necessary, removing any hydroxyl-protecting groups, and, if desired, converting one compound of formula (IA) into a further compound of formula (IA).

The present invention also provides a process for producing a compound of formula (I) which process comprises reacting a compound of formula (III):

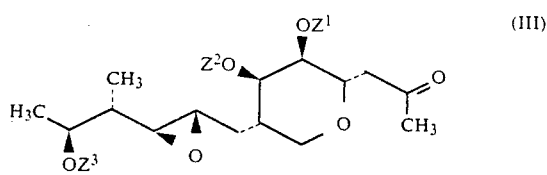
(III)

wherein
$Z^1$, $Z^2$ and $Z^3$ are the same or different and each is hydrogen or a hydroxyl-protecting group,
with a compound of formula (IV):

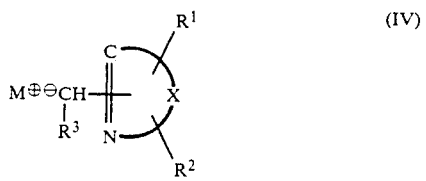
(IV)

wherein
R¹ and R² are as defined in relation to formula (I)
M⁺ is a metal cation, preferably an alkali metal cation, most preferably a lithium or sodium cation, and
R³ is an anion-stabilising group which will spontaneously eliminate with a β-hydroxyl group to produce an olefin, preferably a trialkylsilyl or a dialkylphosphonate group, most preferably trimethylsilyl or diethylphosphonate,
and, where necessary, removing any hydroxyl-protecting groups, and, if desired, converting one compound of formula (I) into a further compound of formula (I).

The cyclisation of a compound of formula (II) is suitably effected using a chlorinating agent such as phosphorus oxychloride, phosgene, thionyl chloride or phosphorus pentachloride in the presence of a tertiary amine, such as triethylamine or pyridine. Such reactions are conveniently effected in an organic solvent, for instance dichloromethane or tetrahydrofuran, at ambient or reduced temperature, for instance −80° to 100° C., over a period of several hours to a few days. Preferably phosgene or phosphorus oxychloride are used, at temperatures of from 0° to 20° C.

Alternatively, cyclisation may be effected using triphenylphosphine and carbon tetrachloride as the chlorinating reagent, in the presence of a tertiary amine, for instance triethylamine, in an inert solvent such as acetonitrile or acetonitrile-pyridine. This type of process is described by H. Vorbruggen and K. Krolikiewicz in *Tet. Letts.*, 1981, 4471: it is particularly advantageous in that the production of compounds of formula (II) and cyclisation of these to compounds of formula (IA) may be conducted in situ.

Compounds of formula (II) may also be cyclised using a carboxylic anhydride or mixed anhydride, such as trifluoroacetic anhydride. In this reaction the hydroxy groups of the 1-normon-2-yl moiety become acylated and must subsequently be deprotected. When trifluoroacetic anhydride is used to effect the cyclisation the trifluoroacetyl groups may be removed using aqueous base such as potassium carbonate. Appropriate deprotecting conditions for removing other acyl residues will be readily apparent to the skilled person. Alternatively the hydroxy groups of the 1-normon-2-yl moiety may be protected, prior to cyclising with a carboxylic anhydride, and deprotected by conventional methods such as described below.

The reaction of a compound of formula (III) with a compound of formula (IV) may conveniently be effected in an organic solvent, such as tetrahydrofuran, diethyl ether and dimethyl sulphoxide, at reduced or elevated temperature, such as from −80° to 100° C.

Conversion of one compound of formula (I) to another compound of formula (I) may be effected by conventional methods. Thus, for instance, substituents on the groups R¹ and R² may be modified or additional substituents may be inserted. Included within modification of the groups R¹ and R² are salification and esterification of a carboxy substituent, trans- and de-esterification of an ester-containing substituent and formation of the free carboxy group from a carboxylate salt. Another example of such conversion is the formation of alkanesulphinyl and alkanesulphonyl compounds from the corresponding alkylthio compound of formula (I). This latter conversion may be achieved using conventional oxidising agents such as percarboxylic acids, for instance m-chloroperbenzoic acid, in a suitable solvent.

Compounds of formula (II) as defined above are novel and useful as chemical intermediates in the aforementioned process.

Accordingly, the present invention also provides a compound of formula (II), as hereinbefore defined.

Compounds of formula (II) may be produced according to the reaction sequence shown in Scheme I below.

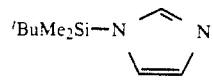

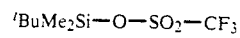

wherein X is halogen and each group L is independently selected from hydrogen, alkyl, alkoxy, aryl or aralkyl. A preferred silyating agent is trimethylsilyl chloride. Particularly suitable protecting groups are trimethylsilyl, t-butyldimethylsilyl and t-butyldiphenylsilyl groups. Preferred protecting groups are trimethyl-

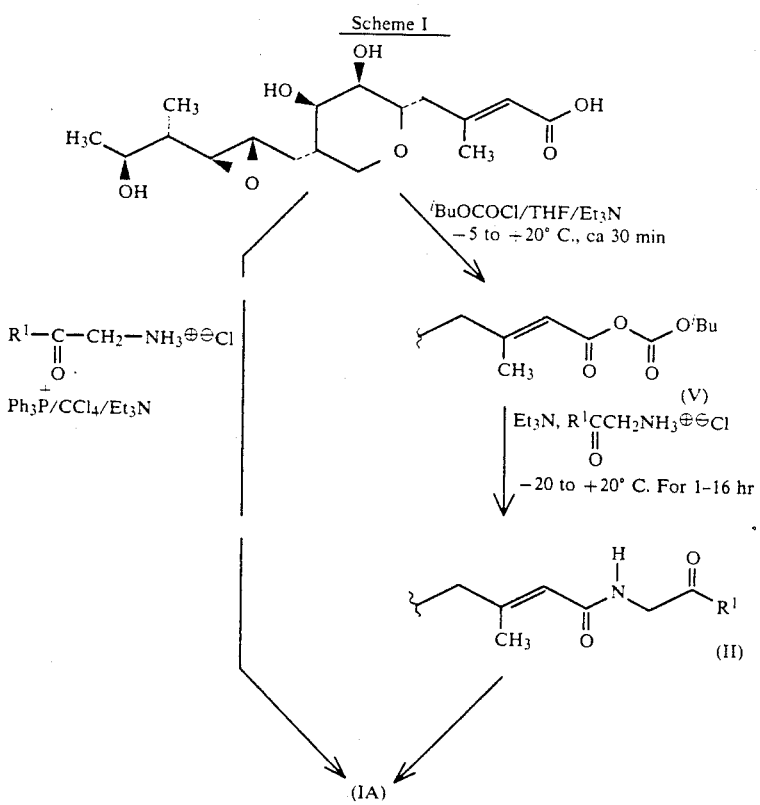

The hydroxyl groups of monic acid, and compounds of formulae (II) and (V) may be protected at any stage in this scheme, using conventional processes.

Particularly suitable protecting groups are silyl groups since these are readily removed under mild conditions. Such groups are introduced using conventional silylating agents, including halosilanes and silazanes, of the formulae below:

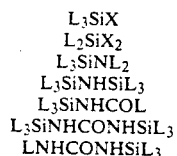

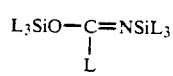

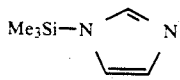

silyl groups because of their ease of removal.

The glycol function of monic acid and the compounds of formulae (II) and (III) may be protected by forming a cyclic derivative using a compound of formula (VI):

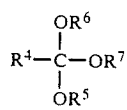

wherein $R^4$ is hydrogen or $C_{1-6}$ alkyl and each of $R^5$, $R^6$ and $R^7$ is $C_{1-6}$ alkyl. In the cyclic derivative $Z^1$ and $Z^2$ together are a moiety:

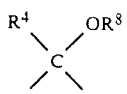

wherein $R^8$ is $C_{1-6}$ alkyl.

Suitably $R^4$ is hydrogen, methyl, ethyl, n- or iso-propyl; most suitably it is hydrogen. The groups $R^5$, $R^6$ and $R^7$ are suitably methyl, ethyl, n- or iso-propyl, n-, iso-, sec- or t-butyl; most suitably methyl.

Similarly the hydroxyl groups of a compound of formula (I) may be protected prior to conversion to a further compound of formula (I) as described above.

In each case the protecting groups described above may be removed by mild acid hydrolysis followed by alkaline hydrolysis, for instance, as described by J. P. Clayton, K. Luk and N. H. Rogers, in "Chemistry of Pseudomonic Acid, Part II", *J. C. S. Perkin Trans. I,* 1979, 308.

The compound of formula (III) wherein $Z^1$, $Z^2$ and $Z^3$ are hydrogen, and processes for its production, are described in U.K. Patent No. 1,587,060. Derivatives thereof wherein $Z^1$, $Z^2$ and $Z^3$ are hydroxyl protecting groups may be produced by conventional methods such as

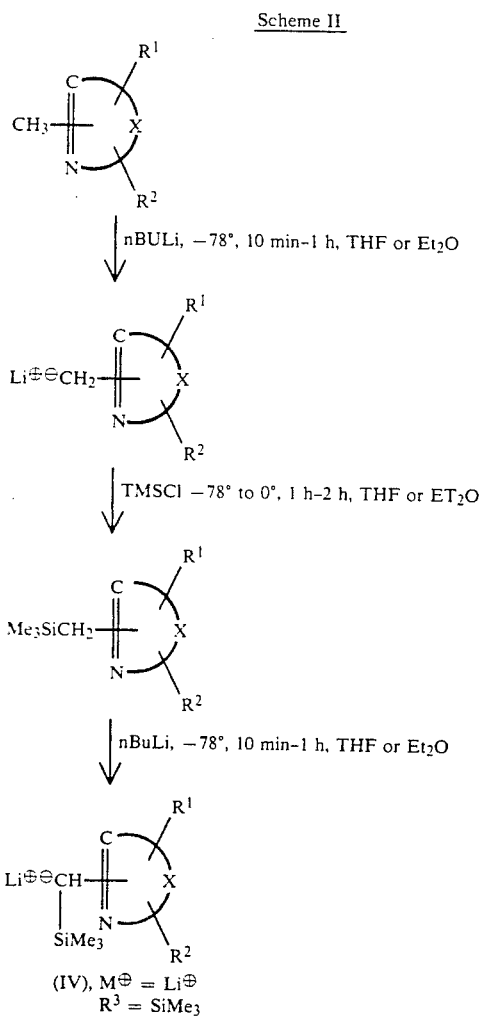

those mentioned above. When this compound is produced with hydroxyl protecting groups already in place it may be used directly or even in situ in the above reaction or it may be optionally deprotected and/or isolated.

Compounds of formula (IV) may be produced by conventional processes such as those shown in Scheme II.

When R is 2-oxazolyl, the corresponding compound of formula (IV) may be produced from the compound of formula (VIII) by conventional methods:

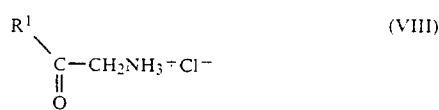

Preparation of the compounds of formula (VIII) is described in Organic Syntheses Coll. Vol. V, 909, and one method for converting these to compounds of formula (VII) is that described by J. L. La Mattina, [J. Org. Chem., (1980), 45, 2261]. Analogous processes to those of the reaction sequence from compounds of formula (VII) to compounds of formula (IV) are described by E. J. Corey and D. L. Boger [Tet. Letters, (1978), 5]; T. H. Chan [Acc. Chem. Res., (1977), 10, 442] and B. H. Lipshutz and R. W. Hungate [J. Org. Chem., (1981), 46, 1410].

An alternative procedure for producing compounds of formula (IV) is shown in Scheme III:

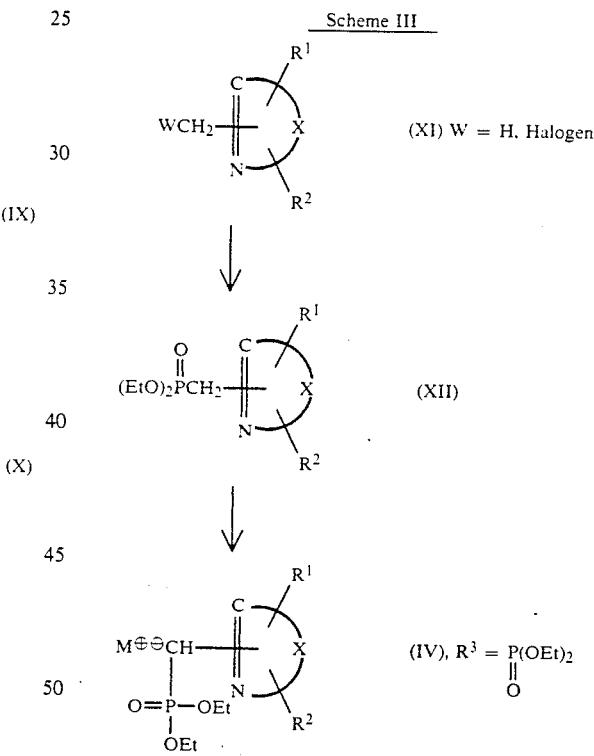

The production of oxazoles (cf compounds of formula (VII) in Scheme II) are described by R. A. Jeffreys [*J. Chem. Soc.,* (1947), 96] and suitable reaction conditions to produce compounds of formula (IV) wherein $R^3$ is

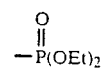

is described by W. S. Wadsworth Jr., [*Organic Reactions,* (1977), 25, 73].

The infections against which compounds of this invention are particularly useful include venereal disease. They are also effective in the treatment of respiratory infections such as bacterial bronchitis; and bacterial meningitis, non-specific urethritis and pneumonia. In animals it may be employed for the treatment of mastitis in cattle, for swine dysentery, and for mycoplasma infections in animals such as turkeys, chickens, pigs and cattle.

Some of the human and veterinary diseases either caused by mycoplasma species or in which they play a prominent role, and against which compounds of this invention are effective, are as follows:

|  | Avian |
|---|---|
| M. gallisepticum | chronic respiratory diseases (air-sacculitis) of chickens and turkeys |
|  | Bovine |
| M. bovis | mastitis, respiratory disease and arthritis of cattle |
| M. dispar | calf pneumonia |
|  | Porcine |
| M. suipneumoniae | enzootic pneumonia of pigs |
| M. hyorhinis | arthritis in pigs |
| M. hyosynoviae |  |
|  | Human |
| M. pneumoniae | primary atypical pneumonia |

Compounds of the present invention are particularly useful in the treatment of enzootic pneumonia in animals such as pigs, cattle and sheep, because they also have activity against the bacteria *Bordetella bronchiseptica*, *Pasteurella multocida* and *Haemophilus spp*, which often cause respiratory complications in cases of this disease.

This invention also provides a pharmaceutical or veterinary composition which comprises a compound of formula (I) (hereinafter referred to as the "drug") together with a pharmaceutically or veterinarily acceptable carrier or excipient.

The compositions may be formulated for administration by any route, and would depend on the disease being treated. The compositions may be in the form of tablets, capsules, powders, granules, lozenges, liquid or gel preparations, such as oral, topical or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinyl-pyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin, hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin the drug may be made up into a cream, lotion or ointment. Cream or ointment formulations that may be used for the drug are conventional formulations well known in the art, for example, as described in standard text books of pharmaceutics and cosmetics, such as Harry's Cosmeticology published by Leonard Hill Books, and the British Pharmacopoeia.

Suppositories will contain conventional suppository bases, e.g. cocoa-butters or other glyceride.

For parenteral administration, fluid unit dosage forms are prepared utilizing the drug and a sterile vehicle. The drug, depending on the vehicle and concentration used, can either be suspended or dissolved in the vehicle. In preparing solutions the drug can be dissolved in water for injection and filter sterilized before filling into a suitable vial or ampoule and sealing. Advantageously, adjuvants such as a local anaesthetic, preservative and buffering agents can be dissolved in the vehicle. To enhance the stability the composition can be frozen after filling into the vial and water removed under vacuum. The dry lyophilized powder is then sealed in the vial. Parenteral suspensions are prepared in substantially the same manner except that the drug is suspended in the vehicle instead of being dissolved and sterilisation cannot be accomplished by filtration. The drug can be sterilised by exposure to ethylene oxide before suspending in the sterile vehicle. Advantageously, a surfactant or wetting agent is included in the composition to facilitate uniform distribution of the drug.

For topical application to the ear, the drug may be made up into a solution or suspension in a suitable liquid carrier, such as water, glycerol, diluted ethanol, propylene glycol, polyethylene glycol or fixed oils.

For topical application to the eye, the drug is formulated as a solution or suspension in a suitable, sterile aqueous or non-aqueous vehicle. Additives, for instance buffers such as sodium metabisulphite or disodium edetate; preservatives including bactericidal and fungicidal agents, such as phenylmercuric acetate or nitrate, benzalkonium chloride or chlorhexidine, and thickening agents such as hypromellose may also be included.

The dosage employed for compositions administered topically will, of course, depend on the size of the area being treated. For the ears and eyes each dose will typically be in the range from 10 to 100 mg of the drug.

Veterinary compositions for intramammary treatment of mammary disorders in animals, especially bovine mastitis, will generally contain a suspension of the drug in an oily vehicle.

The compositions may contain from 0.1% to 99% by weight, preferably from 10-60% by weight, of the drug, depending on the method of administration. Where the compositions are in unit dose form, each dosage unit will preferably contain from 50-500 mg, of the drug. The dosage as employed for adult human treatment will preferably range from 100 mg to 3 g, per day, for instance 250 mg to 2 g of the drug per day, depending on the route and frequency of administration.

Alternatively, the drug may be administered as part of the total dietary intake. In this case the amount of drug employed may be less than 1% by weight of the diet and in preferably no more than 0.5% by weight. The diet for animals may consist of normal foodstuffs to which the drug may be added or the drug may be included in a premix for admixture with the foodstuff.

A suitable method of administration of the drug to animals is to add it to the animals' drinking water. In this case a concentration of the drug in the drinking water of about 5–500 μg/ml, for example 5–200 μg/ml, is suitable.

The present invention further provides a method for treating the human, or non-human animal which method comprises administering a compound of formula (I) as hereinbefore defined, to a human or non-human in need of such therapy.

Alternatively, a pharmaceutical composition as hereinbefore described may be employed in the treatment.

In particular aspects of the treatment there are provided methods for treating bacterial and/or mycoplasmal infections of human or non-human animals, especially venereal disease, respiratory infections such as bacterial bronchitis, bacterial meningitis, non-specific urethritis and pneumonia in humans, respiratory infections, mastitis, swine dysentery and pneumonia in animals.

The following Examples illustrate the invention, but are not intended to limit the scope in any way.

The following abbreviations have been used in the Examples:
DMF: N,N-dimethylformamide
THF: Tetrahydrofuran
MgSO$_4$: Anhydrous magnesium sulphate
Celite: (Trade Mark) is a grade of diatomaceous earth.

EXAMPLE 1

2-{3-[5-(2,3-Epoxy-5-hydroxy-4-methylhexyl)-3,4-dihydroxytetrahydropyran-2-yl]-2-methylprop-1(E)-enyl}-5-phenyloxazole; 2-(1-normon-2-yl)-5-phenyloxazole A

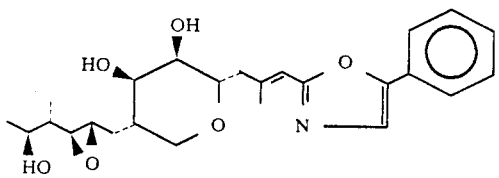

(a) N-Phenacyl-4-[5-(2,3-epoxy-5-hydroxy-4-methylhexyl)-3,4-dihydroxytetrahydropyran-2-yl]-3-methylbut-2(E)-enamide; phenacyl monamide A

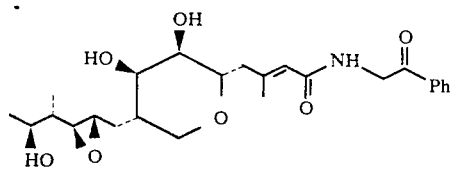

A solution of monic acid A (13.8 g, 40 mmol) in dry tetrahydrofuran (250 ml) was cooled to 0° C. and then triethylamine (5.4 ml, 40 mmol) and isobutylchloroformate (5.1 ml, 40 mmol) were added. The cooling bath was removed and after 30 min, triethylamine (5.4 ml, 40 mmol) and phenacylammonium chloride (6.6 g, 40 mmol) were added. After 16 h at 20° C. the reaction mixture was filtered, the filtrate evaporated to dryness under reduced pressure and the resulting residue purified by chromatography (50 g silica gel, 0 to 6% methanol in dichloromethane) to give phenacyl monamide A as a white foam (5.5–10.9 g, 30 to 60%);

i.r. spectrum: $\nu_{max}$ (film) 3400, 1690, 1660, 1630, 1600 cm$^{-1}$;

U.V. spectrum: $\lambda_{max}$ (EtOH) 240 nm ($\epsilon_m$ 22,400);

$^1$H nmr: $\delta_H$ (CDCl$_3$) 7.98(2H, d, H2″, 6″), 7.63(1H, t, H4″), 7.50(2H, t, H3″, 5″), 6.88(1H, t, NH), 5.86(1H, s, H2), 4.82(2H, d, H1′), 2.20(3H, s, CH$_3$-15), 1.20(3H, d, CH$_3$-14), 0.90(3H, d, CH$_3$-17);

$^{13}$C nmr: $\delta_C$ (CDCl$_3$) 194.6 (C2′), 167.1 (C1), 151.9 (C3), 134.5 (C1″), 133.8 (C4″), 128.8 (C2″, C6″), 128.7 (C3″, C5″), 119.6 (C2), 74.9 (C5), 70.8 (C13), 70.3 (C7), 68.8 (C6), 65.2 (C16), 60.9 (C11), 55.4 (C10), 46.1 (C1′), 42.5 (C4), 42.5 (C12), 39.5 (C8), 31.6 (C9), 20.5 (C14), 18.8 (C15), 12.3 (C17);

mass spectrum: m/e (relative intensity) 461(M+, 11%), 327(18), 217(96), 136(100) Found 461.2415. C$_{25}$H$_{35}$NO$_7$ requires 461.2414.

Analysis: Found: C, 65.0; H, 7.5; N, 3.1% C$_{25}$H$_{35}$NO$_7$ requires: C, 65.1; H, 7.6; N, 3.0%.

(b) 2-(1-Normon-2-yl)-5-phenyloxazole A

Phenacyl monamide A (0.92 g, 2 mmol) was treated with chlorotrimethylsilane (0.76 ml, 6 mmol) and triethylamine (0.84 ml, 6 mmol) and a catalytic amount of 4-N,N-dimethylaminopyridine in tetrahydrofuran (20 ml) until protection was complete (6 h by t.l.c.). The resulting solution was filtered and evaporated to dryness under reduced pressure. The residual oil was dissolved in dichloromethane (20 ml) and reacted with phosgene in toluene (2.3 mmol) in the presence of triethylamine (0.6 ml, 4.6 mmol) at 5° C. for 16 h. The reaction mixture was poured into aqueous sodium bicarbonate, and extracted with ethyl acetate. The ethyl acetate extract was washed with brine, dried (magnesium sulphate) and evaporated under reduced pressure. The residue was dissolved in dioxan (40 ml) and water (10 ml) and concentrated aqueous hydrochloric acid (12 drops) added. After 12 min the solution was neutralised with aqueous sodium bicarbonate and extracted with ethyl acetate. The extracts were washed with brine, dried (magnesium sulphate) and evaporated under reduced pressure to leave a brown oil which was purified by chromatography (50 g silica, 0 to 10% methanol in dichloromethane). 2-(1-Normon-2-yl)-5-phenyloxazole A, the second component to be eluted from the column, was obtained as a white foam (0.11 g, 14%);

i.r. spectrum: $\nu_{max}$ (film) 3400, 1655, 1120, 1050 cm$^{-1}$;

U.V. spectrum: $\lambda_{max}$ (EtOH) 301 nm ($\epsilon_m$ 20,800);

$^1$H nmr: $\delta_H$ (CD$_3$OD) 7.3–7.8(6H, m, aryl+Het-H), 6.26(1H, s, H2), 2.20(3H, s, CH$_3$-15), 1.21(3H, d, CH$_3$-14), 0.90(3H, d, CH$_3$-17);

$^{13}$C nmr: $\delta_C$ (CDCl$_3$) 161.2 (C1), 150.0 (C3), 146.8, 128.9, 128.1, 124.1, 122.5 (aryl+heteroaryl), 113.2 (C2), 75.4 (C5), 71.2 (C13), 70.5 (C7), 69.0 (C6), 65.5 (C16), 61.2 (C11), 55.6 (C10), 42.8 (C4, C12), 39.6 C8), 31.8 (C9), 20.8 (C14), 19.6 (C15), 12.6 (C17);

mass spectrum: m/e (relative intensity) 443(M+, 11%), 199(100) Found: 443.2270. C$_{25}$H$_{33}$NO$_6$ requires: 443.2305.

(c) 2-(1-Normon-2-yl)-5-phenyloxyzole A (alternative cyclisation)

Trifluoroacetic anhydride (0.5 ml) was added to phenacyl monamide A (92 mgs, 0.20 mmol) in a flask cooled to 0° C. The cooling bath was removed and the homogeneous solution stirred for 1 h at room temperature. The excess anhydride was removed under reduced pressure then the residue was stirred with aqueous potassium carbonate/THF (1:4) for 2 days. This solution was extracted with ethyl acetate (2×30 ml), dried (MgSO₄) and solvent removed under reduced pressure to leave the crude product (89 mgs). Column chromatography (0 to 5% methanol in dichloromethane on silica gel: 2 g) gave the title compound (43.5 mgs, 0.10 mmol, 50%) which was identical to sample obtained in Example 1(b).

EXAMPLE 2

2-{3-[5-(2,3-Epoxy-5-hydroxy-4-methylhexyl)-3,4-dihydroxytetrahydropyran-2-yl]-2-methylprop-1(E)-enyl}-5-phenyloxazole; 2-(1-normon-2-yl)-5-phenyloxazole A (a) A solution of 3-[5-(2,3-epoxy-5-hydroxy-4-methylhexyl)-3,4-dihydroxytetrahydropyran-2-yl]propan-2-one (300 mg, 1 mmol) in tetrahydrofuran (10 ml) was treated with chlorotrimethylsilane (0.42 ml, 3.3 mmol), triethylamine (0.46 ml, 3.3 mmol) and a catalytic amount of 4-N,N-dimethylaminopyridine. After 2 h at 20° C. the resulting "TMS-protected ketone" was isolated, by filtration and evaporation to dryness under reduced pressure, as an oil which was dissolved in tetrahydrofuran (5 ml). This solution was set aside for addition to the lithium anion, the production of which is described in part (b) below.

(b) A solution of 2-methyl-5-phenyloxazole (175 mg, 1.1 mmol) in dry tetrahydrofuran (10 ml) was cooled to −78° C. under an atmosphere of argon. A solution of n-butyl lithium in hexane (0.9 ml, 1.2M, 1.1 mmol) was added, followed after 10 min by chlorotrimethylsilane (0.15 ml, 1.1 mmol). After 40 min at −78° C. the solution was warmed to 0° C. for 45 min and then recooled to −78° C. A further quantity of n-butyl lithium (0.9 ml, 1.1 mmol) was added and the solution stirred at −78° C. for 40 min.

(c) The solution of "TMS-protected ketone" described in part (a) above was added to the reaction mixture obtained in part (b) above and the mixture was stirred for 2 h at 20° C. and then poured into aqueous ammonium chloride. The resultant mixture was extracted with ethyl acetate and the organic extracts were combined, dried (magnesium sulphate) and evaporated under reduced pressure. The resulting residue was dissolved in tetrahydrofuran/water (4:1, 25 ml) and concentrated hydrochloric acid (6 drops). After stirring for 12 min excess sodium bicarbonate was added and the mixture extracted with ethyl acetate. The organic extracts were combined, dried (magnesium sulphate), and evaporated under reduced pressure to an oil, which was purified by chromatography on silica gel (10 g) eluting with a gradient of 0 to 4% methanol in dichloromethane. 2-(1-Normon-2-yl)-5-phenyloxazole A was obtained as a white foam (156 mg, 35%) and found to be identical to the sample obtained in Example 1.

In addition, the less polar Z-isomer, 2-{3-[5-(2,3-epoxy-5-hydroxy-4-methylhexyl)-3,4-dihydroxytetrahydropyran-2-yl]-2-methylprop-1(Z)-enyl}-5-phenyloxazole (15 mg, 3%);

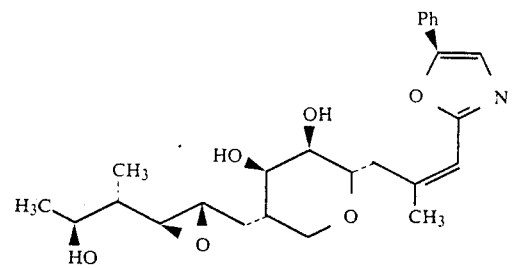

was also obtained.

i.r. spectrum: $\nu_{max}$ (film) 3600–3100, 2970, 2930, 1650, 1450, 1110, 1050, 950, 910, 760, 690 cm$^{-1}$;

U.V. spectrum: $\lambda_{max}$ (EtOH) 302 nm ($\epsilon_m$ 17,100);

¹H nmr: $\delta_H$ (CDCl₃) 0.95(3H, d, J=7 Hz, CH₃-17), 1.20(3H, d, J=7 Hz, CH₃-14), 1.29(1H, m, CH-12), 1.60(1H, dt, J=15, 5 Hz, CH₂9), 2.04(1H, m, CH-8), 2.13(3H, d, J=0.5 Hz, CH₃-15), 2.68(1H, dd, J=10, 2 Hz, CH-11), 2.75-3.00(2H, m, CH-10, CH₂-4), 3.06(1H, dd, J=15, 5 Hz, CH₂-4), 3.5-4.0(6H, m), 6.30(1H, s, CH-2), 7.32(1H, s, CH-1'), 7.33-7.70(5H, m, Ph);

¹³C nmr: $\delta_C$ (CDCl₃) 12.7 (C17), 20.7 (C14), 27.4 (C15), 31.9 (C9), 36.3 (C4), 38.9 (C8), 43.0 (C12), 56.1 (C10), 61.5 (C11), 65.6 (C16), 66.9 (C6), 70.3 (C7), 71.3 (C13), 76.6 (C5), 112.5 (C2), 121.6, 124.3, 127.7, 128.6, 129.0 (aromatic+heteroaromatic), 150.4 (C3), 166.8 (C1);

mass spectrum: m/e (relative intensity) 443(M⁺, 10%), 211(32), 199(100), 77(32), 69(30), 55(39), 45(64), 43(63), 41(62) Found: 443.2334. C₂₅H₃₃NO₆ requires: 443.2308.

EXAMPLE 3

2-{3-[5-(2,3-Epoxy-5-hydroxy-4-methylhexyl)-3,4-dihydroxytetrahydropyran-2-yl]-2-methylprop-1(E)-enyl}-5-p-nitrophenyloxazole; 5-p-nitro-phenyl-2-(1-normon-2-yl)-oxazole A

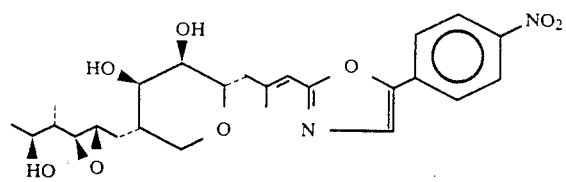

(a) N-p-Nitrophenacyl-4-[5-(2,3-epoxy-5-hydroxy-4-methylhexyl-3,4-dihydroxytetrahydropyran-2-yl]-3-methylbut-2(E)-enamide; p-nitrophenacyl monamide A

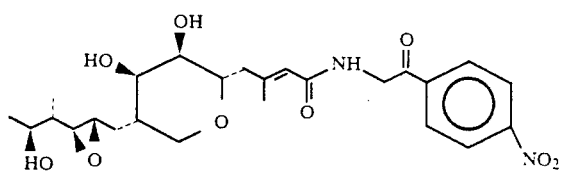

To a solution of monic acid A (3.1 g, 9 mmol) in dry tetrahydrofuran (50 ml) were added triethylamine (1.2 ml, 9 mmol) and isobutylchloroformate (1.1 ml, 9 mmol). After 30 min p-nitrophenacylammonium chloride (2.2 g, 9 mmol) and additional triethylamine (1.2 ml, 9 mmol) were added. The reaction mixture was stirred for 2 h at 20° C., poured into brine and the resulting mixture extracted with ethyl acetate. The combined extracts were washed with aqueous sodium bicarbonate, dried (magnesium sulphate) and evaporated to dryness under reduced pressure. Chromatography on silica gel (20 g) eluting with a gradient of 0 to 10% methanol in dichloromethane afforded the p-nitrophenacyl monamide A as a yellow foam (1.4 g, 31%);

i.r. spectrum: $\nu_{max}$(film) 3380, 1710, 1660, 1630, 1605, 1525, 1350 cm$^{-1}$;

U.V. spectrum: $\lambda_{max}$ (EtOH) 223 nm ($\epsilon_m$ 16,200), 262 nm ($\epsilon_m$ 13,200);

$^1$H nmr: $\delta_H$(CD$_3$OD) 8.28(4H, ABq, aryl), 5.91(1H, s, H2), 4.73(2H, s, H1′), 2.13(3H, s, CH$_3$-15), 1.15(3H, d, CH$_3$-14), 0.90(3H, d, CH$_3$-17).

(b) 5-p-Nitrophenyl-2-(1-normon-2-yl)-oxazole A p-Nitrophenacyl monamide A (1.01 g, 2 mmol) was treated with chlorotrimethylsilane (0.76 ml, 6 mmol), triethylamine (0.84 ml, 6 mmol) and a catalytic amount of 4-N,N-dimethylaminopyridine in tetrahydrofuran (20 ml) until protection was complete (16 h as indicated by t.l.c.). The resulting solution was filtered and evaporated under reduced pressure. The residue was dissolved in tetrahydrofuran (30 ml) and reacted with phosphoryl chloride (0.3 ml, 3.5 mmol) and pyridine (0.5, 6 mmol) for 16 h at 20° C. The reaction mixture was poured into aqueous sodium bicarbonate, and extracted with ethyl acetate. The combined extracts were washed with brine, dried (magnesium sulphate) and evaporated under reduced pressure to give an oil, which was dissolved in dioxan (40 ml) and water (10 ml). Concentrated aqueous hydrochloric acid (12 drops) was added and after 12 min the solution neutralised with aqueous sodium bicarbonate and extracted with ethyl acetate. The extracts were washed with brine, dried (magnesium sulphate) and evaporated under reduced pressure to leave a brown oil which was purified by chromatography on silica gel (50 g) eluting with a gradient of 4 to 10% methanol in dichloromethane to give 5-p-nitrophenyl-2-(1-normon-2-yl)-oxazole A as a yellow foam (0.08 g, 8%);

i.r. spectrum: $\nu_{max}$ (film) 3410, 1650, 1605, 1520 cm$^{-1}$;

U.V. spectrum: $\lambda_{max}$ (EtOH) 267 nm ($\epsilon_m$ 11,900), 356 nm ($\epsilon_m$ 18,200);

$^1$H nmr: $\delta_H$ (CDCl$_3$) 8.28 and 7.79(4H, ABq, aryl), 7.56(1H, s, heterocyclyl), 6.32(1H, s, H2), 2.34(3H, s, CH$_3$-15), 1.21(3H, d, CH$_3$-14), 0.94(3H, d, CH$_3$-17);

$^{13}$C nmr: $\delta_C$ (CDCl$_3$) 162.7 (C1), 149.0 (C3), 147.7 (aryl C4), 147.0 (oxazole C4), 134.0 (aryl C1), 126.3 (oxazole C5), 124.5 (aryl C2, C6), 124.3 (aryl C3, C5), 112.8 (C2), 75.3 (C5), 71.3 (C13), 70.5 (C7), 69.0 (C6), 65.5 (C16), 61.2 (C11), 55.5 (C10), 43.0 (C12), 42.8 (C4), 39.7 (C8), 31.7 (C9), 20.8 (C14), 19.8 (C15), 12.7 (C17).

EXAMPLE 4

2-{3-[5-(2,3-Epoxy-5-hydroxy-4-methylhexyl)-3,4-dihydroxytetrahydropyran-2-yl]-2-methylprop-1(E)-enyl}-5-p-methoxyphenyloxazole;

5-p-methoxyphenyl-2-(1-normon-2-yl)oxazole A

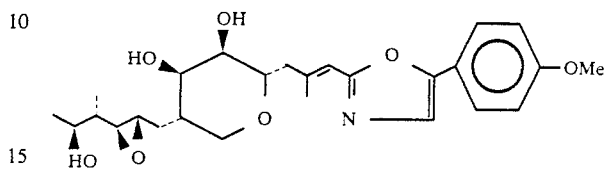

A solution of 2-methyl-5-p-methoxyphenyloxazole (190 mg, 1.0 mmol) in dry tetrahydrofuran (10 ml) was cooled to −78° C. under an argon atmosphere. A solution of n-butyl lithium in hexane (0.9 ml, 1.2M, 1.1 mmol) was added, and after 10 min chlorotrimethylsilane (0.15 ml, 1.1 mmol). After 40 min at −78° C., the solution was warmed to 0° C. for 45 min and then re-cooled to −78° C. More n-butyl lithium (0.9 ml, 1.1 mmol) was then added, and the solution stirred at −78° C. for 40 min. A solution of the "TMS-protected ketone" derived from 3-[5-(2,3-epoxy-5-hydroxy-4-methylhexyl)-3,4-dihydroxytetrahydropyran-2-yl]-propan-2-one, by the method described in Example 2, (1 mmol) in tetrahydrofuran (10 ml) was added and the reaction mixture stirred at 20° C. for 2 h, poured into aqueous ammonium chloride and extracted with ethyl acetate. The combined organic fractions were dried (magnesium sulphate) and evaporated under reduced pressure. The resulting residue was dissolved in tetrahydrofuran/water (4:1, 25 ml). Concentrated hydrochloric acid (6 drops) was added, followed 12 min later by excess aqueous sodium bicarbonate. The mixture was extracted with ethyl acetate and the combined extracts dried (magnesium sulphate), evaporated under reduced pressure and the residue purified by chromatography on silica gel (10 g) eluting with a gradient of 0 to 4% methanol in dichloromethane to give 5-p-methoxyphenyl-2-(1-normon-2-yl)-oxazole A as a white foam (0.07 g, 15%).

i.r. spectrum: $\nu_{max}$ (film) 3400, 1655, 1615, 1500 cm$^{-1}$;

U.V. spectrum: $\lambda_{max}$ (EtOH) 307 nm ($\epsilon_m$ 22.700);

$^1$H nmr: $\delta_H$ (CDCl$_3$) 7.55 and 6.93(4H, ABq, aryl), 7.22(1H, s, heteraryl), 6.29(1H, s, H2), 3.81(3H, s, OMe), 2.21(3H, s, CH$_3$-15), 1.21(3H, d, CH$_3$-14), 0.94(3H, d, CH$_3$-17);

$^{13}$C nmr: $\delta_C$ (CDCl$_3$) 160.6 (C1), 159.8 (aryl C4), 150.1 (C3), 145.9 (oxazole C4), 125.6 (aryl C2, C6), 121.1 (aryl C1), 119.9 (oxazole C5), 114.5 (aryl C3, C5), 113.3 (C2), 75.4 (C5), 71.3 (C13), 70.5 (C7), 69.0 (C6), 65.5 (C16), 61.3 (C11), 55.5 (C10), 55.4 (OMe), 42.8 (C4, C12), 39.5 (C8), 31.8 (C9), 20.8 (C14), 19.6 (C15), 12.6 (C17).

EXAMPLE 5

2-{3-[5-(2,3-Epoxy-5-hydroxy-4-methylhexyl)-3,4-dihydroxytetrahydropyran-2-yl]-2-methylprop-1(E)-enyl}-5-m-cyanophenyloxazole;

5-m-cyanophenyl-2-(1-normon-2-yl)oxazole A

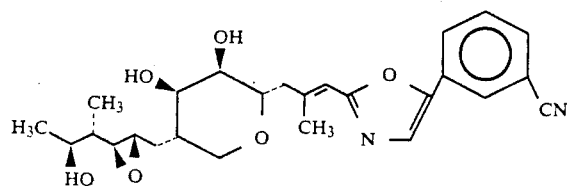

A solution of 2-methyl-5-m-cyanophenyloxazole (200 mg, 1.1 mmol) in dry tetrahydrofuran (10 ml) was cooled to −78° C. under an argon atomosphere. A solution of n-butyl lithium in hexane (0.9 ml, 1.2M, 1.1 mmol) was added, and after 10 min, chlorotrimethylsilane (0.15 ml, 1.1 mmol). After 40 min at −78° C., the solution was warmed to 0° C. for 45 min and then re-cooled to −78° C. More n-butyl lithium (0.9 ml, 1.1 mmol) was then added, and the solution stirred at −78° C. for 40 min. A solution of the "TMS-protected derivative" of 3-[5-(2,3-epoxy-5-hydroxy-4-methylhexyl)-3,4-dihydroxytetrahydropyran-2-yl]-propan-2-one (1 mmol) in tetrahydrofuran (10 ml) (prepared by the method described in Example 2), was added and the reaction mixture stirred at 20° C. for 2 h, poured into aqueous ammonium chloride and extracted with ethyl acetate. The combined organic fractions were dried (magnesium sulphate) and evaporated under reduced pressure. The resulting residue was dissolved in 4:1 tetrahydrofuran:water (25 ml). Concentrated hydrochloric acid (6 drops) was then added, followed, after 12 min by excess aqueous sodium bicarbonate. The mixture was extracted with ethyl acetate and the combined extracts, dried (magnesium sulphate), evaporated under reduced pressure and the residue purified by chromatography on silica gel (10 g), eluting with a gradient of 0 to 4% methanol in dichloromethane to give 5-m-cyanophenyl-2-(1-normon-2-yl)oxazole A as a yellow foam (0.035 g, 7%);

i.r. spectrum $\nu_{max}$ (film) 3400, 2225, 1680, 1655, 1610 cm$^{-1}$

U.V. spectrum $\lambda_{max}$ (EtOH) 305 nm ($\epsilon_m$ 28,600);

$^1$H nmr $\delta_H$ (CDCl$_3$) 7.5–7.9(4H, m, aryl), 7.44(1H, s, H4'), 6.31(1H, s, H2), 2.33(3H, s, CH$_3$-15), 1.24(3H, d, CH$_3$-14), 0.95(3H, d, CH$_3$-17);

$^{13}$C nmr $\delta_C$ (CDCl$_3$) 165.5 (C1), 148.2 (C3), 147.5 (C4'), 131.2, 129.8, 127.8, 127.3, 123.5 (aryl), 124.5 (C5'), 112.9 (C2), 75.2 (C5), 71.3 (C13), 70.5 (C7), 69.0 (C6), 65.4 (C16), 61.2 (C11), 55.5 (C10), 42.8 (C4, C12), 39.6 (C8), 31.7 (C9), 20.8 (C14), 19.7 (C15), 12.7 (C17);

mass spectrum m/e (relative intensity) 468(M+, 6%), 283(34), 224(100) (found 468.2273, C$_{26}$H$_{32}$N$_2$O$_6$ requires 468.2289).

EXAMPLE 6

2-{3-[5-(2,3-Epoxy-5-hydroxy-4-methylhexyl)-3,4-dihydroxytetrahydropran-2-yl]-2-methylprop-1(E)-enyl}-5-m-nitrophenyloxazole;

5-m-nitrophenyl-2-(1-normon-2-yl)oxazole A

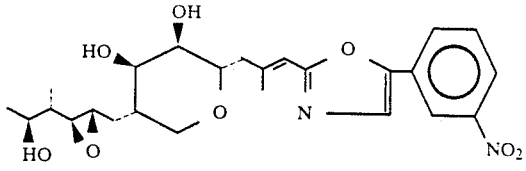

(a) N-m-Nitrophenacyl-4-[5-(2,3-epoxy-5-hydroxy-4-methylhexyl-3,4-dihydroxytetrahydropyran-2-yl]-3 methylbut-2(E)enamide; m-nitrophenacyl monamide A

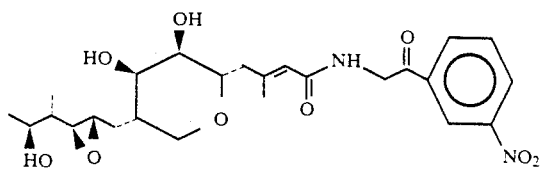

To a solution of monic acid A (3.1 g, 9 mmol) in dry tetrahydrofuran (50 ml) were added triethylamine (1.2 ml, 9 mmol) and isobutylchloroformate (1.1 ml, 9 mmol). After 30 min m-nitrophenacylammonium chloride (2.2 g, 9 mmol) and additional triethylamine (1.2 ml, 9 mmol) were added). The reaction mixture was stirred for 2 h at 20° C., poured into brine and the resulting mixture extracted with ethyl acetate. The combined extracts were washed with aqueous sodium bicarbonate, dried (magnesium sulphate) and evaporated to dryness under reduced pressure. Chromatography on silica gel (20 g) eluting with a gradient of 0 to 10% methanol in dichloromethane afforded m-nitrophenacyl monamide A as yellow crystals, mp 132°–135° C. (dec., CH$_2$Cl$_2$), (2.7 g, 60%);

$\nu_{max}$ (KBr) 3470, 3340, 1705, 1660, 1635, 1625, 1350 cm$^{-1}$;

$\lambda_{max}$ (EtOH) 227 nm ($\epsilon_m$ 30,600);

$\delta_H$ (CD$_3$OD) 8.80(1H, s, H2''), 8.49(1H, dd, H4''), 8.38(1H, dd, H6''), 7.80(1H, t, H5''), 5.91(1H, s, H2), 4.88(2H, s, H1'), 2.19(3H, s, CH$_3$-15), 1.23(3H, d, CH$_3$-14), 0.96(3H, d, CH$_3$-17);

$\delta_C$(CD$_3$OD) 194.5 (C2'), 169.3 (C1), 153.0 (C3), 149.5 (C3''), 137.4 (C1''), 134.4 (C6''), 131.0 (C5''), 128.4 (C4''), 66.0 (C16), 61.1 (C11), 56.5 (C10), 47.0 (C1'), 43.3 (C4), 43.3 (C12), 41.0 (C8), 32.6 (C9), 20.3 (C14), 19.0 (C15), 12.2 (C17).

(b) 5-m-Nitrophenyl-2-(1-normon-2-yl)oxazole A m-Nitrophenacyl monamide A (1.45 g, 3 mmol) in acetonitrile (20 ml) was treated with chlorotrimethylsilane (1.3 ml, 10 mmol), triethylamine (1.4 ml, 10 mmol) and 4-N,N-dimethylaminopyridine (50 mg) for 2 h at 20° C. The mixture was then filtered and evaporated under reduced pressure, and the resulting residue extracted with ether. The combined ether extracts were filtered and evaporated under reduced pressure and the resulting residue dissolved in a mixture of acetonitrile (15 ml), pyridine (15 ml), triethylamine (0.8 ml, 6 mmol) and tetrachloromethane (1.2 ml, 12 mmol). Triphenylphosphine (1.6 g, 6 mmol) was then added and the mixture was allowed to stand at 20° C. for 2 h and then at 5° C. for 16 h. The reaction mixture was poured into aqueous sodium bicarbonate, and extracted with ethyl acetate. The combined extracts were washed with brine, dried (magnesium sulphate) and evaporated under reduced pressure to give an oil, which was dissolved in dioxan (40 ml) and water (10 ml). Concentrated aqueous hydrochloric acid (12 drops) was added and after 12 min the solution neutralised with aqueous sodium bicarbonate and extracted with ethyl acetate. The extracts were washed with brine, dried (magnesium sulphate) and evaporated under reduced pressure to leave a brown oil which was purified by chromatography on silica gel (50 g) eluting with a gradient of 4 to 10% methanol in dichloromethane to give 5-m-nitrophenyl-2-(1-normon-2-yl)oxazole A as a yellow foam (0.18 g, 12%);

i.r. spectrum $\nu_{max}$(film) 3400, 1655, 1530, 1350 cm$^{-1}$;

U.V. spectrum $\lambda_{max}$ (EtOH) 307 nm ($\epsilon_m$ 16,700);

$^1$H nmr $\delta_H$ (CDCl$_3$) 8.45(1H, s, H2''), 8.14(1H, d, H4''), 7.92(1H, d, H6''), 7.60(1H, t, H5''), 7.51(1H, s, H4'), 6.31(1H, s, H2), 2.34(3H, s, CH$_3$-15), 1.22(3H, d, CH$_3$-14), 0.93(3H, d, CH$_3$-17);

$^{13}$C nmr $\delta_C$ (CDCl$_3$) 162.7 (C1), 148.9 (C3), 148.6 (C4'), 147.5 (C3''), 130.0 (C6''), 129.7 (C1''), 129.4 (C5'), 124.8 (C5''), 122.5 (C4''), 118.7 (C2''), 112.7 (C2), 75.3 (C5), 71.2 (C13), 70.5 (C7), 69.0 (C6), 65.5 (C16), 61.2 (C11), 55.6 (C10), 42.9 (C12), 42.8 (C4), 39.6 (C8), 31.7 (C9), 20.8 (C14), 19.7 (C15), 12.6 (C17);

mass spectrum m/e (relative intensity) 488(M$^+$, 7%), 244(100), 214(48) (Found 488.2168, C$_{25}$H$_{32}$N$_2$O$_8$ requires 488.2181).

EXAMPLE 7

2-{3-[5-(2,3-Epoxy-5-hydroxy-4-methylhexyl)-3,4-dihydroxytetrahydropyran-2-yl]-2-methylprop-1(E)-enyl}-5-(7-methoxycarbonylheptyl)oxazole;
5-(7-Methoxycarbonylheptyl)-2-(1-normon-2-yl)oxazole A

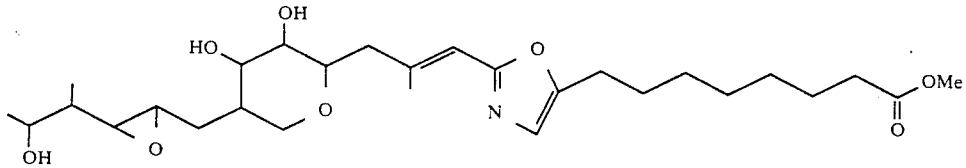

(a) N-(9-Methoxycarbonyl-2-oxononyl)-4-[5-(2,3-epoxy-5-hydroxy-4-methylhexyl-3,4-dihydroxytetrahydropyran-2-yl]-3-methylbut-2(E)-enamide; 9-Methoxycarbonyl-2-oxononyl monamide A

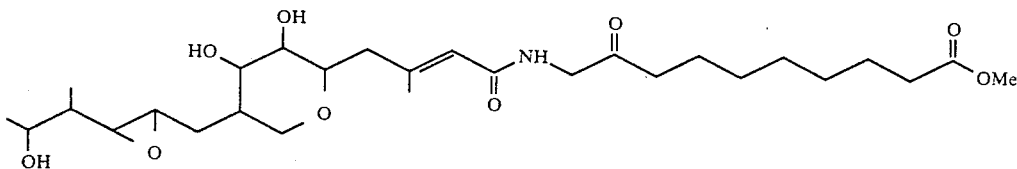

To a solution of monic acid A (2.38 g, 7 mmol) in dry tetrahydrofuran (50 ml) were added triethylamine (0.98 ml, 7 mmol) and isobutylchloroformate (0.91 ml, 7 mmol). After 30 min, methyl 10-amino-9-oxodecanoate hydrochloride (2.1 g, 7 mmol) and more triethylamine (0.98 ml, 7 mmol) were added. The reaction mixture was stirred for 2 h at 20° C., poured into brine and the resulting mixture extracted with ethyl acetate. The combined extracts were washed with aqueous sodium bicarbonate, dried (magnesium sulphate) and evaporated to dryness under reduced pressure. Chromatography on silica gel (20 g) eluting with a gradient of 0 to 10% methanol in dichloromethane afforded the amide as a colourless oil (0.50 g, 14%);

$\nu_{max}$ (film) 3400, 1725, 1660, 1635 cm$^{-1}$;

$\delta_H$ (CDCl$_3$) 6.50(1H, bs, NH), 5.76(1H, s, H2), 4.14(2H, d, H1'), 3.65(3H, s, OMe), 2.16(3H, s, CH$_3$-15), 1.19(3H, d, CH$_3$-14), 0.90(3H, d, CH$_3$-17).

(b) 5-(7-Methoxycarbonylheptyl)-2-(1-normon-2-yl)oxazole A

9-Methoxycarbonyl-2-oxononyl monamide A (0.50 g, 1 mmol) in tetrahydrofuran (20 ml) was treated with chlorotrimethylsilane (0.8 ml, 6 mmol), triethylamine (0.9 ml, 6 mmol) and 4-N,N-dimethylaminopyridine (50 mg) for 16 h at 20° C. The mixture was then filtered and evaporated under reduced pressure, and the resulting residue extracted with ether. The combined ether extracts were filtered and evaporated under reduced pressure and the resulting residue dissolved in a mixture of acetonitrile (6 ml), pyridine (6 ml), triethylamine (0.28 ml, 2 mmol) and tetrachloromethane (0.4 ml, 4 mmol). Triphenylphosphine (0.53 g, 2 mmol) was then added and the mixture stirred for 3 h at 20° C. and then poured into aqueous sodium bicarbonate, and extracted with ethyl acetate. The combined extracts were washed with brine, dried (magnesium sulphate) and evaporated under reduced pressure to give an oil, which was dissolved in dioxan (40 ml) and water (10 ml). Concentrated aqueous hydrochloric acid (12 drops) was added and after 12 min the solution neutralised with aqueous sodium bicarbonate and extracted with ethyl acetate. The extracts were washed with brine, dried (magnesium sulphate) and evaporated under reduced pressure to leave a brown oil which was purified by chromatography on silica gel (10 g) eluting with a gradient of 4 to 10% methanol in dichloromethane to give the oxazole as a yellow oil (0.16 g, 29%);

$\nu_{max}$ (film) 3360, 1740, 1725 sh, 1635 cm$^{-1}$;

$\lambda_{max}$ (EtOH) 266 nm ($\epsilon_m$ 11,200);

$\delta_H$(CDCl$_3$) 6.72(1H, s, H4'), 6.16(1H, s, H2), 3.65(3H, s, OCH$_3$), 2.64(2H, t, H1''), 2.32(2H, t, H7''), 2.21(3H, s, CH$_3$-15), 1.23(3H, d, CH$_3$-17);

$\delta_C$(CDCl$_3$) 174.5 (ester CO), 160.8 (C1), 151.8 (C4'), 145.5 (C3), 122.4 (C5'), 113.3 (C2), 75.4 (C5), 70.9 (C13), 68.9 (C6), 65.6 (C16), 61.21 (C11), 55.6 (C10), 51.4 (OMe), 42.7 (C4, C12), 39.6 (C8), 34.1 (C7''), 31.9 (C9), 29.0, 28.9, 28.9, 27.5, 25.5, 24.9 (C1''-C6''), 20.6 (C14), 19.3 (C15), 12.4 (C17);

m/e (relative intensity) 523(M+, 6%), 420(10), 308(17), 279(100) (Found: 523.3154, $C_{28}H'd\ 45NO_8$ requires 523.3164).

EXAMPLE 8

2-{3-[5-(2,3-Epoxy-5-hydroxy-4-methylhexyl)-3,4-dihydroxytetrahydropyran-2-yl]-2-methylprop-1(E)-enyl}-5-phenyloxazole; 2-(1-normon-2-yl)-5-phenyloxazole A To a solution of monic acid A (1.03 g, 3 mmol) in dry tetrahydrofuran (50 ml) were added 4-N,N-dimethylaminopyridine (50 mg), triethylamine (1.82 ml, 13 mmol) and chlorotrimethylsilane (1.65 ml, 13 mmol). After 3 h the solution was filtered and the filtrated evaporated under reduced pressure. The resulting residue was partitioned between aqueous ammonium chloride and ethyl acetate, and the organic part then washed with brine, dried (magnesium sulphate) and evaporated under reduced pressure to give 6,7,13-tris(trimethylsilyl)monic acid.

The latter was dissolved in a mixture of acetonitrile (10 ml), pyridine (10 ml), tetrachloromethane (1.5 ml, 15 mmol), and triethylamine (1.6 ml, 12 mmol). Phenacylammonium chloride (0.51 g, 3 mmol) and triphenylphosphine (0.8 g, 3 mmol) were added and, after an hour, more triphenylphosphine (1.6 g, 6 mmol) was added. After a further 16 h the reaction mixture was poured into a mixture of brine and aqueous sodium bicarbonate, and extracted with ethyl acetate. The combined extracts were washed with brine, dried (magnesium sulphate) and evaporated under reduced pressure to give an oil, which was dissolved in a mixture of tetrahydrofuran (60 ml) and water (15 ml). Concentrated hydrochloric acid (20 drops) was added and after 12 min the solution poured into aqueous sodium bicarbonate. The resulting mixture was extracted with ethyl acetate, and the extracts washed with brine, dried (magnesium sulphate) and evaporated under reduced pressure to leave a brown oil which was purified by chromatography on silica gel (50 g), eluting with 0 to 8% methanol in dichloromethane, from which 2-(1-normon-2-yl)-5-phenyloxazole A was obtained as a white foam (0.28 g, 21%), identical to that obtained in Examples 1 and 2.

EXAMPLE 9

2-{3-[5-(2,3-Epoxy-5-hydroxy-4-methylhexyl-3,4-dihydroxytetrahydropyran-2-yl]-2-methylprop-1(E)-enyl}-5-p-methylthiophenyloxazole; (5-p-methylthiophenyl-2-(1-normon-2-yl)oxazole A)

a) p-(Methylthio)phenacyl monamide A

To a solution of monic acid A (2.1 g, 6 mmol) in dry tetrahydrofuran (35 ml) were added triethylamine (0.8 ml, 6 mmol) and isobutyl chloroformate (0.7 ml, 6 mmol). After 30 minutes p-(methylthio)phenacylammonium chloride (1.3 g, 6 mmol) and more triethylamine (0.8 ml, 6 mmol) were added. The reaction mixture was stirred for 4 h at 20° C., poured into brine and the resulting mixture extracted with ethyl acetate. The combined extracts were washed with aqueous sodium bicarbonate, dried (magnesium sulphate) and evaporated under reduced pressure. Chromatography on silicagel (20 g) eluting with 0 to 10% methanol in dichloromethane then gave the title amide as white crystals, mp 84°-87° C. (ether) (1.7 g, 56%);

$\nu_{max}$ (film) 3400, 1685, 1660, 1620, 1590 cm$^{-1}$;
$\lambda_{max}$ (EtOH) 223 nm ($\epsilon_m$ 18,100);

$\delta_H$(CD$_3$OD) 7.94 and 7.36(4H, ABq, aryl), 5.91(1H, s, H2), 4.69(2H, s, H1'), 2.54(3H, s, sMe), 2.19(3H, s, CH$_3$-15), 1.21(3H, d, CH$_3$-14), 0.97(3H, d, CH$_3$-17);

$\delta_C$(CD$_3$OD) 195.4 (C2'), 169.7 (C1), 153.0 (C3), 148.4 (C4''), 132.5 (C3'', C5''), 129.3 (C2'', C6''), 120.7 (C2), 126.1 (C1''), 120.7 (C2), 76.2 (C5), 71.6 (C13), 70.7 (C7), 70.0 (C6), 66.3 (C16), 61.3 (C11), 56.8 (C10), 46.7 (C1'), 43.6 (C4, C12), 41.5 (C8), 32.9 (C9), 40.3 (C14), 19.0 (C15), 14.6 (SMe), 12.2 (C17);

m/e (relative intensity) 507(M+, 0.7%), 489(0.8), 151(100) (Found: M+, 507.2251, $C_{26}H_{37}NO_7S$ requires 507.2290).

b) 5-p-Methylthiophenyl-2-(1-normon-2-yl) oxazole A p-(Methylthio)phenacyl monamide A (0.50 g, 1 mmol) in tetrahydrofuran (20 ml) was treated with chlorotrimethylsilane (0.8 ml, 6 mmol), triethlamine (0.9 ml, 6 mmol) and 4-N,N-dimethylaminopyridine (50 mg) for 16 h at 20° C. The mixture was then filtered and evaporated under reduced pressure and the resulting residue extracted with ether. The combined ether extracts were filtered and evaporated under reduced pressure and the resulting residue dissolved in a mixture of acetonitrile (6 ml), pyridine (6 ml), triethylamine (0.28 ml, 2 mmol) and tetrachloromethane (0.4 ml, 4 mmol). Triphenylphosphine (0.53 g, 2 mmol) was then added and the mixture stirred for 3 h at 20° C. and then poured into aqueous sodium bicarbonate, and extracted with ethyl acetate. The combined extracts were washed with brine, dried (magnesium sulphate) and evaporated under reduced pressure to give an oil, which was dissolved in dioxan (40 ml) and water (10 ml). Concentrated aqueous hydrochloric acid (12 drops) was added and after 12 minutes the solution neutralised with aqueous sodium bicarbonate and extracted with ethyl acetate. The extracts were washed with brine, dried (magnesium sulphate) and evaporated under reduced pressure to leave a brown oil which was purified by chromatography on silica gel (10 g) eluting with a gradient of 4 to 10% methanol in dichloromethane to give the oxazole as a yellow oil (314 mg, 64%).

$\nu_{max}$ (film) 3400, 1655, 1485 cm$^{-1}$;
$\lambda_{max}$ (EtOH) 223 nm ($\epsilon_m$ 15,300), 267 nm ($\epsilon_m$ 9,200), 326 nm ($\epsilon_m$ 34,100);

$\delta_H$(CDCl$_3$) 7.52 and 7.23(4H, ABq, aryl), 7.25(1H, s, oxazole H), 6.26(1H, s, H2), 3.50(3H, s, SMe), 2.30(3H, s, CH$_3$-15), 1.21(3H, d, CH$_3$-14), 0.93(3H, d, CH$_3$-17);

$\delta_C$(CDCl$_3$) 160.9 (C1), 149.7 (C3), 146.7 (C4'), 139.0 (C4''), 126.8 (C3'', C5''), 124.8 (C5'), 124.4 (C2'', C6''), 122.1 (C1''), 113.1 (C2), 75.4 (C5), 71.1 (C13), 70.4 (C7), 68.9 (C6), 65.5 (C16), 61.2 (C11), 55.6 (C10), 42.8 (C12), 42.8 (C4), 39.6 (C8), 31.7 (C9), 20.8 (C14), 19.6 (C15), 15.6 (SMe), 12.6 (C17);

m/e (relative intensity 489(M+, 17%), 245(100) (Found: M+489.2218, $C_{26}H_{35}NO_6S$ requires 489.2266).

EXAMPLE 10

2-{3-[5-(2,3-Epoxy-5-hydroxy-4-methylhexyl-3,4-dihydroxytetrahydropyran-2-yl]-2-methylprop-1(E)-enyl}-5-p-methylsulphonylphenyloxazole; (5-p-methylsulphonyl-2-(1-normon-2-yl)oxazole A)

A mixture of 5-p-methylthiophenyl-2-(1-normon-2-yl) oxazole A (0.20 g, 0.4 mmol), sodium bicarbonate (0.13 g, 1.6 mmol) and m-chloroperbenzoic acid (0.16 g, 0.8 mmol) in dichloromethane (10 ml) was stirred for 2 h at 0° C. and 1 h at 20° C., and then diluted with ethyl acetate. The solution was washed with aqueous sodium bicarbonate, dried (magnesium sulphate) and evaporated under reduced pressure. The residue was purified by chromatography (silicagel; 0 to 10% methanol in dichloromethane) to give the title compound as a yellow foam (0.11 g, 53%);

$\nu_{max}$ (film) 3450, 1655, 1605, 1305, 1150 cm$^{-1}$;

$\lambda_{max}$ (EtOH) 323 nm ($\epsilon_m$ 23,500);

$\delta_H$(CDCl$_3$) 7.92(4H, ABq, aryl), 7.57(1H, s, oxazole-H), 6.35(1H, s, H2), 3.09(3H, s, SO$_2$Me), 2.34(3H, s, CH$_3$-15), 1.20(3H, d, CH$_3$-14), 0.89(3H, d, CH$_3$-17);

$\delta_C$(CD$_3$OD:CDCl$_3$) 163.5 (C1), 150.4 (C3), 149.3 (C4'), 140.6 (C4''), 133.9 (C1''), 129.0 (C3'', C5''), 126.3 (C5'), 125.3 (C2'', C6''), 113.2 (C2), 76.1 (C5), 71.3 (C13), 70.5 (C7), 69.7 (C6), 66.2 (C16), 61.2 (C11), 56.6 (C10), 44.4 (SO$_2$Me), 43.8 (C4), 43.4 (C12), 41.2 (C8), 32.8 (C9), 20.3 (C14), 19.9 (C15), 12.2 (C17);

m/e (relative intensity) 521(M$^+$, 9%), 306(12), 277(100) (Found: M$^+$, 521.2050, C$_{26}$H$_{35}$NO$_8$S requires 521.6244.

EXAMPLE 11

5-p-Methylsulphinylphenyl-2-(1-normon-2-yl) oxazole A

A solution containing 5-p-methylthiophenyl-2-(1-normon-2-yl) oxazole A (0.20 g, 0.4 mmol), sodium bicarbonate (0.13 g, 1.6 mmol), and m-chloroperbenzoic acid (0.16 g, 0.8 mmol) in dichloromethane (5 ml) was stirred at 0° C. for 2.6 h and then diluted with ethyl acetate. The solution was washed with aqueous sodium bicarbonate, dried (MgSO$_4$) and evaporated under reduced pressure. The residue was purified by chromatography (silicagel, 0 to 10% methanol in dichloromethane) to give the title compound as a yellow oil (0.08 g, 40%); $\nu_{max}$ 3400, 1655, 1605, 1045 cm$^{-1}$; $\lambda_{max}$ (EtOH) 321 nm ($\epsilon_m$ 30,000); $\delta_H$ (CDCl$_3$) 7.84(4H, AA't, aryl), 7.56(1H, s, oxazole-H), 6.38(1H, s, H2), 2.80(3H, s, SOMe), 2.34(3H, s, CH$_3$-15), 1.21(3H, d, CH$_3$-14), 0.93(3H, d, CH$_3$-17); m/e (relative intensity) 505(M$^+$, 17%), 261(96), 244(100) (Found: M$^+$, 505.2148, C$_{26}$H$_{35}$NO$_7$S requires 505.2132).

EXAMPLE 12

Sodium 8-[2-(1-normon-2-yl)-5-oxazolyl]-octanoate A

A mixture of 5-(7-methoxycarbonylheptyl)-2-(1-normon-2-yl) oxazole A (64 mg, 0.12 mmol), DMF (1.8 ml), bakers' yeast (2.5 g) and 0.2M pH 7 phosphate buffer (30 ml) was vigorously stirred for 18 h at 20° C. and then filtered through celite and evaporated under reduced pressure. The resulting residue was resuspended in water and the pH adjusted to 4. The resulting residue was extracted with ethyl acetate, which was dried (MgSO$_4$) and evaporated under reduced pressure. The residue was purified by preparative hplc (75% 0.05M aqueous ammonium acetate: 25% THF, C-8 reverse phase 250×10 mm column) to give the title sodium salt as a colourless oil (9 mg, 14%); $\delta_H$(CD$_3$OD) 6.79(1H, s, oxazole-H4), 6.13(1H, s, H2), 2.68(2H, t, oxazole-CH$_2$), 2.14(2H, t, CH$_2$CO$_2^-$), 2.19(3H, s, CH$_3$-15), 1.21(3H, d, CH$_3$-14), 0.95(3H, d, CH$_3$-17).

EXAMPLE 13

5-p-Hydroxymethylphenyl-2-(1-normon-2-yl) oxazole A

A solution of p-hydroxymethylphenacyl monamide A (0.30 g, 0.6 mmol) in THF (20 ml) was treated with chlorotrimethylsilane (0.39 ml, 3 mmol), triethylamine (0.42 ml, 3 mmol) and 4-N,N-dimethylaminopyridine (5 mg) for 2 h at 20° C. The mixture was then filtered, the filtrate was evaporated under reduced pressure and the resulting residue extracted with ether. The combined ether extracts were filtered, the filtrate was evaporated under reduced pressure and the resulting residue dissolved in a mixture of acetonitrile (3 ml), pyridine (3 ml), triethylamine (0.18 ml, 1.2 mmol) and tetrachloromethane (0.24 ml, 2.4 mmol). Triphenylphosphine (0.33 g, 1.2 mmol) was then added and the mixture allowed to stand at 60° C. for 1 h.

The reaction mixture was poured into aqueous sodium bicarbonate, and extracted with ethyl acetate. The combined extracts were washed with brine, dried (MgSO$_4$) and evaporated under reduced pressure to give an oil, which was dissolved in dioxan (20 ml) and water (5 ml). Concentrated aqueous hydrochloric acid (6 drops) was added and after 12 min the solution neutralised with aqueous sodium bicarbonate and extracted with ethyl acetate. The extracts were washed with brine, dried (Mg SO$_4$) and evaporated under reduced pressure to leave a brown oil which was purified by chromatography on silica gel (10 g) eluting with a gradient of 4 to 10% methanol in dichloromethane to give the title oxazole as pale yellow needles, mp 128°–130° (CH$_2$Cl$_2$) (0.16 g, 56%); $\nu_{max}$ 3400, 1655, 1530 cm$^{-1}$; $\lambda_{max}$ (EtOH) 306 nm ($\epsilon_m$ 33,200); $\delta_H$ (CDCl$_3$) 7.67 and 7.43 (4H, ABq, aryl), 7.35(1H, s, oxazole-H), 6.29(1H, s, H2), 4.71(2H, d, ArCH$_2$), 2.33(3H, s, CH$_3$-15), 1.24 (3H, d, CH$_3$-14), 0.95(3H, d, CH$_3$-17); $\delta_C$(CDCl$_3$) 161.9 (C1), 150.9 (C5'), 148.2 (C3), 142.5 (C4''), 128.0 (C3'', C5''), 127.1 (C1''), 124.6 (C2'', C6''), 122.4 (C4'), 113.3 (C2), 75.9 (C5), 71.0 (C13), 70.4 (C7), 69.4 (C9), 66.0 (C16), 64.5 (CH$_2$Ar), 61.1 (C11), 56.4 (C10), 43.5 (C12), 43.1 (C4), 40.7 (C8), 32.5 (C9), 20.2 (C14), 19.7 (C15), 12.2 (C17); m/e (relative intensity) 473(M$^+$, 8%), 229(100) (Found: M$^+$, 473.2379, C$_{26}$H$_{35}$NO$_7$ requires 473.2411).

EXAMPLE 14

5-Methyl-2-(1-normon-2-yl) oxazole A

A solution containing glycine (7.5 g, 0.10 mol), pyridine (50 ml, 0.60 mol) and acetic anhydride (110 ml, 1.17 mol) was boiled under reflux for 6 h and then evaporated under reduced pressure. Distillation of the residue gave diacetylaminoacetone as a yellow oil (10.0 g, 64%); b.p. 100°–120° C./1 mm; $\delta_H$ (CDCl$_3$) 4.5(2H, s, CH$_2$), 2.3(6H, s, Ac-N), 2.2(3H, s, Ac-C).

Diacetylaminoacetone (5 g) and phosphoryl chloride (10 ml) were heated together at reflux for 1 h. The mixture was cooled and decomposed with aqueous sodium bicarbonate. This was extracted with ether and the combined extracts carefully concentrated under reduced pressure. Distillation of the residue gave 2,5-dimethyloxazole as a mobile colourless liquid (1.0 g, 32%); b.p. ~120° C./760 mm; $\delta_H$ (CDCl$_3$) 6.6(1H, s, H-4), 2.4, 2.25(6H, 2s, Me$_2$).

To a solution of 3-[5-(2,3-epoxy-5-hydroxy-4-methylhexyl)-3,4-dihydroxytetrahydropyran-2-yl]propan-2-one, (2.0 mmol) and triethylamine (0.86 ml, 6.20 mmol) in dry THF (25 ml) was added trimethylsilyl chloride (0.78 ml, 6.20 mmol) and a catalytic amount of 4-(N,N-dimethylamino)-pyridine. After stirring at room temperature for 2 h the triethylamine hydrochloride was filtered off and the solution concentrated under reduced pressure. The resultant oil was taken up in ether then filtered and concentrated under reduced pressure again. This oil (the "protected ketone") was taken up in dry THF (15 ml) ready for the next stage of the reaction.

A solution of 2,5-dimethyloxazole (0.21 g, 2.20 mmol) and butyl lithium (2.20 mmol) in dry THF at −78° C. was stirred for 10–15 minutes. To the metalated species produced was added trimethylsilyl chloride (0.28 ml, 2.20 mmol) and this mixture stirred at −78° C. for 45 minutes, followed by a further 45 minutes at −20° C. to −25° C. The resultant solution was cooled to −78° C. and a further equivalent of butyl lithium (2.04 mmol) added. Stirring was continued for 45 minutes before adding the protected ketone, vide supra, and allowing to warm to room temperature. The mixture was quenched with ammonium chloride solution, extracted with ethyl acetate (3×50 ml) and the extract dried ($MgSO_4$). Solvent removal under reduced pressure gave the protected oxazole which was taken up in THF/water (4:1, 50 ml) and treated with concentrated hydrochloric acid (10 drops) for 5 min, then finally quenched with sodium bicarbonate solution. Extraction with ethyl acetate, drying ($MgSO_4$) and solvent removal under reduced pressure gave the triol which was further purified by column chromatography on silicagel (20 g) using dichloromethane/methanol (0 to 6%) as eluant. This gave the title oxazole as a colourless oil (0.20 g, 26%); $\nu_{max}$ (film) 3400, 1655, 1610 $cm^{-1}$; $\lambda_{max}$ (EtOH) 264 nm ($\epsilon_m$ 15,000); $\delta_H$ ($CDCl_3$) 6.73(1H, s, H4'), 6.16(1H, s, H2), 2.33(3H, s, Het-$CH_3$), 2.24(3H, s, $CH_3$-15), 1.23(3H, d, $CH_3$-14), 0.94(3H, d, $CH_3$-17); $\delta_C$ ($CDCl_3$) 160.7 (C1), 147.4 (Het-C5), 145.3 (C3), 123.1 (Het-C4), 113.2 (C2), 75.4 (C5), 71.1 (C13), 70.4 (C7), 68.9 (C6), 65.4 (C16), 61.2 (C11), 55.6 (C10), 42.8 (C4), 42.6 (C12), 39.5 (C8), 31.8 (C9), 20.7 (C14), 19.3 (C15), 12.6 (C17), 10.8 (Het-Me); m/e (relative intensity) 381($M^+$, 6%), 176(12), 137(100) (Found $M^+$=381.2133. $C_{20}H_{31}NO_6$ requires 381.2116).

EXAMPLE 15

5-p-Formylphenyl-2-(1-normon-2-yl) oxazole A

A mixture of 5-p-hydroxymethylphenyl-2-(1-normon-2-yl) oxazole A (100 mg), activated manganese dioxide (500 mg) and acetonitrile (40 ml) was stirred vigorously for 1.5 h and then filtered. The filtrate was evaporated under reduced pressure and the resulting residue chromatographed quickly (10 g silica, 0 to 10% methanol in dichloromethane) to give the title aldehyde as a yellow oil (21 mg, 21%); $\nu_{max}$ (film) 3400, 1695, 1665, 1605 $cm^{-1}$; $\nu_{max}$ (EtOH) 337 nm; $\delta_H$ ($CDCl_3$) 10.01(1H, s, CHO), 7.94, 7.79(4H, ABq, aryl), 7.53(1H, s, Het-H), 6.32(1H, s, H2), 2.36(3H, s, $CH_3$-15), 1.25(3H, d, $CH_3$-14), 0.94(3H, d, $CH_3$-17); $\delta_C$ ($CDCl_3$) 191.2 (CHO), 162.3 (C1), 148.5 (C3), 148.3 (Het-C4), 135.6 (C'4), 133.5 (C1'), 130.4 (C3', C5'), 125.6 (Het-C5), 124.1 (C2', C6'), 113.0 (C2), 75.3 (C5), 71.3 (C13), 70.5 (C7), 69.0 (C6), 65.5 (C16), 61.2 (C11), 55.5 (C10), 43.0 (C4), 42.8 (C12), 39.7 (C8), 31.8 (C9), 20.8 (C14), 19.7 (C15), 12.7 (C17); m/e (relative intensity) 471($M^+$, 9%), 227(100) (Found: $M^+$=471.2249. $C_{26}H_{33}NO_7$ requires 471.2243).

EXAMPLE 16

5-p-Methoxycarbonylphenyl-2-(1-normon-2-yl) oxazole A

A mixture of 5-p-hydroxymethylphenyl-2-(1-normon-2-yl) oxazole A (50 mg, 0.1 mmol), sodium cyanide (25 mg, 0.5 mmol), acetic acid (18 μl, 0.3 mmol), activated manganese dioxide (500 mg), and methanol (10 ml) was stirred for 6 h at 20° C. More manganese dioxide (500 mg) was then added and the mixture stirred for another 2 h at 20° C. and then filtered. The filtrate was evaporated under reduced pressure and the resulting residue purified by chromatography to give the title methyl ester as a yellow oil (12–15 mg, 23–30%); $\nu_{max}$ ($CHCl_3$) 3400, 1715, 1655, 1610 $cm^{-1}$; $\lambda_{max}$ (EtOH) 328 nm; $\delta_H$ ($CDCl_3$) 8.07 and 7.69(4H, 2d, aryl), 7.47(1H, s, Het-H), 6.30(1H, s, H2), 2.33(3H, s, $CH_3$-15), 1.24(3H, d, $CH_3$-14), 0.95(3H, d, $CH_3$-14); $\delta_C$ ($CDCl_3$) 166.6 ($CO_2Me$), 162.0 (C1), 149.0 (C3), 147.9 (Het-C4), 132.2 (C1'), 130.4 (C3'), 129.5 (C4'), 124.8 (Het-C5), 123.8 (C2'), 113.1 (C2), 75.4 (C5), 71.4 (C13), 70.6 (C7), 69.1 (C6), 65.6 (C16), 61.3 (C11), 55.6 (C10), 55.2 ($CO_2Me$), 43.0 (C12), 42.9 (C4), 39.7 (C8), 31.8 (C9), 20.9 (C14), 19.8 (C15), 12.7 (C17); m/e (relative intensity) 501($M^+$, 8%), 257(100) (Found: $M^+$=501.2362. $C_{27}H_{35}NO_8$ requires 501.2363).

EXAMPLE 17

Sodium 4-[2-(1-normon-2-yl)-5-oxazolyl] benzoate A 5-p-Methoxycarbonylphenyl-2-1-normon-2-yloxazole A (50 mg, 0.1 mmol) was dissolved in excess trimethylorthoformate (2 ml). p-Toluenesulphonic acid (ca. 5 mg) was added, and the mixture stirred 25 min at 20° C. and then evaporated under reduced pressure. The residue was treated with sodium hydroxide (40 mg, 1.0 mmol), water (10 ml) and methanol (10 ml) at 20° C. for 18 h. The mixture was then acidified to pH2 for 15 min, and then adjusted to pH9.5 for 3 h, and then to pH4. Extraction with ethyl acetate and evaporation of the extracts under reduced pressure then gave the free acid, which was immediately converted to the sodium salt with sodium bicarbonate in aqueous methanol. The sodium salt was obtained as a gummy solid (23 mg, 45%); $\nu_{max}$ (film) 3400, 1660, 1595, 1540, 1385 $cm^{-1}$; $\delta_H$ ($CD_3OD$) 8.03 and 7.68(4H, ABq, aryl), 7.52(1H, s, Het-H), 6.25(1H, s, H2), 2.30(3H, s, $CH_3$-15), 1.19(3h, d, $CH_3$-14), 0.94(3H, d, $CH_3$-17).

EXAMPLE 18

5-p-Bromophenyl-2-(1-normon-2-yl) oxazole A

To 1,4'-dibromoacetophenone (27.8 g, 100 mmol) in dichloromethane (200 ml) was added hexamine (14.0 g, 100 mmol). The precipitated salt was collected and dissolved in a mixture of concentrated hydrochloric acid (33 ml) and ethanol (67 ml). After 16 h at 20° C. the precipitate was collected and recrystallised from dilute hydrochloric acid to give p-bromophenacylammonium chloride as white platelets (9.0 g, 36%); m.p. 287° C. (dec.); $\delta_H$(dmso-$d_6$) 8.6(3H, bs,—$NH_3^+$), 7.8(4H, ABq, aryl).

To a solution of monic acid A (1.72 g, 5 mmol) in dry THF (50 ml) were added triethylamine (0.69, 5 mmol) and isobutyl chloroformate (0.65 ml, 5 mmol) and after 10 min, p-bromophenacylammonium chloride (1.26 g, 5 mmol) and more triethylamine (0.69 ml, 5 mmol). After 3 h at 20° C. the solution was poured into water and extracted with ethyl acetate. Drying ($MgSO_4$) and evaporation of the extract under reduced pressure then gave crude p-bromophenacyl monamide A as a gummy white solid (1.51 g, 59%); $\nu_{max}$ 3400, 2985, 1695, 1660, 1635. 1590 $cm^{-1}$; $\delta_H$ ($CD_3OD$) 7.72(4H, ABq, aryl), 5.88(1H, s, H2), 4.70(2H, s, H1'), 2.12(3H, s, $CH_3$-15), 1.14(3H, d, $CH_3$-14), 0.90(3H, d, $CH_3$-17).

p-Bromophenacyl monamide A (1.35 g, 2.5 mmol) in THF (50 ml) was treated with chlorotrimethylsilane (1.0 ml) 8 mmol), triethylamine (1.1 ml, 8 mmol) and 4-N,N-dimethylaminopyridine (50 mg) for 2 h at 20° C. The mixture was then filtered and evaporated under reduced pressure and the resulting residue extracted with ether. The combined ether extracts were filtered and evaporated under reduced pressure and the resulting residue dissolved in a mixture of acetonitrile (10 ml), pyridine (10 ml), triethylamine (0.7 ml, 5 mmol) and tetrachloromethane (1.0 ml, 10 mmol). Triphenylphosphine (1.3 g, 5 mmol) was then added and the mixture allowed to stand at 20° C. for 3 h.

The reaction mixture was poured into aqueous sodium bicarbonate, and extracted with ethyl acetate. The combined extracts were washed with brine, dried (MgSO$_4$) and evaporated under reduced pressure to give an oil, which was dissolved in THF (80 ml) and water (20 ml). Concentrated aqueous hydrochloric acid (25 drops) was added and after 12 min the solution neutralised with aqueous sodium bicarbonate and extracted with ethyl acetate. The extracts were washed with brine, dried (MgSO$_4$) and evaporated under reduced pressure to leave a brown oil which was purified by chromatography on silica gel (50 g) eluting with a gradient of 4 to 10% methanol in dichloromethane to give the title oxazole as a yellow foam (0.30 g, 23%); $\nu_{max}$ (film) 3400, 1655, 1480, 730 cm$^{-1}$; $\lambda_{max}$ (EtOH) 306 nm ($\epsilon_m$ 26,300); $\delta_H$ 7.49(4H, ABq, aryl), 7.34(1H, s, het-H), 6.28(1H, s, H2), 2.31(3H, s, CH$_3$-15), 1.21(3H, d, CH$_3$-14), 0.93(3H, d, CH$_3$-17); $\delta_c$ (CDCl$_3$) 161.3 (C1), 148.9 (C3), 147.4 (C4'), 132.1 (C2''), 126.9 (C5'), 125.4 (C3''), 123.0 (C4''), 122.0 (C1''), 112.9 (C2), 75.2 (C5), 71.1 (C13), 70.4 (C7), 68.9 (C6), 65.4 (C16), 61.2 (C11), 55.5 (C10), 42.8 (C12), 42.7 (C4), 39.5 (C8), 31.7 (C9), 20.8 (C14), 19.6 (C15), 12.6 (C17); m/e (relative intensity) 521, 523(4%,1:1, M$^+$), 277,279(72,58), 41(100) (Found: M$^+$521.1428, C$_{25}$H$_{32}$NO$_6$$^{79}$Br requires 521.1410).

EXAMPLE 19

5-(8-Hydroxyoctyl)-2-(1-normon-2-yl) oxazole A

9-Hydroxynonanoic acid (8.7 g, 50 mmol) in pyridine (8.1 ml, 100 mmol) was treated with acetic anhydride (4.7 ml, 50 mmol) at below 20° C. for 2 h. The mixture was poured onto ice and acidified. Two ether extractions gave 9-acetoxynonanoic acid as a colourless oil (10.8 g, 100%); $\delta_H$ (CDCl$_3$) 10.0(1H, s, CO$_2$H), 4.0(2H, t, H9), 2.3(2H, m, H2), 2.0(3H, s, OAC), 1.1–1.8(12H, m, H3–H8).

9-Acetoxynonanoic acid (10.8 g, 50 mmol) was added to thionyl chloride (7.2 ml, 100 mmol) at reflux. After 30 min at reflux distillation at reduced pressure gave first excess thionyl chloride and then 9-acetoxynonanoyl chloride as a yellow oil (4.0 g, 32%); $\delta_H$ (CDCl$_3$) 4.0(2H, t, H9), 2.9(2H, t, H2), 2.0(3H, s, OAc) 1.1–1.8(12H, m, H3–H8).

9-Acetoxynonanoyl chloride (4.0 g, 17 mmol) was slowly added to a solution of diazomethane (40 mmol) in ether (100 ml) at 0° C. After 1 h at 0° C. concentrated hydrobromic acid (20 ml) was added. After 1 h at 20° C. the ether was separated, dried (MgSO$_4$), and evaporated under reduced pressure to give 10-bromo-9-oxodecyl acetate as a yellow oil (4.4 g 88%); $\delta_H$ (CDCl$_3$) 4.0(2H, t, O), 3.8(2H, s, CH$_2$Br), 2.6(2H, t, CH$_2$CO), 2.0(3H, s, OAC), 1.1–1.8(12H, m, (CH$_2$)$_6$).

10-Bromo-9-oxodecyl acetate (2.2 g, 7.5 mmol) and hexamine (1.4 g, 10 mmol) in chloroform (50 ml) were stirred for 16 h at 20° C.; and then the solution was evaporated under reduced pressure. The residue was dissolved in a mixture of concentrated hydrochloric acid (10 ml) and ethanol (30 ml). After 16 h at 20° C. the solution was evaporated under reduced pressure and the residue extracted with ethanol. Evaporation of the ethanol under reduced pressure then gave 10-hydroxy-2-oxodecylammonium chloride as a brown powder which also contained ammonium chloride (2.8 g); $\delta_H$ (D$_2$O) 3.5(2H, t, H10), 2.6(2H, t, H3), 1.1–1.8(12H, m, H4–H9).

10-Hydroxy-2-oxodecylammonium chloride (2.8 g, crude) in methanol (20 ml) was added to isobutyloxycarbonyl monate A (10 mmol, prepared from monic acid (10 mmol), isobutyl chloroformate (10 mmol) and triethylamine (10 mmol)) in THF (50 ml). After 2 h at 20° C. the solution was partitioned between aqueous sodium bicarbonate and ethyl acetate. The organic layer was dried (MgSO$_4$) and evaporated under reduced pressure and the resulting residue purified by chromatography (20 g silicagel, 0 to 15% methanol in dichloromethane) to give 10-hydroxy-2-oxodecyl monamide A as a colourless oil (0.8 g, 21%); $\nu_{max}$ (film) 3400, 2960, 1720, 1660, 1630 cm$^{-1}$; $\delta_H$ (CD$_3$OD) 5.75(1H, s, H2), 4.71(2H, s, H1'), 2.08(3H, s, CH$_3$-15), 1.3(12H, m, H4'–H9'), 1.20(3H, d, CH$_3$-14), 0.89(3H, d, CH$_3$-17).

10-Hydroxy-2-oxodecyl monamide A (0.51 g, 1 mmol) in THF (20 ml) was treated with chlorotrimethylsilane (0.63 ml, 5 mmol), triethylamine (0.70 ml, 5 mmol) and 4-N,N-dimethylaminopyridine (5 mg) for 2 h at 20° C. The mixture was then filtered and evaporated under reduced pressure, and the resulting residue extracted with ether. The combined ether extracts were filtered and evaporated under reduced pressure and the resulting residue dissolved in a mixture of acetonitrile (3 ml), pyridine (3 ml), triethylamine (0.28 ml, 2 mmol) and tetrachloromethane (0.39 ml, 4 mmol). Triphenylphosphine (0.52 g, 2 mmol) was then added and the mixture allowed to stand at 20° C. for 3 h.

The reaction mixture was poured into aqueous sodium bicarbonate, and extracted with ethyl:acetate. The combined extracts were washed with brine, dried (MgSO$_4$) and evaporated under reduced pressure to give an oil, which was dissolved in THF (20 ml) and water (5 ml). Concentrated aqueous hydrochloric acid (6 drops) was added and after 12 min the solution neutralised with aqueous sodium bicarbonate and extracted with ethyl acetate. The extracts were washed with brine, dried (MgSO$_4$) and evaporated on silica gel (10 g) eluting with a gradient of 4 to 10% methanol in dichloromethane to give the title oxazole as a colourless oil (0.15 g, 27%); $\nu_{max}$ (film) 3400, 2960, 1655, 1605 cm$^{-1}$; $\delta_H$ (CDCl$_3$) 6.81(1H, s, het-H), 6.16(1H, s, H2), 3.62(2H, t, H8'), 2.64(2H, t, H1'), 2.21(3H, s, CH$_3$-15), 1.3(12H, m, H2'–H7'), 1.22(3H, d, CH$_3$-14), 0.94(3H, d, CH$_3$-17); $\delta_C$ (CDCl$_3$) 160.6 (C1), 151.7 (C4'), 145.3 (C3), 122.6 (C5'), 113.3 (C2), 75.3 (C5), 71.1 (C13), 70.4 (C7), 68.9 (C6), 65.5 (C16), 62.8 (C8''), 61.2 (C11) 55.6 (C10), 42.7 (C4, C12), 39.5 (C8), 32.7 (C1''), 31.8 (C9), 29.2, 29.1, 28.9, 27.5, 25.7, 25.5 (C2''–7''), 20.8 (C14), 19.3 (C15), 12.6 (C17); m/e (relative intensity) 495(M$^+$, 9%), 251(100) (Found: M$^+$495.3200, C$_{27}$H$_{45}$NO$_7$ requires 495.3196.

EXAMPLE 20

5-(3-Thienyl)-2-(1-normon-2-yl) oxazole A

3-Acetylthiophene (6.3 g, 50 mmol) was dissolved in anhydrous ether (100 ml) and aluminium chloride (catalytic amount) added. Bromine (2.55 ml, 50 mmol) was added dropwise and then stirred for 10 min. The ether was removed under reduced pressure and the residue washed with water. The crude product was recrystallised from petroleum-ether (60°–80° C.) to yield 3-bromoacetylthiophene m.p. 54°–56° C. (8.76 g, 85%), $\delta_H$ (CDCl$_3$) 8.15(1H, dd, H2), 7.55(1H, dd, H4'), 7.35(1H, dd, H5').

3-Bromoacetylthiophene (6.15 g, 30 mmol) was dissolved in dichloromethane (200 ml) and hexamethylenehetramine (4.2 g, 30 mmol) added and stirred for 1 h. The reaction was filtered and washed with dichloromethane to yield the hexamine salt as a pale pink solid m.p. 122°–125° C. (8.06 g, 78%). The hexamine salt (7.6 g, 22 mmol) was stirred in ethanol (30 ml) and hydrochloric acid (10 ml) for 1 h and after standing overnight the mixture was filtered and the filtrate evaporated under reduced pressure. The resulting residue was taken up in methanol, filtered, and the filtrate evaporated under reduced pressure. The residue was recrystallized from isopropanol containing a few drops of dilute hydrochloric acid to yield 3-(2-amino-1-oxoethyl)thiophene hydrochloride (2.92 g, 75%) $\delta_H$ (CD$_3$OD) 8.55(1H, s, H2'), 7.60(2H, s, H4',5'), 4.52(2H, s, CH$_2$).

The isobutoxyformic mixed anhydride of monic acid A was prepared on a 10 mmol scale by mixing monic acid A (3.44 g, 10 mmol), triethylamine (1.5 ml, 11 mmol), and isobutylchloroformate (1.44 ml, 11 mmol) for 1 h at 0° C. 3-(2-amino-1-oxoethyl)thiophene hydrochloride (1.77 g, 10 mmol) and triethylamine (4.5 ml) added and stirred for 4 h. The reaction mixture was then poured into brine, extracted with ethyl acetate, the extract was dried (MgSO$_4$), and evaporated under reduced pressure. The residual orange oil was purified by chromatography on silica gel (15 g) eluting with a gradient of 0 to 4% methanol in dichloromethane to yield N-[2-oxo-2-(3-thienyl)ethyl] monamide A as a pale yellow oil (691 mg, 15%); $\nu_{max}$ (film) 3400, 1680, 1660, 1630, 1510 cm$^{-1}$; $\lambda_{max}$ (EtOH) 216 nm (Em 23,622), 248 nm (Em 15,878); $\delta_H$ (CD$_3$OD) 8.42(1H, dd, H2"), 7.59(1H, dd, H4"), 7.51(1H, dd, H5"), 5.89(1H, s, H2), 4.63(2H, s, CH$_2$1'), 2.18(3H, s, CH$_3$-15), 1.20(3H, d, CH$_3$-14), 0.95(3H, d, CH$_3$-17); $\delta_c$ (CD$_3$OD) 191.2 (C2'), 169.8 (C1), 153.1 (C3), 141.1 (C3"), 134.1, 127.9, 127.5 (C2",4",5"), 120.8 (C2), 76.3 (C5), 71.6 (C13), 70.8 (C7), 70.1 (C6), 66.3 (C16), 61.3 (C11), 56.9 (C10), 47.6 (C1'), 43.7, 43.2 (C4,12), 41.6 (C8), 33.0 (C9), 20.4 (C14), 19.0 (C15), 12.2 (C17).

N-[2-Oxo-2-(3-thienyl)ethyl] monamide A (0.46 g, 1 mmol) in dry THF (25 ml) was treated with chlorotrimethylsilane (0.55 ml, 4.3 mmol), triethylamine (0.6 ml, 4.3 mmol) and 4-N,N-dimethylaminopyridine (catalytic amount) for 2½ h at 20° C. The mixture was then filtered and evaporated under reduced pressure. The residue was dissolved in a mixture of acetonitrile (5 ml) and pyridine (5 ml). Triethylamine (0.3 ml, 2 mmol), carbon tetrachloride (0.4 ml, 4 mmol), and triphenylphosphine (0.52 g 2 mmol) were then added and the mixture heated at 60° C. for 2 h. The black solution was then evaporated under reduced pressure. The resulting residue was taken up in ethyl acetate, washed with aqueous sodium bicarbonate and brine, dried (MgSO$_4$), and evaporated under reduced pressure. The residual oil was dissolved in THF (40 ml) and water (10 ml). Concentrated hydrochloric acid (15 drops) was added and after 6 min the solution was neutralised with aqueous sodium bicarbonate. The solution was extracted with ethyl acetate, washed with brine, the extract was dried (MgSO$_4$), and evaporated under reduced pressure. The residue was purified by chromatography on silica gel (7 g) eluting with a gradient of 0 to 4% methanol in dichloromethane to give the title oxazole as a yellow oil (0.178 g, 40%); $\nu_{max}$ (film) 3400, 1650, 1610, 1540, 1520, 1490 cm$^{-1}$; $\lambda_{max}$ (EtOH) 224 nm. (Em 11, 999), 300 nm (Em 19,837); $\delta_H$ (CDCl$_3$) 7.60(1H, dd, H2"), 7.37(1H, dd, H5"), 7.29(1H, dd, H4"), 7.18(1H, s, H4'), 6.26(1H, s, H2), 2.30(3H, s, CH$_3$-15), 1.21(3H, d, CH$_3$-14), 0.93(3H, d, CH$_3$-17); $\delta_c$ (CDCl$_3$) 160.6 (C1), 146.9, 146.7 (C3, 5'), 129.4 (C4'), 126.8, 124.5, 122.2, 120.4 (C2", 3", 4", 5"), 113.2 (C2), 75.5 (C5), 71.3 (C13), 70.6 (C7), 69.1 (C6), 65.6 (C16), 61.3 (C11), 55.6 (C10), 42.9 (C4, 12), 39.7 (C8), 319. (C9), 20.9 (C14), 19.7 (C15), 12.7 (C17); m/e (relative intensity) 449(M+, 5%), 227(12), 205(66), 69(75), 43(100) (Found: 449.1869, C$_{23}$H$_{31}$NO$_6$S requires 449.1872).

EXAMPLE 21

5-p-Cyanophenyl-2-(1-normon-2-yl) oxazole A

4-Acetylbenzonitrile (14.5 g, 100 mmol) was dissolved in anhydrous ether (150 ml). Aluminium chloride (catalytic amount) was added to the solution. Bromine (5.1 ml, 100 mmol) was added dropwise at room temperature and the solution stirred for ½ h. A precipitate formed and was collected and dried to yield p-cyanophenacyl bromide, m.p. 85°–86° C. (19.34 g, 86%); $\delta_H$ (CDCl$_3$) 7.80 and 8.10(4H, ABq, aryl), 4.45(2H, s, CH$_2$).

p-Cyanophenacyl bromide (13.44 g, 60 mmol) was dissolved in methylene chloride (400 ml) and hexamethylenetetramine (8.4 g, 60 mmol) added and the reaction stirred for 3 H. The precipitated solid was collected and dried to yield the hexamine salt, m.p. 146°–148° C. (21 g, 96%). The hexamine salt (14 g) was added to a mixture of methanol (42 ml) and concentrated hydrochloric acid (14 ml) and left standing for 3 days. Isopropanol added to the residue, and the solid collected and dried to yield impure p-cyanophenacyl ammonium chloride.

Monic acid A (3.44 g, 10 mmol) was dissolved in dry THF (100 ml) and cooled to 0° C. Triethylamine (1.5 ml, 11 mmol) and isobutylchloroformate (1.44 ml, 11 mmol) were added and stirred ½ h. Impure p-cyanophenacyl ammonium chloride (1.96 g, 10 mmol) and triethylamine (1.5 ml, 11 mmol) were added and the mixture stirred for 2 h. Further p-cyanophenacyl ammonium chloride (1 g, 5 mmol) and triethylamine (0.8 ml, 5 mmol) were then added and stirred for ½ h. The reaction was then poured into brine and extracted with ethyl acetate and the organic layer was separated, washed with aqueous sodium bicarbonate, dried (MgSO$_4$), and evaporated under reduced pressure. The residual oil was purified by chromatography on silica gel (25 g) eluting with a gradient of 0 to 4% methanol in dichloromethane to give N-(p-cyanophenacyl) monamide A as a pale yellow foam (1.35 g, 28%); $\nu_{max}$ (film) 3400, 2230, 1700, 1660, 1640 cm$^{-1}$; $\lambda_{max}$ (EtOH) 204 nm (Em 26,197), 246 nm (Em 25,414); $\delta_H$ (CD$_3$OD) 8.15 and 7.90(4H, ABq, aryl), 5.90(1H, s, H2), 4.72(2H, s, CH$_2$-1'), 2.17(3H, s, CH$_3$-15), 1.20(3H, d, CH$_3$-14), 0.95(3H, d, CH$_3$-17); $\delta_c$ (CD$_3$OD) 195.7 (C2'), 169.8 (C1), 153.4 (C3), 139.7 (C1"), 133.8, 129.6 (C2", 3", 5", 6"), 120.6 (C2), 118.9 (CN), 117.6 (C4"), 76.3 (C5), 71.6 (C13), 70.7 (C7), 70.1 (C6), 66.3 (C16), 61.3 (C11), 56.9 (C10), 47.3 (C1'), 43.7 (C4, 12), 41.6 (C8), 33.0 (C9), 20.4 (C14), 19.0 (C15), 12.2 (C17); m/e (relative intensity)

486 (M+, 2%), 327(11), 242(46), 227(48), 111(100) (Found: 486.2334, $C_{26}H_{34}N_2O_7$ requires 486.2336).

N-(p-Cyanophenacyl) monamide A (0.49 g, 1 mmol) in dry THF (30 ml) was treated with chlorotrimethylsilane (0.55 ml, 4.3 mmol), triethylamine (0.6 ml, 4.3 mmol) and 4-N,N-dimethylaminopyridine (catalytic amount) for 1½ h and 20° C. The mixture was then filtered and evaporated under reduced pressure. The residue was dissolved in a mixture of acetonitrile (2.5 ml), pyridine (2.5 ml), triethylamine (0.3 ml, 2 mmol) and carbon tetrachloride (2.5 ml), triethylamine (0.3 ml, 2 mmol) and carbon tetrachloride (0.4 ml, 4 mmol) was treated with triphenylphosphine (0.52 g, 2 mmol) and heated at 60° C. for 1½ h. The black solution was then evaporated under reduced pressure and the residue taken up in ethyl acetate. The extracts were washed with aqueous sodium bicarbonate and brine, dried ($MgSO_4$), evaporated under reduced pressure and the resulting residue dissolved in THF (40 ml) and water (10 ml). Concentrated aqueous hydrochloric acid (15 drops) was added and after 5 mins the solution was neutralised with aqueous sodium bicarbonate. The solution was extracted with ethyl acetate and the extracts washed with brine, dried ($MgSO_4$) and evaporated under reduced pressure and the residual oil purified by chromatography (7 g silica gel, 0 to 4% methanol in dichloromethane) to yield the title oxazole as a pale yellow oil (0.122 g, 26%); $\lambda_{max}$ (film) 3440, 2230, 1650, 1610, 1530 cm$^{-1}$; $\lambda_{max}$(EtOH) 231 nm (Em 14,409), 326 nm (Em 22,655); $\delta_H$(CDCl$_3$) 7.71(4H, s, aryl), 7.50(1H, s, H4'), 6.30(1H, s, H2), 2.35(3H, s, CH$_3$-15), 1.23(3H, d, CH$_3$-14), 0.95(3H, d, CH$_3$-17); $\delta_c$ (CDCl$_3$) 162.4 (C1), 148.6, 148.0 (C3, 5'), 132.8 (C3", 5"), 132.2 (C1"), 125.7 (C4'), 124.3 (C2", 6"), 118.5 (C7"), 13.0 (C2), 111.4 (C4"), 75.4 (C5), 71.3 (C13), 70.6 (C7), 69.2 (C6), 65.5 (C16), 61.3 (C11), 55.6 (C10), 43.0, 42.9 (C4, 12) 39.8 (C8), 31.8 (C9), 20.9 (C14), 19.8 (C15), 12.7 (C17); m/e (relative intensity) 468 (M+, 8%), 277(9), 224(100) (Found: 468.2249, $C_{26}H_{32}N_2O_6$ requires 468.2260).

EXAMPLE 22

5-m-Methylthiophenyl-2-(1-normon-2-yl)oxazole A m-Acetylthiophenol (76 g, 50 mmol), sodium hydroxide (2.0 g, 50 mmol) and ethanol (50 ml) were stirred at room temperature for 1 h. Iodomethane (3.2 ml, 50 mmol) was added and stirred for 2 h then the solution was evaporated under reduced pressure and the residue taken up in ethyl acetate. This solution was washed with aqueous sodium bicarbonate, brine, then dried ($MgSO_4$), and evaporated under reduced pressure to yield m-Methylthioacetophenone (7.21 g, 87%); $\delta H$(CDCl$_3$) 7.05-7.85(4H, m, aryl), 2.55(3H,S,COCH$_3$), 2.45(3H,S,SCH$_3$).

m-Methylthioacetophenone (7.14 g, 43 mmol) was dissolved in chloroform (100 ml). Aluminium chloride (catalytic amount) and bromine (2.2 ml, 43 mmol) were added and stirred for 1 h. The reaction was quenched with aqueous sodium chloride-sodium bicarbonate and the organic layer separated, dried ($MgSO_4$) and evaporated under reduced pressure. The residue was taken up in ethyl acetate, washed with aqueous sodium bicarbonate, then brine, dried ($MgSO_4$) and evaporated under reduced pressure to yield m-Methylthiophenacyl bromide (7.64 g, 73%); $\delta H$(CDCl$_3$) 7.1-7.9(4H,m, aryl), 4.40(2H,S,CH$_2$), 2.45(3H,S,SCH$_3$H).

m-Methylthiophenacyl bromide (7.6 g, 30 mmol) and hexamethylenetetramine (4.2 g, 30 mmol) were stirred in methylene chloride (160 ml) for 1½ h at room temperature. The reaction was then filtered to yield the hexamine salt as a pale yellow solid (10.08 g, 85%) m.p. 140°-142° C. The hexamine salt was added to a mixture of ethanol (40 ml) and concentrated hydrochloric acid (10 ml) and left standing overnight. A solution of dilute hydrochloric acid was added and the reaction filtered to yield the hydrochloride salt (4.22 g, 75%); $\delta H$ ((CD$_3$)$_2$SO) 8.50(S, NH), 7.8-7.5(m,aryl), 4.6(S, CH$_2$).

The isobutoxy formic anhydride of monic acid A was prepared from monic acid A (1.72 g, 5 mmol), triethylamine (0.75 ml, 5 mmol), and isobutylchloroformate (0.7 ml, 5 mmol). After 20 mins at 0° C. the m-thiomethylphenacyl ammonium chloride (1.58 g) and triethylamine (1.75 ml) were added and stirred overnight. The reaction mixture was poured into brine, extracted ethyl acetate, and the extract dried ($MgSO_4$), and evaporated under reduced pressure. The residue was purified by chromatography on silica gel (15 g) eluting with a gradient of 0 to 6% methanol in dichloromethane to yield 3-methylthiophenacyl monamide A as a pale yellow oil (630 mg, 25%); $\nu$max (CHCl$_3$) 3400, 1690, 1660, 1630, 1440 cm$^{-1}$; $\lambda$max (EtOH) 232 nm ($\epsilon$m 24,743); $\delta H$(CD$_3$OD) 7.85-7.25(4H, m, aryl), 5.90(1H,S,H2), 4.70(2H, S, CH$_2$-1$^1$), 2.50(3H, S, SCH$_3$), 2.15(3H,S,CH$_3$-15), 1.22(3H,d,CH$_3$-14), 0.94(3H,d,CH$_3$-17).

m-Methylthiophenacyl monamide A (491 mg, 0.97 mmol) in dry THF (30 ml) was treated with triethylamine (0.6 ml, 4.3 mmol), trimethylsilyl chloride (0.55 ml, 4.3 mmol) and a few crystals of 4-N,N'-dimethylaminopyridine. After stirring for 1 h at room temperature the reaction mixture was filtered and the filtrate evaporated under reduced pressure. To the residue was added acetonitrile (3 ml), pyridine (3 ml), triethylamine (0.3 ml), carbon tetrachloride (0.4 ml) and triphenylphosphine (0.52 g, 2 mmol). The solution darkened after a few minutes and was stirred at room temperature for 1 h then evaporated under reduced pressure, and the residue taken up in ethyl acetate and aqueous sodium chloride-sodium bicarbonate. The organic layer was separated, dried ($MgSO_4$), and evaporated under reduced pressure. The resulting residue was treated with THF (50 ml), water (12 ml), and concentrated hydrochloric acid (15 drops) to remove the protecting groups. After 5 mins the reaction was quenched with aqueous sodium bicarbonate, extracted with ethyl acetate and the extracts dried ($MgSO_4$) and evaporated under reduced pressure. The residual oil was purified by chromatography on silica gel (15 g) eluting with a gradient of 0 to 6% methanol in dichloromethane to yield the title oxazole as a pale yellow oil (151 mg, 30%); $\nu$max (film) 3400, 1650, 1585, 1525, 1505 cm$^{-1}$, $\lambda$max (EtOH) 301 nm ($\epsilon$m 14, 938); $\delta H$(CDCl$_3$) 7.50-7.05(5H, m, aryl+H4$^1$), 6.25(1H, 5, H2), 2.50(3H, S, SCH$_3$), 2.30(3H, S, CH$_3$-15), 1.20(3H, d, CH$_3$-14), 0.94(3H, d, CH$_3$-17).

EXAMPLE 23

5-m-Methylsulphonylphenyl-2-(1-normon-2-yl) oxazole A 5-m-Methylthiophenyl-2-(1-normon-2-yl) oxazole A (122 mg, 0.25 mmol) was dissolved in methylene chloride (20 ml) and cooled to 0° C. m-Chloroperoxybenzoic acid (69 mg, 0.5 mmol) and sodium hydrogen carbonate (42 mg, 0.5 mmol) were added and reaction stirred for 6 h then left standing overnight. The crude product was purified by chromatography on silicagel (7 g) eluting with a gradient of 0 to 4% methanol in dichloromethane to yield the title compound as a pale yellow foam (73 mg, 56%); νmax (film) 3440, 1650, 1610, 1525, 1300, 1150 cm$^{-1}$; δH (CDCl$_3$) 8.17(1H, S, H2″), 7.87(2H$_1$ d,d, H4″,6″), 7.63(1H, t, H5″), 7.50(1H, S, H4$^1$) 6.30(1H, S, H2), 3.13(3H, S, SO$_2$CH$_3$), 2.33(3H, S, CH$_3$-15), 1.22(3H, d, CH$_3$-14), 0.94(3H, d, CH$_3$-17).

EXAMPLE 24

5-p-Dimethylaminosulphonylphenyl-2-(1-normon-2-yl)oxazole A

The diazonium salt prepared from p-aminoacetophenone (27 g, 0.2 mmol), concentrated hydrochloric acid (140 ml), water (30 ml) and sodium nitrite (14 g, 0.2 mol) was added to a mixture of acetic acid (250 ml), sulphur dioxide (80 g), and cuprous chloride (3 g) at 20° C. After 40 min the mixture was cooled to 0° C. and water (1 l) added. Filtration, and drying of the residue followed by recrystallisation from carbon tetrachloride then gave p-acetylbenzenesulphonyl chloride as off-white needles (24 g, 55%); m.p. 70°-72° C., lit mp *=85° C.; δH (CDCl$_3$) 8.1(4H, S, aryl), 2.6(3H, S, Me).
* v. Christof Troltzsch, *J. Prakt. Chem.*, 192 (1963).

p-Acetylbenzenesulphonyl chloride (4.0 g, 18 mmol), aqueous dimethylamine (10 ml, 55 mmol), and THF (30 ml) were stirred together for 1 h at 20° C. and then partitioned between ethyl acetate and brine. The organic layer was dried (MgSO$_4$) and evaporated under reduced pressure and the resulting residue recrystallised from either water or ether to give p-dimethylaminosulphonylacetophenone as fine white needles (3.8 g, 93%) m.p. 98°-99° C. (H$_2$O); δH (dmso-d$_6$) 8.0(4H, ABq, aryl), 2.65(9H, S, 3 x Me).

p-Dimethylaminosulphonylacetophenone (2.3 g, 10 mmol) in chloroform (30 ml) was treated with bromine (0.5 ml, 10 mmol). When the reaction was complete the solution was washed with aqueous sodium carbonate, dried (MgSO$_4$) and evaporated under reduced pressure to give p-dimethylaminosulphonylphenocyl bromide as white crystals, which could be collected with petrol (2.8 g, 92%); δH (CDCl$_3$) 8.0(4H, ABq, aryl), 4.5(2H, S, CH$_2$), 2.7(6H, S, CH$_3$).

p-Dimethylaminosulphonylphenacyl bromide (2.8 g, 9 mmol) was converted to its hexaminium salt with hexamine (1.4 g, 10 mmol) in chloroform (100 ml). This was collected and dissolved in concentrated hydrochloric acid-ethanol (1:3, 50 ml). After 16 h at 20° C. the mixture was filtered and the filtration evaporated under reduced pressure to give a solid which was extracted with boiling 2-propanol.

Removal of the 2-propanol under reduced pressure gave p-dimethylaminosulphonylphenacylammonium chloride as a yellow powder after collection with ether (2.4 g, 85%); δH (dmso-d$_6$) 8.6(3H, bs, NH$_3^\oplus$), 8.1(4H, ABq, aryl), 4.1(2H, S, CH$_2$), 2.7(6H, 3, CH$_3$).

p-Dimethylaminosulphonylphenacylammonium chloride (1.4 g, 5 mmol) and chloroacetic anhydride (0.5 ml, 6 mmol) in benzene (50 ml) were heated at reflux for 3 h; the solution was then cooled and filtered to give p-dimethylaminosulphonylphenacyl chloracetamide as a yellow powder (1.3 g, 83%); δ$_H$ (dmso-d$_6$) 8.8(1H, t, NH) 8.1(4H, ABq, aryl), 4.8(2H, d, CH$_2$N), 4.3(2H, S, CH$_2$Cl), 2.7(6H, S, CH$_3$).

p-Dimethylaminosulphonylphenacyl chloracetamide (1.3 g, 4 mmol) and phosphoryl chloride (10 ml) were heated together at reflux for 2 h and then dissolved in dichloromethane. The mixture was washed with aqueous sodium carbonate, dried (MgSO$_4$) and evaporated under reduced pressure to give a dark oil. This was extracted with boiling benzene. Removal of the benzene under reduced pressure and crystallation of the residue with petrol then gave 2-chloromethyl-5-p-dimethylaminosulphonylphenyloxazole as waxy yellow rhombs (0.65 g, 52%); δH (CDCl$_3$) 7.8(4H, S, aryl), 7.4(1H, S, het-H), 4.7(2H, S, CH$_2$), 2.7(6H, S, CH$_3$).

2-Chloromethyl-5-p-dimethylaminosulphonylphenyloxazole (0.36 g, 1.2 mmol) and triethyl phosphite (0.27 m, 1.8 mmol) were heated at 160° C. for 1 h. Direct chromatography (5 g silica, 0 to 5% methanol in dichloromethane) then gave diethyl 5-p-dimethylaminosulphonylphenyl-2-oxazolylmethylphosphonate as a yellow gum (0.45 g, 93%), δH (CDCl$_3$) 7.7(4H, s, aryl), 7.3(1H, S, het-H), 4.6(4H, m, OCH$_2$), 3.4(1H, d, PCH$_2$), 2.7(6H, S, NMe$_2$), 1.3(6H, t, CCH$_3$).

3-[5-(2,3-Epoxy-5-hydroxy-4-methylhexyl)-3,4-dihydroxytetrahydropyran-2-yl]propan-2-one (150 mg, 0.5 mmol) in THF (5 ml) was treated with chlorotrimethylsilane (0.25 ml, 2 mmol), triethylamine (0.28 ml, 2 mmol) and 4-N,N-dimethylaminopyridine (5 mg) for 2 h at 20° C. The mixture was then filtered and evaporated under reduced pressure and the resulting residue extracted with ether. The combined ether extracts were filtered and evaporated under reduced pressure and the resulting residue, (the "protected ketone") dissolved in THF, and set aside for the next stage of the reaction.

To a suspension of sodium hydride (13 mg, 0.5 mmol) in THF (2 ml) at 0° C. was added diethyl 5-p-dimethylaminosulphonylphenyl-2-oxazolylmethylphosphonate (0.20 g, 0.5 mmol) in more THF (2 ml). The mixture was stirred at room temperature until hydrogen evolution had ceased and the solution was homogeneous (ca. 1 h). The solution was cooled (0° C.), the protected ketone vide supra added, stirred for 30 minutes at 0° C. and then at ambient temperature for 1 h. The mixture was quenched with ammonium chloride then extracted with ethyl acetate and dried (MgSO$_4$). Solvent removal under reduced pressure gave an oil which was taken up in THF/water (2.5 ml, 4:1) and treated with acid (6 drops, concentrated hydrochloric acid) for 5 min. After this time the mixture was quenched with sodium bicarbonate and extracted with ethyl acetate. Drying (MgSO$_4$) and solvent removal under reduced pressure gave the crude product, which was purified by chromatography (20 g silica, 0 to 12% methanol in dichloromethane) to give the title normonyloxazole as a pale yellow oil (75 mg, 27%); νmax (film) 3400, 2950, 1650, 1605, 1340, 1160 cm$^{-1}$; λmax (EtOH) 321 nm (Em 15,600); δ$_H$(CDCl$_3$) 7.79(4H, ABq, aryl), 7.51(1H, S, het-H), 6.30(1H, S, H2), 2.72(6H, S, NMe$_2$), 2.34(3H, S, CH$_3$-15), 1.21(3H, d, CH$_3$-14), 0.93(3H, d, CH$_3$-17); δ$_C$ (CD$_3$OD) 163.0 (C1), 149.7 (C3, C4'), 135.3 (C4″), 132.7 (C1″), 128.9 (C3″), 125.5 (C5'), 124.8 (C2″), 113.0 (C2), 75.7 (C5), 70.9 (C13), 70.5 (C7), 69.3 (C6), 65.9 (C16), 61.1 (C11), 56.2 (C10), 43.4 (C12), 43.0 (C4), 40.5 (C8), 38.0 (NMe$_2$), 32.3 (C9), 20.2 (C14), 19.8 (C15), 12.1 (C17).

EXAMPLE 25

5-m-Methylsulphinylphenyl-2-(1-normon-2-yl)oxazole A 5-m-Methylthiophenyl-2-(1-normon-2-yl)oxazole A (122 mg, 0.25 mmol) was dissolved in dichloromethane (20 ml) and cooled to 0° C. m-Chloroperoxybenzoic acid (34.5 mg, 0.25 mmol) and sodium hydrogen carbonate (21 mg, 0.25 mmol) were added and stirred for 30 mins. The reaction was purified by chromatography on silica gel (7 g) eluting with a gradient of 0 to 6% methanol in dichloromethane to yield the title compound as a pale yellow oil (65 mg, 51%); $\nu$max (film) 3400, 1710, 1650, 1525, 1500, 1410 cm$^{-1}$; $\lambda$max (EtOH) 224 nm ($\epsilon$m 13, 531), 304($\epsilon$m 19,816); $\delta_H$ (CDCl$_3$) 7.95–7.50(4H, m, aryl), 7.48(1H, S, H4'), 6.30(1H, S, H2), 2.80(3H, S, SOCH$_3$), 2.34(3H, S, CH$_3$ 15), 1.22(3H, d, CH$_3$-14), 0.94(3H, d, CH$_3$-17); $\delta_c$(CDCl$_3$) 161.9 (C1), 147.9, 147.2 (C3,C5'), 130.1, 129.9, 126.5, 123.4, 123.0, 119.1 (C1", 2", 3", 4", 5", 6"), 124.5 (C4'), 113.2 (C2), 75.5 (C5), 71.4 (C13), 70.8 (C7), 69.3 (C6), 65.6 (C16), 61.4 (C11), 55.7 (C10), 43.0 (C4, C12), 39.8 (C8), 32.0 (C9), 21.0 (C14), 19.9 (C15), 12.8 (C17).

EXAMPLE 26

5-o-Nitrophenyl-2-(1-normon-2-yl)oxazole A o-Nitroacetophenone (8.3 g, 50 mmol) in ether (100 ml) was treated with aluminium chloride (catalytic amount) followed by bromine (2.55 ml, 50 mmol) over 10 mins and the reaction stirred for 30 mins. The reaction was quenched with aqueous sodium bicarbonate, the ether layer separated, dried (MgSO$_4$) and evaporated under reduced pressure. The residue was taken up in ethyl acetate, the solution was dried (MgSO$_4$), and evaporated under reduced pressure to yield o-nitro phenacyl bromide as a yellow oil (9.45 g, 77%); $\delta$H(CDCl$_3$) 7.2–8.35(4H, m, aryl), 4.30(2H, S, CH$_2$).

o-Nitrophenacylbromide (9.45 g, 38 mmol) was dissolved in dichloromethane (100 ml) and hexamethylenetetramine (5.4 g, 38 mmol) added and the mixture stirred for 1 h. The reaction was then filtered to yield a pale green solid m.p. 136°–138° C. (7.38 g, 50%). This solid was added to ethanol (40 ml) and concentrated hydrochloric acid (10 ml) and stirred for 3 h then left standing for 2 days. The reaction mixture was filtered, and the residue was washed with water, and dried to yield a pale yellow solid. This was dissolved in aqueous sodium hydroxide, extracted with ethyl acetate, and the extracts evaporated under reduced pressure. Dilute hydrochloric acid was added to the residue and the resulting solution filtered and the filtrate evaporated under reduced pressure to yield o-nitrophenacylammonium chloride as a dark brown solid (1.45 g, 39%); $\delta$H((CD$_3$)$_2$SO) 8.8(1H, S, NH), 8.4–7.8(4H, m, aryl), 4.6(S, CH$_2$).

The isobutoxy formic mixed anhydride of monic acid A was prepared from monic acid A (1,72 g, 5 mmol), triethylamine (0.75 ml, 5 mmol) and isobutylchloroformate (0.7 ml) and o-nitrophenacyl ammonium chloride (1.09 g, 5 mmol) and triethylamine (0.75 ml, 5 mmol) added and reaction mixture stirred for 4 h. The reaction mixture was then poured into brine, extracted with ethyl acetate, the organic layer separated and dried (MgSO$_4$) and evaporated under reduced pressure. The residue was purified by chromatography on silicagel (15 g) eluting with a gradient of 0 to 4% methanol in dichloromethane to yield o-nitrophenacyl monamide A as a pale yellow foam (431 mg, 17%); $\nu$max (film) 3400, 2500, 1720, 1660, 1630, 530, 1450 cm$^{-1}$; $\lambda$max (EtOH) 217 nm ($\epsilon$m 19, 675); $\delta$H(CD$_3$OD) 8.19(1H, d, H3$^{11}$), 7.85(1H, t, H4$^{11}$), 7.74(1H, d, H6$^{11}$), 7.66(1H, t, H5$^{11}$), 5.78(1H, S, H2), 4.43(2H, S, CH$_2$–1$^1$), 2.09(3H, S, CH$_3$-15), 1.21(3H, d, CH$_3$-14), 0.96(3H, d, CH$_3$-17); $\delta$c (CD$_3$OD) 200.7 (C2$^1$), 169.7 (C1), 153.3 (C3), 147.3 (C2$^{11}$), 136.7 (C1$^1$), 135.4, 132.3, 129.4, 125.2 (C3$^{11}$, 4$^{11}$, 5$^{11}$, 6$^{11}$), 120.3 (C2), 76.2 (C5), 71.6 (C13), 70.7 (C7), 70.0 (C6), 66.3 (C16), 61.3 (C11), 56.8 (C10), 43.6, 43.5 (C4, C12), 41.4 (C8), 32.9 (C9), 20.3 (C14), 19.0 (C15), 12.2 (C17).

To a solution of o-nitrophenacyl monamide A (410 mg, 0.8 mmol) in dry T H F (35 ml) was added trimethylsilylchloride (0.55 ml, 4.3 mmol), triethylamine (0.6 ml, 4.3 mmol) and a few crystals of p-dimethylaminopyridine. The reaction was stirred at room temperature for 2 h and then filtered. The filtrate was evaporated under reduced pressure to give the protected amide which was dissolved in acetonitrile (3 ml), pyridine (3 ml), triethylamine (0.3 ml, 2 mmol), carbon tetrachloride (0.4 ml, 4 mmol) and treated with triphenylphosphine (0.52 g, 2 mmol). On heating to 60° C. the reaction mixture went black after a few minutes. The reaction mixture was stirred at 60° C. for 1 h and then evaporated under reduced pressure. The residue was taken up in ethyl acetate/aqueous sodium bicarbonate, washed with brine, and the organic layer evaporated under reduced pressure. The resulting residue was deprotected by stirring for 5 min in a mixture of T H F (40 ml), water (10 ml) and concentrated hydrochloric acid (20 drops). The reaction was quenched with aqueous sodium bicarbonate and extracted with ethyl acetate. The organic layer was washed with brine, dried (MgSO$_4$) and evaporated under reduced pressure. The residual black oil was purified by chromatography on silicagel (10 g) eluting with a gradient of 0 to 4% methanol in dichloromethane to yield the title compound as a bright yellow oil (124 mg, 31%); $\nu$max (film) 3400, 1650, 1530, 1350 cm$^{-1}$; $\lambda$max (EtOH) 205 nm ($\epsilon$m 20, 509), 292 nm ($\epsilon$m 15, 475); $\delta$H(CDCl$_3$) 7.84–7.45(4H, m, aryl), 7.43(1H, S, H4$^1$), 6.27(1H, S, H2), 2.28(3H, S, CH$_3$-15), 1.22(3H, d, CH$_3$-14), 0.94(3H, d, CH$_3$-17); $\delta_c$ (CDCl$_3$) 162.5 (C1), 148.8 (C3), 147.4 (C5$^1$), 144.6 (C1$^{11}$), 132.3 (C5$^{11}$), 132.1 (C2$^{11}$), 129.0 (C4$^{11}$, 3$^{11}$), 127.4 (C6$^{11}$), 124.4 (C4$^1$), 112.9 (C2), 75.4 (C5), 71.3 (C13), 70.6 (C7), 69.1 (C6), 65.5 (C16), 61.3 (C11), 55.6 (C10), 43.0, 42.9 (C4, C12), 39.7 (C8), 31.9 (C9), 20.8 (C14), 19.7 (C15), 12.6 (C17).

EXAMPLE 27

5-Benzyl-2-(1-normon-2-yl)oxazole A

To diazomethane (40 mmol) in ether (100 ml) at 0° C. was added phenylacetyl chloride (2.65 ml, 20 mmol). After 30 min at 0° C. the excess diazomethane and the ether were blown off with nitrogen, and then under vacuum to leave 1-diazo-3-phenyl-2-propanone as a yellow oil (3.05 g, 95%); $\delta$H (CDCl$_3$) 7.2(5H, S, aryl), 5.1(1H, S, CH=N$_2$), 3.5(2H, S, CH$_2$).

1-Diazo-3-phenyl-2-propanone (0.8 g, 5 mmol) in dichloromethane (5 ml) was added to a mixture of boron triflouride diethyl etherate (1.2 ml, 10 mmol), chloroacetonitrile (6.4 ml, 100 mmol) and dichloromethane (5 ml) at 20° C. After 0.5 h at 20° C. the solution was washed with cold aqueous 20% sodium hydroxide, dried (MgSO$_4$), and evaporated under reduced pressure to give an oil which was purified by chromatography (10 g silica, dichloromethane) to give 2-chloromethyl-5-benzyl oxazole as a yellow oil (0.64 g, 62%); $\delta$H (CDCl$_3$) 7.2(5H, S, aryl), 6.7(1H, S, het-H), 4.5(2H, S, CH$_2$Cl), 4.2(2H, S, CH$_2$Ar), 2-Chloromethyl-5-benzyloxazole (0.6 g, 3 mmol) and triethyl phosphite (0.7 ml, 4.5 mmol) were heated together for 1 h at 160° C. and then cooled. Direct chromatography (10 g silica, 0 to 5% methanol in dichloromethane) then gave diethyl 5-benzyl-2-oxazolylmethyl phosphonate as a light brown oil (0.65 g, 70%); $\delta$H (CDCl$_3$) 7.2(5H, S, aryl), 6.7(1H, S, het-H), 4.1(4H, m, OCH$_2$), 3.9(2H, S, CH$_2$Ar), 3.3(2H, d, CH$_2$P), 1.3(6H, t, Me).

3-[5-(2,3-Epoxy-5-hydroxy-4-methylhexyl)-3,4-dihydroxytetrahydropyram-2-yl]-propan-2-one (300 mg, 1 mmol) in T H F (10 ml) was treated with chlorotrimethylsilane (0.5 ml, 4 mmol), triethylamine (0.6 ml, 4 mmol) and 4-N,N-dimethylaminopyridine (5 mg) for 2 h at 20° C. The mixture was then filtered and evaporated under reduced pressure and the resulting residue extracted with ether. The combined ether extracts were filtered and evaporated under reduced pressure and the resulting residue (the "protected ketone") dissolved in T.H.F., and set aside for the next stage of the reaction.

To a suspension of sodium hydride (25 mg, 1 mmol) in THF (2 ml) at 0° C. was added diethyl 5-benzyl-2-oxazolylmethyl phosphonate (310 mg, 1 mmol) in more THF (2 ml). The mixture was stirred at room temperature until hydrogen evolution had ceased and the solution was homogeneous (ca. 0.5 h). The solution was cooled (0° C.), the protected ketone vide supra added, stirred for 30 minutes at 0° C. and then at ambient temperature for 1 h. The mixture was quenched with ammonium chloride then extracted with ethyl acetate and dried (MgSO$_4$). Solvent removal under reduced pressure gave an oil which was taken up in THF/water (50 ml, 4:1) and treated with acid (10 drops, concentrated hydrochloric acid) for 5 min. After this time the mixture was quenched with sodium bicarbonate and extracted with ethyl acetate. Drying (MgSO$_4$) and solvent removal under reduced pressure gave the crude product which was purified by chromatography (20 g silica, 0 to 10% methanol in dichloromethane) to give the title normonyloxazole as a colourless oil (100 mg, 22%); $\nu$max (film) 3400, 2900, 1655, 730 cm$^{-1}$; $\lambda$max (EtOH) 266 nm ($\epsilon_m$ 19,800); $\delta$H(CD$_3$OD) 7.25(5H, m, aryl), 6.79(1H, S, het-H0, 6.13(1H, S, H2), 4.05(2H, S, CH$_2$Ar), 2.16(3H, S, CH$_3$-15), 1.22(3H, d, CH$_3$-14), 0.94(3H, d, CH$_3$-17); $\delta$c(CD$_3$OD) 162.6 (C1), 152.0 (C3), 148.0 (C5), 138.2 (C1$^{11}$), 129.6 (C2$^{11}$, 3$^{11}$, 5$^{11}$, 6$^{11}$), 127.7 (C4$^{11}$), 124.1 (C4$^1$), 113.7 (C2), 76.5 (C5), 71.6 (C13), 70.7 (C7), 70.0 (C6), 66.3 (C16), 61.4 (C11), 56.8 (C10), 43.6 (CH, 12), 41.4 (C8), 32.9 (CH$_2$Ar) 32.5 (C9), 20.3 (C14), 19.5 (C15), 12.2 (C17).

EXAMPLE 28

5-[2-(5-Bromo)-thienyl]-2-(1-normon-2-yl)oxazole A

To a solution of 2-acetyl-5-bromothiophene (10.25 g, 50 mmol) in ether (150 ml) containing a few crystals of aluminium chloride was added bromine (12.6 ml, 50 mmol) and reaction mixture stirred for 1 h. The mixture was evaporated under reduced pressure and the residue washed with water to yield the bromide as a bright yellow solid m.p. 68°-69°; $\delta$H (CDCl$_3$) 7.05 and 7.45(2H, ABq, thienyl), 4.20(2H, S, CH$_2$).

The bromide was dissolved in methylene chloride (150 ml) and hexamethylenetetramine (7.0 g, 50 mmol) added and stirred for 1 h. The precipitate was filtered off, washed with methylene chloride, and dried to yield the hexamine salt as a white solid m.p. 168°-170° C. (19.64 g, 93%). This salt (19.64 g, 46.5 mmol) was added to a mixture of ethanol (60 ml) and concentrated hydrochloric acid (20 ml) stirred for 3 h, and left standing overnight. Water was added to the residue and the remaining solid filtered and dried to give the amine hydrochloride salt (9.04 g, 76%); $\delta$H((CD$_3$)$_2$SO) 8.5(3H, S(br), NH), 7.95 and 7.45(2H, ABq, thienyl), 4.45(2H, S, CH$_2$).

Isobutoxy formic mixed anhydride of monic acid A was prepared from monic acid A (3.44 g, 10 mmol), triethylamine (1.5 ml, 11 mmol), and isobutylchloroformate (1.4 ml, 11 mmol) at 0° C. for 20 mins. The amine hydrochloride (2.56 g, 10 mmol) and triethylamine (1.5 ml, 11 mmol) were added and the reaction stirred overnight. The mixture was then poured into brine/aqueous sodium bicarbonate, extracted with ethyl acetate and the extract was dried (MgSO$_4$), and evaporated under reduced pressure. The residue was purified by chromatography using silicagel (20 g) eluting with a gradient of 0 to 4% methanol in dichloromethane to yield N-[2-oxo-2-(2-(5-bromo)-thienyl)ethyl]monamide A as a white foam (1.65 g, 30%); $\nu$max (film) 3400, 1660, 1630, 1520, 1410, cm$^{-1}$; $\lambda$max (EtOH) 221 nm, ($\epsilon_m$ 17, 097), 294 nm, ($\epsilon_m$ 10, 784); $\delta$H(CD$_3$OD) 7.76(1H, d, thienyl), 7.27(1H, d, thienyl), 5.88(1H, S, H2), 4.59(2H, S, CH$_2$−1$^1$), 2.15(3H, S, CH$_3$-15), 1.20(3H, d, CH$_3$-14), 0.96(3H, d, CH$_3$-17); $\delta$c (CD$_3$OD) 188.1 (C3$^1$), 169.7 (C1), 153.3 (C3), 144.4 (C4$^1$), 134.4 133.0 (C5$^1$, C6$^1$), 124.7 (C7$^1$), 120.6 (C2), 76.3 (C5), 71.6 (C13), 70.7 (C7), 70.0 (C6), 66.3 (C16), 61.4 (C11), 56.8 (C10), 46.6 (C2$^1$), 43.6 (C4, 12), 41.5 (C8), 33.0 (C9), 20.4 (C14), 19.1 (C15), 12.2 (C17).

EXAMPLE 29

2-(1-Normon-2-yl)-5-phenylthiazole A

A mixture of N-phenacylacetamide (0.70 g, 4 mmol), 2,4-bis(4-methoxyphenyl)-1,3-dithia-2,4-diphosphetane-2,4-disulphide (Lawesson's reagent) (0.80 g, 2 mmol) and toluene (10 ml) was heated for 1.5 h at reflux and then evaporated under reduced pressure. The residue was purified by chromatography (10 g silica, dichloromethane) to give 2-methyl-5-phenylthiazole as a yellowish solid (0.11 g, 16%) m.p. 72°-4° C.; $\delta$H (CDCl$_3$) 7.85(1H, S, CH), 7.3-7.7(5H, m, C$_6$H$_5$), 2.7(3H, S, CH$_3$).

3-[5-(2,3-Epoxy-5-hydroxy-4-methylhexyl)-3,4-dihydroxytetrahydropyran-2-yl] propan-2-one (300 mg, 1 mmol) in THF (10 ml) was treated with chlorotrimethylsilane (0.5 ml, 4 mmol), triethylamine (0.6, 4 mmol) and 4-N,N-dimethylaminopyridine (5 mg) for 2 h at 20° C. The mixture was then filtered and evaporated under reduced pressure and the resulting residue extracted with ether. The combined ether extracts were filtered and evaporated under reduced pressure and the resulting residue (the protected ketone) dissolved in THF, and set aside for the next stage of the reaction.

A solution of 2-methyl-5-phenylthiazole (193 mg, 1.1 mmol) and butyl lithium (1.1 mmol) in dry THF at −78° C. was stirred for 10–15 minutes. To the metalated species produced was added trimethylsilyl chloride (0.14 ml, 1.1 mmol) and this mixture stirred at −78° C. for 45 minutes, followed by a further 45 minutes at −20° C. to −25° C. The resultant solution was cooled to −78° C. and a further equivalent of butyl lithium (1.02 mmol) added. Stirring was continued for 45 minutes before adding the protected ketone, vide supra, and allowing to warm to room temperature. The mixture was quenched with ammonium chloride solution, extracted with ethyl acetate (3×50 ml) and the extracts dried (MgSO$_4$). Solvent removed under reduced pressure gave the protected thiazole which was taken up in THF/water (4:1, 50 ml) and treated with concentrate hydrochloric acid (10 drops) for 5 min, then finally quenched with sodium bicarbonate solution. Extraction with ethylacetate, drying (MgSO$_4$) and solvent removal under reduced pressure gave the triol which was further purified by column chromatography on silica gel (2 g) using 0 to 6% methanol in dichloromethane as eluent. This gave the title compound as a white foam (0.17 g, 37%); $\nu_{max}$ (film) 3400, 1640, 810, 730 cm$^{-1}$; $\lambda_{max}$ (EtOH) 321 nm ($\epsilon_m$ 24,100); $\delta_H$(CD$_3$OD) 8.02(1H, S, Het-H), 7.3–7.7(5H, m, C$_6$H$_5$), 6.63(1H, S, H-2), 2.21(3H, S, CH$_3$-15), 1.22(3H, d, CH$_3$-14), 0.94(3H, d, CH$_3$-17); $\delta_C$(CD$_3$OD) 166.1 (C1), 145.5 (C3) 139.8 (HetC-5), 138.5 (HetC-4), 132.5, 130.1, 129.3, 127.5 (C$_6$H$_5$), 121.8 (C2), 76.6 (C5), 71.6 (C13), 70.7 (C7), 70.0 (C6), 66.3 (C16), 61.3 (C11) 56.8 (C10), 44.1 (C4), 43.7 (C12), 41.5 (C8), 33.0 (C9), 20.3 (C14), 20.2 (C15), 12.2 (C17); m/e (relative intensity) 459 M$^+$, 6%), 215(100) 175(21) (Found: 459.2040. C$_{25}$H$_{33}$NO$_5$S requires 459.2077).

EXAMPLE 30

3-Methyl-5-(1-normon-2-yl) isoxazole A

A mixture of 5-hydroxymethyl-3-methylisoxazole (2.26 g), triphenylphosphine (5.24 g) and dry carbon tetrachloride (40 ml) was heated for 3 h at reflux and then cooled and filtered. The filtrate was evaporated under reduced pressure and the residue taken up in 50% ether-hexane and filtered through a plug of silica. Evaporation of the filtrate under reduced pressure afforded 5-hydroxymethyl-2-methylisoxazole (2.16 g, 82%); $\delta_H$(CCl$_4$) 6.1(1H, s, H4), 4.5(2H, s, CH$_2$), 2.2(3H, s, CH$_3$).

5-Chloromethyl-3-methylisoxazole (1.12 g) was dissolved in triethyl phosphite (2.0 ml) and heated at reflux for 1 h. The residue was then distilled under reduced pressure to give 5-diethylphosphonomethyl-3-methylisoxazole (1.47 g, 74%); bp 122°–5° C. at 0.5 mm; $\nu_{max}$ (film) 2980, 2930, 2910, 1605, 1440, 1420, 1390, 1255, 1160, 1060-1010, 980, 900 cm$^{-1}$; $\delta_H$ (CDCl$_3$) 1.35(3H, t, J=7 Hz, OCH$_2$CH$_3$), 2.30(3H, s, CH$_3$-het), 3.30(1H, d, J$_{H-P}$=24 Hz, CH$_2$-P), 4.10(2H, m, OCH$_2$CH$_3$), 6.05(1H, d, J=3 Hz, CH-Het); $\delta_C$(CDCl$_3$) 11.4 (C5), 16.3, 16.4(OCH$_2$CH$_3$), 24.6, 26.8 (C1), 62.7, 62.8(OCH$_2$CH$_3$), 104.1, 104.2 (C3), 160.1 (C4), 163.5, 163.6 (C2); m/e (relative intensity) 233(M$^+$, 18%), 192(47), 177(41), 136(50), 109(100), 97(82), 96(35), 81(76), 43(32) (Found: 233.0831. C$_9$H$_{16}$NO$_4$P requires 233.0816).

To a solution of 3R,4R-dihydroxy-5S-(2S,3S-epoxy-5S-hydroxy-4S-methylhexyl)tetrahydropyran-2S-yl acetone (604 mg, 2.0 mmol) in dry THF (20 ml) was added triethylamine (0.87 ml, 6.20 mmol), trimethylsilyl chloride (0.78 ml, 6.20 mmol) and a catalytic amount of 4-(N,N-dimethylamino)pyridine. After stirring at room temperature for 2 h the triethylamine hydrochloride was filtered off and the solution concentrated under reduced pressure. The resultant oil was taken up in anhydrous ether, filtered, the solvent removed under reduced pressure, then the oil (the protected ketone) taken up in dry THF ready for the next stage of the reaction.

To a suspension of sodium hydride (106 mg, 50% in oil, washed, 2.20 mmol) in dry dimethoxyethane (DME, 10 ml) at 0° C. was added 5-diethylphosphonomethyl-3-methylisoxazole (489 mg, 2.10 mmol) in 1,2-dimethoxyethane (5 ml). The cooling bath was removed and the mixture stirred at room temperature until hydrogen evolution had ceased and the solution was homogeneous (ca. 2 h). The solution was cooled (0° C.), the protected ketone added, stirred for 30 minutes at 0° C. and then ambient for 1 h. The mixture was quenched with ammonium chloride then extracted with ethyl acetate and dried (MgSO$_4$). Solvent removal under reduced pressure gave an oil which was taken up in THF/water (100 ml, 4:1) and treated with acid (10 drops concentrated hydrochloric acid) for 5 min. After this time the solution was quenched with sodium bicarbonate and extracted with ethyl acetate. The extract was dried (MgSO$_4$) and the solvent evaporated under reduced pressure to give the crude product, which was chromatographed to afford the title compound as an inseparable mixture of E and Z isomers (4:1 respectively) (250 mg, 0.66 mmol, 32%); $\nu_{max}$ (film) (mixture of isomers) 3600–3200, 2970, 2930, 1720, 1655, 1585, 1570, 1450, 1415, 1110, 1050, 910, 730 cm$^{-1}$; $\lambda_{max}$(EtOH) (mixture of isomers) 259 nm ($\epsilon_m$ 17,160); $\delta_H$ (CDCl$_3$) (E-isomer only) 0.93(3H, d, J=7 Hz, CH$_3$-17), 1.21(3H, d, J=7 Hz, CH$_3$-14), 1.32(1H, q, J=7 Hz, CH-12), 1.75(2H, m, CH$_2$-9), 2.05(4H, s+m, CH$_3$-15, CH-8), 2.30(3H, s, CH$_3$-het), 2.36(1H, dd, J=14, 10 Hz, CH-4), 2.60(1H, m, CH-4'), 2.72(1H, dd, J=8, 2 Hz, CH-11), 2.83(1H, m, CH-10), 3.45–3.60(2H, m), 3.70–4.00(4H, m), 5.95(1H, s, CH-2), 6.25(1H, s, CH-2'); $\delta_C$ (CDCl$_3$) (E-isomer) 11.3(CH$_3$-het), 12.4 (C17), 19.5 (C15), 20.6 (C14), 31.8 (C9), 39.7 (C8), 42.7 (C4+12), 55.7 (C10), 61.0 (C11), 65.4 (C16), 68.9 (C6), 70.4 (C7), 70.8 (C13), 75.3 (C5), 102.8 (C2'), 113.1 (C2), 144.5 (C3), 159.6 (C3'), 168.6 (C1); Z-isomer shows 25.6 (C15), 36.2 (C4), 39.6 (C8), 103.0 (C2'), 113.0 (C2), 145.7 (C3), 168.4 (C1); m/e (relative intensity) 381(M$^+$, 1%), 279(3), 227(7), 149(19), 137(100), 97(14), 95(14), 69(22), 55(20), 43(37), 41(27) (Found: 381.2166. C$_{20}$H$_{31}$NO$_6$ requires 381.2152).

EXAMPLE 31

5-(1-Normon-2-yl)-3-phenylisoxazole A (a) 5-Bromomethyl-3-phenylisoxazole

To a solution of propargyl bromide (1.51 ml, 20 mmol) in dichloromethane (15 ml) and aqueous sodium hyopchlorite (22.4 ml, 10%, 30 mmol) at 0° C. was added dropwise with stirring benzaldoxime (2.42 g, 20 mmol) in dichloromethane (15 ml). When addition was complete the ice bath was removed and the reaction stirred for a further 2 h. The organic layer was separated and the aqueous layer washed with dichloromethane (2×20 ml) then the combined organic layers dried (MgSO$_4$). Solvent removal under reduced pressure gave a solid which was recrystallised from 40°–60° C. petroleum ether fraction to give the desired isoxazole (2.64 g, 11.1 mmol, 55%); mp 82°–3° C., $\delta_H$ (CDCl$_3$) 4.40(2H, s, CH$_2$-Br), 6.50(1H, s, CH-4), 7.3–7.9(5H, m, C$_6$H$_5$).

(b) 5-Diethylphosphonomethyl-3-phenylisoxazole

5-Bromomethyl-3-phenylisoxazole (7.14 g, 30 mmol) and triethyl phosphite (10.4 ml, 60 mmol) were heated at 150° C. until no more ethyl bromide distilled, then the temperature maintained for a further 1 h. The mixture was then distilled under reduced pressure to give 5-diethylphosphonomethyl-3-phenylisoxazole bp 190°–192° C. at 0.5 mm Hg (8.15 g, 27.6 mmol, 92%); $\nu_{max}$ (film) 2980, 2900, 1605, 1580, 1465, 1440, 1410, 1250, 1160, 1020, 970, 770, 690, 670 cm$^{-1}$; $\delta_H$(CDCl$_3$) 1.30(6H, t, J 7 Hz, OCH$_2$CH$_3$), 3.45(1H, d, J$_{H-P}$ 22 Hz, CH$_2$-P), 4.10(4H, m, OCH$_2$CH$_3$), 6.55(1H, d, J 3 Hz, CH-4), 7.40(3H, m, Ph), 7.65(2H, m, Ph); $\delta_C$ (CDCl$_3$) 16.3, 16.4(OCH$_2$CH$_3$), 24.7, 26.9(CH$_2$-P), 62.8, 62.9(OCH$_2$CH$_3$), 101.5, 101.6 (C-4), 126.8, 128.9, 130.0 (Ph), 162.8 (C-3), 164.3, 164.4 (C-2).

(c) 5-(1-Normon-2-yl)-3-phenylisoxazole A

To a solution of 3R,4R-dihydroxy-5S-(2S,3S-epoxy-5S-hydroxy-4S-methylhexyl)tetrahydropyran-2S-yl acetone (604 mg, 2.0 mmol) in dry THF (20 ml) was added triethylamine (0.87 ml, 6.20 mmol), trimethylsilyl chloride (0.78 ml, 6.20 mmol) and a catalytic amount of 4-(N,N-dimethylamino)pyridine. After stirring at room temperature for 2 h the triethylamine hydrochloride was filtered off and the solution concentrated under reduced pressure. The resultant oil was taken up in anhydrous ether, filtered, the solvent removed under reduced pressure, then the oil (the protected ketone) taken up in dry THF ready for the next stage of the reaction.

To a suspension of sodium hydride (106 mg, 50% in oil, washed, 2.20 mmol) in dry tetrahydrofuran (THF, 10 ml) at 0° C. was added 5-diethylphosphono methyl 3-phenyl isoxazole (620 mg, 2.10 mmol) in THF (5 ml). The cooling bath was removed and the mixture stirred at room temperature until hydrogen evolution had ceased and the solution was homogeneous (ca. 1 h). The solution was cooled (0° C.), the protected ketone added, stirred for 30 minutes at 0° C. and then ambient for 1 h. The mixture was quenched with ammonium chloride then extracted with ethyl acetate and dried (MgSO$_4$). Solvent removal under reduced pressure gave an oil which was taken up in THF/water (100 ml, 4:1) and treated with acid (10 drops, concentrated hydrochloric acid) for 5 min. After this time the mixture was quenched with sodium bicarbonate and extracted with ethyl acetate. Drying (MgSO$_4$) and solvent removal under reduced pressure gave the crude product which was chromatographed to give the title compound (272 mgs, 0.61 mmol, 31%); $\nu_{max}$ (film) 3600–3200, 2970, 2920, 1655, 1590, 1570, 1465, 1405, 1105, 1050, 910, 770, 690 cm$^{-1}$; $\lambda_{max}$ (EtOH) 240 nm ($\epsilon$m 22,600); $\delta$H (CDCl$_3$) 0.93(3H, d,J 7 Hz, CH$_3$-17), 1.22(3H,d,J 7 Hz,CH$_3$-14), 1.32(1H,m,CH-12), 1.74(2H,m,CH$_2$-9), 2.04(1H,m,CH-8), 2.13(3H, s,CH$_3$-15), 2.38(1H,dd,J 14,10 Hz,CH-4), 2.50–2.75(2H,m,CH-11+CH-4a), 2.80(1H,dt,J 5 Hz,CH-10) 3.5–4.0(6H,m), 6.32(1H,s, CH-2), 6.43(1H,s,CH-2'), 7.46(3H,m,Ph), 7.80(2H,m,Ph); $\delta$c (CDCl$_3$), 12.6 (C17), 19.7 (C15), 20.7 (C14), 31.7 (C9), 39.6 (C8), 42.8 (C12,4), 55.7 (C10), 61.2 (C11), 65.5 (C16), 68.9 (C6), 70.4 (C7), 71.1 (C13), 75.3 (C5), 100.1 (C2'), 113.2 (C2), 126.8, 129.0 130.0 (Ph), 145.0 (C3), 162.4 (C3'), 169.4 (C1); m/e (relative intensity) 443(M$^+$, 3%), 199(100), 83(8), 69(14), 67(9), 55(11), 45(8), 43(15), 41(14) (Found: 443.2322. C$_{25}$H$_{33}$NO$_6$ requires 443.2308) and the z isomer (47.4 mgs, 0.11 mmol, 5%); $_{max}$ 3600–3200, 2970, 2920, 1650, 1590, 1570, 1465, 1405, 1105, 1045, 770, 730, 690 cm$^{-1}$; $\lambda_{max}$ (EtOH) 241 nm (m 23,380); $\delta$H (CDCl$_3$), 0.92(3H,d, J 7 Hz,CH$_3$-17), 1.22(3H, d,J 7 Hz, CH$_3$-14), 1.37(1H,q,J 7 Hz,CH-12), 1.74(2H,m,CH$_2$-9), 2.05(4H,m+s,CH-8+CH$_3$-15), 2.61(1H,dd,J 14,10 Hz, CH-4), 2.73(1H,dd,J 8,2 Hz,CH-11), 2.82(1H,dt,J 2,6 Hz,CH-10), 3.03(1H,dd,J 14,2 Hz,CH-4a), 3.55(2H,m), 3.75–4.00(4H,m), 6.29(1H,s,CH-2), 6.59(1H,s,CH-2'), 7.45(3H,m,Ph), 7.80(2H,m,Ph); $\delta$c (CDCl$_3$), 12.4 (C17), 20.5 (C14), 25.8 (C15), 31.9 (C9), 36.5 (C9), 36.5 (C4), 39.6 (C8), 42.7 (C12), 55.8 (C10), 61.2 (C11), 65.5 (C16), 69.5 (C6), 70.3 (C7), 70.9 (C13), 76.2 (C5), 100.4 (C2') 1130 (C2), 126.8, 129.0 130.0 (Ph), 146.4 (C3), 162.5 (C3'), 169.3 (C1); m/e (relative intensity) 443(M$^+$, 1%), 200(17), 199(100), 77(14), 69(17), 67(12), 55(22), 45(19), 43(26), 41(28) (Found: 443.2345 C$_{25}$H$_{33}$NO$_6$ requires 443.2305.

EXAMPLE 32

3-(1-Normon-2-yl)isoxazole A (a) 3-Hydroxymethyl isoxazole

A solution of ethyl isoxazole-3-carboxylate (9.92 g, 70 mmol) in anhydrous ether (10 ml) was added dropwise to a stirred suspension of lithium aluminium hydride (2.67 g, 70 mmol) in ether (100 ml). The mixture was then refluxed until tlc indicated the reaction was complete (ca. 30 min) then the reaction was cautiously quenched with 2% sulphuric acid. The ether layer was separated, dried (MgSO$_4$) and the solvent removed under reduced pressure to yield the 3-hydroxymethylisoxazole (4.23 g, 42.7 mmol, 61%); $\delta_H$ (CDCl$_3$) 4.00(1H, bs, OH), 4.70(2H, s, CH$_2$-OH), 6.40(1H, d, J 2 Hz, CH-4), 8.30(1H, d, J 2 Hz, CH-5).

(b) 3-Chloromethyl isoxazole

A solution of 3-hydroxymethyl isoxazole (4.23 g, 43 mmol) and triphenylphosphine (11.3 g, 42 mmol) in carbon tetrachloride (100 ml) was heated at reflux for 18 h. Solvent was removed under reduced pressure then the residue taken up in ether and filtered. The filtrate was concentrated under reduced pressure and further purified by short path distillation (bp 60° C. at 10 mm) to give the desired chloride (1.41 g, 12 mmol, 28%); $\delta_H$ (CDCl$_3$) 4.50(2H, s, CH$_2$-Cl), 6.40(1H, d, J 2 Hz, CH-4), 8.40(1H, d, J 2 Hz, CH-5).

(c) 3-Diethylphosphonomethyl isoxazole

3-Chloromethyl isoxazole (1.41 g, 12 mmol) and triethylphosphite (3.13 ml, 18 mmol) were heated at 140° C. for 1 h. Distillation (short path) yielded the phosphonate (390 mg, 1.78 mmol, 15%); bp 110°–120° C. at 0.7 mm Hg; $\delta_{H}$·(CDCl$_3$) 1.30(6H, t, J 7 Hz, OCH$_2$CH$_3$), 3.30(2H, d, J$_{P-H}$ 22 Hz, CH$_2$-P), 4.10(4H, m, OCH$_2$CH$_3$), 6.40(1H, s, CH-4), 8.35(1H, s, CH-5).

(d) 3-(1-Normon-2-yl)isoxazole A

To a solution of 3R,4R-dihydroxy-5S-(2S,3S-epoxy-5S-hydroxy-4S-methylhexyl)tetrahydropyran-2S-yl acetone (302 mg, 1.00 mmol) in dry THF (20 ml) was added triethylamine (0.6 ml, 3.90 mmol), trimethylsilyl chloride (0.5 ml, 3.90 mmol) and a catalytic amount of 4-(N,N-dimethylamino)pyridine. After stirring at room temperature for 2 h the triethylamine hydrochloride was filtered off and the solution concentrated under reduced pressure. The resultant oil was taken up in anhydrous ether, filtered, solvent removed under reduced pressure, then the oil (the protected ketone) taken up in dry THF ready for the next stage of the reaction.

To a solution of lithium diisopropylamide [from diisopropylamine (0.14 ml) and butyl lithium (1.06 ml of a 0.94M solution, 1.00 mmol)] in THF (10 ml) at −78° C. was added 3-diethylphosphonomethyl isoxazole (229 mg, 1.00 mmol) in THF (5 ml). The solution was stirred for 30 minutes then raised to 0° C. and stirred for a further 30 minutes. The protected ketone was added and the reaction stirred at 0° C. for 30 minutes then room temperature for 18 h before quenching with ammonium chloride, extracting with ethyl acetate and drying (MgSO$_4$). Solvent removal under reduced pressure gave an oil which was taken up in THF/water (100 ml, 4:1) and treated with acid (10 drops, concentrated hydrochloric acid) for 5 min. After this time the mixture was quenched with sodium bicarbonate and extracted with ethyl acetate. Drying (MgSO$_4$) and solvent removal under reduced pressure gave the crude product (310 mg) which was chromatographed (0–5%

MeOH/CH$_2$Cl$_2$, 5 g, SiO$_2$) to give the title compound as an inseparable mixture with the Z-isomer (42 mg, 0.11 mmol, 11%); $\nu_{max}$ (film) 3600–3200, 2970, 2930, 1650, 1625, 1550, 1450, 1380, 1110, 1050, 850 cm$^{-1}$; $\lambda_{max}$ (EtOH) 220 nm ($\epsilon_m$ 7,620); $\delta_H$ (CDCl$_3$) 0.94(3H, d, J 7 Hz, CH$_3$-17), 1.22(3H, d, J 7 Hz, CH$_3$-14), 1.35(1H, m, CH-12), 1.72(2H, m, CH$_2$-9), 2.00(1H, m, CH-8), 2.08+2.10(3H, 2 x s, CH$_3$-15), 2.2–2.4(1H, m, CH-4), 2.55–2.90(3H, m), 3.5–4.0(6H, m), 6.25(1H, s, CH-2), 6.36(1H, d, J 2 Hz, CH-2'), 8.35(1H, d, J 2 Hz, CH-3').

EXAMPLE 33

5-Methyl-3-(1-normon-2-yl) isoxazole A (a) Ethyl 5-methylisoxazole-3-carboxylate A mixture of ethyl 2,4-dioxovalerate (25 ml, 178 mmol), hydroxylamine hydrochloride (13.7 g, 197 mmol) and sodium bicarbonate (15.4 g, 183 mmol) in ethanol (125 ml) were heated at reflux for 2.5 h, cooled and the solvent removed under reduced pressure. The residue was taken up in chloroform and washed with water, the organic layer separated and dried (MgSO$_4$). Solvent removal and distillation under reduced pressure gave the desired product (15.44 g, 100 mmol, 56%); b.p. 82°–86° C. at 0.5 mm Hg; $\nu_{max}$ (film) 3120, 2980, 2930, 1730, 1600, 1450, 1270, 1200, 1100, 1020, 915, 830, 780 cm$^{-1}$; $\delta_H$ (CDCl$_3$) 1.40(3H,t,J 7 Hz, OCH$_2$CH$_3$), 2.50(3H,s,CH$_3$-5), 4.40(2H,q,J 7 Hz, OCH$_2$CH$_3$), 6.40(1H,s,CH-4).

(b) 3-Hydroxymethyl-5-methylisoxazole

Ethyl 5-methylisoxazole-3-carboxylate (15.44 g, 100 mmol) in dry ether was added dropwise to a stirred suspension of lithium aluminium hydride (3.5 g, 100 mmol) in ether (100 ml). The mixture was then refluxed until tlc indicated the reaction was complete (ca 30 min) then the reaction was cautiously quenched with 2% sulphuric acid. The ether layer was separated, dried (MgSO$_4$) and the solvent removed under reduced pressure to leave an oil which was further purified by distillation to give 3-hydroxymethyl-5-methylisoxazole (5.85 g, 52 mmol, 52%); b.p. 80° C. at 0.5 mm Hg; $\nu_{max}$ (film) 3600–3100, 2930, 1610, 1480, 1255, 1130, 1050, 1000, 890, 800, 760 cm$^{-1}$; $\delta_H$ (CDCl$_3$), 2.40(3H,s,CH$_3$-5), 4.30(1H,bs,OH), 4.65(2H,s,CH$_2$-OH), 6.05(1H,s,CH-4).

(c) 3-Chloromethyl-5-methylisoxazole

A solution of 3-hydroxymethyl-5-methyl isoxazole (6.50 g, 57.5 mmol) and triphenylphosphine (15.1 g, 57.5 mmol) in carbon tetrachloride (120 ml) were heated at reflux for 18 h. Solvent was removed from the cooled mixture under reduced pressure then the residue taken up in ether and filtered. The filtrate was concentrated under reduced pressure then flash chromatographed through silica using 1:1 ether: 40°–60° C. petroleum ether fraction as eluant to give 3-chloromethyl-5-methylisoxazole (5.43 g, 41.3 mmol, 72%); $\nu_{max}$ (film) 3130, 2960, 2920, 1610, 1475, 1400, 1270, 1250, 1160, 1130, 1010, 920, 890, 800, 750 cm$^{-1}$; $\delta_H$ (CDCl$_3$) 2.40(3H,s,CH$_3$-5), 4.55(2H,s,CH$_2$-Cl), 6.10(1H,s,CH-4).

(d) 3-Diethylphosphonomethyl-5-methylisoxazole

3-Chloromethyl-5-methylisoxazole (3.95 g, 30 mmol) and triethylphosphite (10.4 ml, 60 mmol) were heated at reflux for 2 h. Distillation under reduced pressure yielded the phosphonate (5.03 g, 21.6 mmol, 72%); b.p. 125° C. at 0.5 mm Hg; $\nu_{max}$ (film) 2980, 2930, 1610, 1475, 1440, 1420, 1390, 1250, 1060–1010, 960, 900, 810 cm$^{-1}$; $\delta_H$ (CDCl$_3$) 1.30(6H,t,J 7 Hz, OCH$_2$CH$_3$), 2.40(3H,s,CH$_3$-5), 3.20(2H,d,J$_{H-P}$ 22 Hz, CH$_2$-P), 4.10(2H,m,OCH$_2$CH$_3$), 6.10(1H,s,CH-4); $\delta_H$ (CDCl$_3$) 12.2(CH$_3$-5); 16.3, 16.4(OCH$_2$CH$_3$), 23.5, 25.7(CH$_2$-P), 62.4, 62.6(OCH$_2$CH$_3$), 102.5 (C-4), 155.9, 156.0 (C-3), 169.9 (C-5).

(e) 5-Methyl-3-(1-normon-2-yl)-isoxazole

To a solution of 3R,4R-dihydroxy-5S-(2S,3S-epoxy-5S-hydroxy-4S-methyl-hexyl) tetrahydropyran-2S-yl acetone (604 mg, 2.0 mmol) in dry THF (20 ml) was added triethylamine (0.87 ml, 6.20 mmol), trimethylsilyl chloride (0.78 ml, 6.20 mmol) and a catalytic amount of 4-(N,N-dimethyl-amino)pyridine. After stirring at room temperature for 2 h the triethylamine hydrochloride was filtered off and the solution concentrated under reduced pressure. The resultant oil was taken up in anhydrous ether, filtered, the solvent removed under reduced pressure, then the oil (the protected ketone) taken up in dry THF ready for the next stage of the reaction.

To a solution of lithium diisopropylamide (from diisopropyl amine (0.31 ml) and butyl lithium (1.42 ml of a 1.55M solution, 2.20 mmol)) in THF (10 ml) at −78° C. was added 3-diethyl-phosphonomethyl-5-methylisoxazole (489 mgs, 2.10 mmol) in THF (5 ml). The solution was stirred for 30 minutes then raised to 0° C. and stirred for a further 30 minutes. The ketone was added and the reaction stirred at 0° C. for 30 minutes then room temperature for 3 h before quenching with ammonium chloride, extracting with ethyl acetate and drying (MgSO$_4$). Solvent removal under reduced pressure gave an oil which was taken up in THF/water (100 ml, 4:1) and treated with acid (10 drops, concentrated hydrochloric acid) for 5 minutes. After this time, the mixture was quenched with sodium bicarbonate and extracted with ethyl acetate. Drying (MgSO$_4$) and solvent removal under reduced pressure gave the crude product which was chromatographed (0–5% MeOH/CH$_2$Cl$_2$, 15 g SiO$_2$) to give the title compound (250 mgs, 0.65 mmol, 33%); $\nu_{max}$ (film), 3600–3200, 2970, 2930, 1650, 1600, 1450, 1380, 1110, 1050, 910, 730 cm$^{-1}$; $\lambda_{max}$ (EtOH) 232 nm ($\epsilon_m$ 10,900); $\delta_H$ (CDCl$_3$) 0.92(3H,d,J 7 Hz,CH$_3$-17) 1.22(3H,d,J 7 Hz,CH$_3$-14), 1.34(1H,q,J 7 Hz,CH-12), 2.72(2H,t,J 6 Hz, CH$_2$-9), 2.03(4H,s+m,CH$_2$-15+CH-8), 2.40(4H,s+m,CH$_3$-het+CH-4), 2.63(1H,dd,J 14,2 Hz,CH-4a), 2.70(1H,dd,J 9,2 Hz,CH-11), 2.82(1H,dt,J 2,5 Hz,CH-10), 3.54(2H,m), 3.75–3.95(4H,m), 6.01(1H,s, CH-het), 6.20(1H,s,CH-2); $\delta_C$(CDCl$_3$), 12.1 (C4), 12.5 (C17), 19.3 (C15), 20.7 (C14), 31.7 (C9), 39.5 (C8), 42.6 (C4), 42.7 (C12), 55.6 (C10), 61.1 (C11), 65.4 (C16), 68.9 (C6), 70.4 (C7), 71.0 (C13), 75.3 (C5), 102.2 (C2), 114.5 (C2), 144.1 (C3), 160.7 (C1), 168.6 (C3'); m/e (relative intensity) 381(M$^+$, 1%), 227 (5), 138 (18), 137 (100), 122 (19), 69 (18), 55 (19), 45 (21), 43 (52), 41 (31) (Found: 381.2172.C$_{20}$H$_{31}$NO$_6$ requires 381.2151) and the Z-isomer (60.5 mgs, 0.15 mmol, 8%); $\nu_{max}$ (film) 3600–3200, 2970, 2930, 1645, 1605, 1450, 1110, 1050, 910, 730 cm$^{-1}$; $\lambda_{max}$ (EtOH) 232 nm ($\epsilon_m$ 11,000) $\delta_H$ (CDCl$_3$), 0.94(3H,d,J 7 Hz,CH$_3$-17), 1.21(3H,d,J 7 Hz, CH$_3$-14), 1.34(1H,q,J 7 Hz,CH-12), 1.59(1H,m,CH-9), 1.82(1H,m, CH-9a), 2.04(4H,d,J 1 Hz+m,CH$_3$-15+CH-8), 2.80(3H,m), 3.5–4.0(6H,m), 5.88(1H,s,CH-2'), 6.05(1H,s,CH-2); $\delta_C$ (CDCl$_3$), 12.0 (C4'), 12.7 (C17), 20.7 (C14), 26.8 (C15), 31.8 (C9), 36.8 (C4), 38.9 (C8), 42.9 (C12), 56.0 (C10), 61.4 (C11), 65.5 (C16), 67.3 (C6), 70.3 (C7), 71.3 (C13), 76.8 (C5), 103.0 (C2'), 114.2 (C2), 146.9 (C3), 160.1 (C1), 168.8 (C3'); m/e (relative intensity) 382 (MH$^+$, 2%), 381 (M$^+$, 1%), 227 (7), 166 (42), 150 (54), 137 (100), 45 (50), 43 (88), 41 (48) (Found: 381.2127. C$_{20}$H$_{31}$NO$_6$ requires 381.2149).

EXAMPLE 34

3-(1-Normon-2-yl)-5-phenylisoxazole A (a) 3-Hydroxymethyl-5-phenylisoxazole

A solution of ethyl 5-phenylisoxazole-3-carboxylate (5.90 g, 27 mmol) in ether (30 ml) was added dropwise to a suspension of lithium aluminium hydride in ether (20 ml). When addition was complete, the mixture was heated at reflux for 1 h then a further quantity of lithium aluminium hydride (0.25 g) was added and reflux continued for 0.5 h. The reaction was cautiously quenched with 2% sulphuric acid and the ether layer separated, dried ($MgSO_4$) and the solvent removed under reduced pressure to yield 3-hydroxymethyl-5-phenylisoxazole (2.10 g, 12 mmol, 44%); $\delta H$ ($CDCl_3$) 3.60(1H,br,OH), 4.75(2H,s,$CH_2$), 6.35(1H,s,CH), 7.2–7.8(5H,m,$C_6H_5$).

(b) 3-Chloromethyl-5-phenylisoxazole

3-Hydroxymethyl-5-phenylisoxazole (2.10 g, 12 mmol) was refluxed with triphenylphosphine (3.14 g, 12 mmol) in carbon tetrachloride (40 ml) overnight. After cooling the solvent was removed under reduced pressure and the residue taken up in ether, the solution filtered and concentrated to give an oil. This material was filtered through a plug of silicagel (5 g, ether-hexane 1:1) to remove triphenylphosphine oxide then crystallised to give the title compound (1.33 g, 6.9 mmol, 58%); m.p. 48°–9° C.; $\nu_{max}$ ($CHCl_3$) 3000, 1610, 1590, 1570, 1450, 1265, 945, 690 cm$^{-1}$; $\delta H$ ($CDCl_3$) 4.55(2H,s,$CH_2Cl$), 6.55(1H,s,CH-het) 7.2–8.0(5H,m,Ph).

(c) 3-Diethylphosphonomethyl-5-phenylisoxazole

3-Chloromethyl-5-phenylisoxazole (2.07 g, 10 mmol) and triethylphosphite (1.72 ml, 10 mmol) were heated at reflux for 2 h then the mixture distilled under reduced pressure to yield the title compound (1.85 g, 6.27 mmol, 63%); b.p. 192° at 0.5 mm Hg; $\nu_{max}$ (film) 2980, 2900, 1610, 1590, 1570, 1500, 1450, 1420, 1390, 1250, 1160, 1060–1010, 970, 760, 690 cm$^{-1}$; $\delta H$ ($CDCl_3$) 1.30(3H,t, J 7 Hz,$OCH_2CH_3$), 3.30(2H,d,J 21 Hz,$CH_2$-P), 4.20(2H,m,$OCH_2CH_3$), 6.60(1H,s,CH-het), 7.2–7.9(5H,m,Ph).

(d) 3-(1-Normon-2-yl)-5-phenyl isoxazole A

To a solution of 3R,4R-dihydroxy-5S-(2S,3S-epoxy-5S-hydroxy-4S-methyl-hexyl)tetrahydropyran-2S-yl acetone (604 mg, 2.0 mmol) in dry THF (20 ml) was added triethylamine (0.87 ml, 6.20 mmol), trimethylsilyl chloride (0.78 ml, 6.20 mmol) and a catalytic amount of 4-(N,N-dimethyl-amino)pyridine. After stirring at room temperature for 2 h the triethylamine hydrochloride was filtered off and the solution concentrated under reduced pressure. The resultant oil was taken up in anhydrous ether, filtered, the solvent removed under reduced pressure, then the oil (the protected ketone) taken up in dry THF ready for the next stage of the reaction.

To a suspension of sodium hydride (106 mg, 50% in oil, washed, 2.20 mmol) in dry tetrahydrofuran (THF, 10 ml) at 0° C. was added 3-diethylphosphonomethyl-5-phenylisoxazole (620 mg, 2.10 mmol) in THF (5 ml). The cooling bath was removed and the mixture stirred at room temperature until hydrogen evolution had ceased and the solution was homogeneous (ca. 2 h). The solution was cooled (0° C.), the protected ketone added, stirred for 30 minutes at 0° C. and then at ambient temperature for 1 h. The mixture was quenched with ammonium chloride then extracted with ethyl acetate and dried ($MgSO_4$). Solvent removal under reduced pressure gave an oil which was taken up in THF/water (100 ml, 4:1) and treated with acid (10 drops, concentrated hydrochloric acid) for 5 min. After this time the mixture was quenched with sodium bicarbonate and extracted with ethyl acetate. Drying ($MgSO_4$) and solvent removal under reduced pressure gave the crude product which was chromatographed to give the title compound (110 mg, 0.24 mmol, 12%); $\nu_{max}$ (film) 3600–3200, 2970, 2920, 1655, 1615, 1590, 1575, 1495, 1450, 1420, 1380, 1110, 1050, 910, 865, 830 cm$^{-1}$; $\lambda_{max}$ (EtOH) 266 nm ($\epsilon_m$ 21,230); $\delta_H$ ($CDCl_3$) 0.93(3H, d, J 7 Hz, $CH_3$-17), 1.22(3H, J 7 Hz, $CH_3$-14), 1.33(1H, q, J 7 Hz, CH-12), 1.74(2H, m, $CH_2$-9), 2.02(1H, m, CH-8), 2.11(3H, s, $CH_3$-15), 2.42(1H, dd, J 12, 9 Hz, CH-4), 2.65(1H, m, CH-4'), 2.72(1H, dd, J 8, 2 Hz, CH-11), 2.83(1H, dt, J 2, 5 Hz, CH-10), 3.5–4.0(6H, m), 6.27(1H, s, CH-2), 6.54(1H, s, CH-2'), 7.44(3H, m, Ar), 7.78(2H, m, Ar); $\delta_C$ ($CDCl_3$) 12.6 (C17), 19.6 (C15), 20.8 (C14), 31.7 (C9), 39.5 (C8), 42.6, 42.7 (C12, 4), 55.7 (C10), 61.2 (C11), 65.4 (C16), 69.0 (C6), 70.4 (C7), 71.1 (C13), 75.3 (C5), 100.0 (C2'), 114.4 (C2), 125.8, 129.0, 130.1 (Ar), 144.7 (C3), 161.1 (C1), 169.2 (C3'); m/e (relative intensity) 443 (M+, 3%), 200 (23), 199 (100), 105 (36), 94 (16), 69 (24), 57 (16), 55 (22), 43 (29), 41 (23) (Found: 443.2286. $C_{25}H_{33}NO_6$ requires 443.2306) and the Z-isomer (33.5 mg, 0.08 mmol, 4%); $\nu_{max}$ (film) 3600–3200, 2970, 2930, 1655, 1615, 1590, 1575, 1495, 1450, 1420, 1110, 1050, 910, 865, 830, 790 cm$^{-1}$; $\lambda_{max}$ (EtOH) 266 nm; $\delta_H$($CDCl_3$) 0.94(3H, d, J 7 Hz, $CH_3$-17), 1.20(3H, d, J 7 Hz, $CH_3$-14), 1.31(1H, q, J 7 Hz, CH-12), 1.62(1H, m, CH-9a), 1.82(1H, m, CH-9b), 2.09(4H, m+s, CH-8+$CH_3$-15), 2.68(1H, dd, J 8, 2 Hz, CH-11), 2.82(3H, m, CH-10+$CH_2$-4), 3.5–4.0(6H, m), 6.15(1H, s, CH-2), 6.43(1H, s, CH-2'), 7.45(3H, m, Ar), 7.75(2H, m, Ar); $\delta_C$($CDCl_3$) 12.7 (C17), 20.8 (C14), 26.8 (C15), 31.8 (C9), 37.0 (C4), 43.0 (C12), 56.0 (C10), 61.5 (C11), 65.5 (C16), 67.5 (C6), 70.3 (C7), 71.4 (C13), 76.8 (C5), 100.8 (C2'), 114.1 (C2), 126.0, 129.1, 130.4($C_6H_5$), 147.5 (C3), 160.6 (C1), 169.4 (C3'); m/e (relative intensity) 443 (M+, 1%), 340 (6), 228 (34), 211 (50), 199 (65), 105 (100), 77 (50), 45 (50), 43 (45), 41 (56) (Found: 443.2303. $C_{25}H_{33}NO_6$ requires 443.2303).

EXAMPLE 35

5-(1-Normon-2-yl)-2-phenyloxazole A (a) 5-Chloromethyl-2-phenyl oxazole

A solution of chloracetyl chloride (freshly distilled, 1.59 ml, 20 mmol) in ether (10 ml) was added dropwise to a cooled (0° C.) solution of diazomethane in ether (40 mmol, ex 10.8 g Diazald) and stirred until nitrogen evolution had ceased (ca. 10–15 mins). The solvent was blown off using nitrogen and the residual oil containing the diazoketone used without further purification. The 1-chloro-3-diazo propanone was taken up in dichloromethane (50 ml) and added dropwise to a solution of boron trifluoride etherate (4.9 ml, 40 mmol) and benzonitrile (10.2 ml, 100 mmol) in dichloromethane (150 ml) and stirred until nitrogen evolution had ceased. The mixture was then poured onto 20% aqueous sodium hydroxide solution (300 ml), the organic layer separated, washed with brine and dried ($MgSO_4$). Solvent removal then distillation at reduced pressure gave an oil which was further purified by column chromatography ($CH_2Cl_2$ as eluant, 20 g silica) to give the title compound (870 mgs, 4.50 mmol, 22%); $V_{max}$ (film), 3060, 2960, 1665, 1610, 1550, 1545, 1480, 1450, 1355, 1280, 1125, 1040, 1020, 990, 900, 875, 840, 780, 700 cm$^{-1}$; $\delta H$ (CDCl₃) 4.60(2H,s,CH₂-Cl), 7.10(1H,s,CH-4), 7.40(3H,m,Ph), 7.90(2H,m,Ph).

(b) 5-Diethylphosphonomethyl-2-phenyl oxazole

5-Chloromethyl-2-phenyl oxazole (870 mgs, 4.50 mmol) and triethylphosphite (1.17 ml, 6.75 mmol) were heated at reflux for 3 h, cooled, the excess triethylphosphite removed under reduced pressure and the residue column chromatographed (0 to 5% MeOH/CH₂Cl₂, 10 g silica) to give the title compound (794 mgs, 2.69 mmol, 60%); δH (CDCl₃) 1.30(6H,t,J 7 Hz,OCH₂CH₃), 3.30(2H,d,$J_{P-H}$ 22 Hz,CH₂-P) 4.10(4H,m,OCH₂CH₃), 7.00(1H,d,$J_{P-H}$ 3 Hz,CH-4), 7.40(3H,m,Ph), 8.00(2H,m,Ph).

(c) 5-(1-Normon-2-yl)-2-phenyl oxazole A

To a solution of 3R,4R-dihydroxy-5S-(2S,3S-epoxy-5S-hydroxy-4S-methyl-hexyl)tetrahydropyran-2S-yl acetone (604 mg, 2.0 mmol) in dry THF (20 ml) was added triethylamine (0.87 ml, 6.20 mmol), trimethylsilyl chloride (0.78 ml, 6.20 mmol) and a catalytic amount of 4-(N,N-dimethyl-amino)pyridine. After stirring at room temperature for 2 h the triethylamine hydrochloride was filtered off and the solution concentrated under reduced pressure. The resultant oil was taken up in anhydrous ether, filtered, the solvent removed under reduced pressure, then the oil taken up in dry THF ready for the next stage of the reaction.

To a suspension of sodium hydride (96 mg, 50% in oil, washed, 2.00 mmol) in dry tetrahydrofuran (THF, 10 ml) at 0° C. was added 5-diethylphosphono methyl-2-phenyl oxazole (590 mg, 2.00 mmol) in THF (5 ml). The cooling bath was removed and the mixture stirred at room temperature until hydrogen evolution had ceased and the solution was homogeneous (ca. 1.5 h). The solution was cooled (0° C.) the protected ketone added, stirred for 30 minutes at 0° C. and then ambient for 1 h. The mixture was quenched with ammonium chloride then extracted with ethyl acetate and dried (MgSO₄). Solvent removal under reduced pressure gave an oil which was taken up in THF/water (100 ml, 4:1) and treated with acid (10 drops, concentrated hydrochloric acid) for 5 min. After this time the mixture was quenched with sodium bicarbonate and extracted with ethyl acetate. Drying (MgSO₄) and solvent removal under reduced pressure gave the crude product which was chromatographed (0–5% MeOH/CH₂Cl₂ on silica) to give the title compound as an inseparable mixture with the Z isomer (91 mgs, 0.21 mmol, 10%) E:Z 3:1; $V_{max}$(film) (both isomers) 3600–3200, 2970, 2910, 1640, 1480, 1450, 1380, 1110, 1050, 905, 750, 710, 690 cm⁻¹; $\lambda_{max}$ (EtOH) (both isomers) 306 nm (Em 16, 170); δH (CDCl₃) (E isomer) 0.93(3H,d,J 7 Hz,CH₃-17), 1.22(3H,d, J 7 Hz, CH₃-14), 1.33(1H,m,CH-12), 1.76(2H,m,CH₂-9), 2.12(3H,s, CH₃-15), 2.39(1H,dd,J 14,9,CH-4), 2.5-2.9(3H,m), 3.4-4.0(6H,m), 6.26(1H,s,CH-2), 7.03(1H,s,CH-2), 7.45(3H,m,Ph), 8.02(2H,m,Ph).

EXAMPLE 36

3-(4-Methylsulfinylphenyl)-5-(1-normon-2-yl) isoxazole A

To a solution of 3R,4R-dihydroxy-5S-(2S,3S-epoxy-5S-hydroxy-4S-methylhexyl)tetrahydropyran-2S-yl acetone (585 mg, 1.94 mmol) in dry THF (20 ml) was added triethylamine (1.20 ml, 8.60 mmol), trimethylsilyl chloride (1.00 ml, 8.60 mmol) and a catalytic amount of 4-(N,N-dimethylamino)pyridine. After stirring at room temperature for 2 h the triethylamine hydrochloride was filtered off and the solution concentrated under reduced pressure. The resultant oil was taken up in anhydrous ether, filtered, the solvent removed under reduced pressure, then the oil (the protected ketone) taken up in dry THF ready for the next stage of the reaction.

To a suspension of sodium hydride (93 mg, 50% in oil, washed, 1.94 mmol) in dry tetrahydrofuran (THF, 10 ml) at 0° C. was added 5-(diethylphosphonomethyl)-3-(4-methylsulphinylphenyl) isoxazole (678 mg, 1.94 mmol) in THF (5 ml). The cooling bath was removed and the mixture stirred at room temperature until hydrogen evolution had ceased and the solution was homogeneous (ca. 3 h). The solution was cooled (0° C.), the protected ketone added, stirred for 30 minutes at 0° C. and then ambient for 3 h. The mixture was quenched with ammonium chloride then extracted with ethyl acetate and dried (MgSO₄). Solvent removal under reduced pressure gave an oil which was taken up in THF/water (100 ml, 4:1) and treated with acid (10 drops, concentrated hydrochloric acid) for 5 min. After this time the mixture was quenched with sodium bicarbonate and extracted with ethyl acetate. Drying (MgSO₄) and solvent removal under reduced pressure gave the crude product which was chromatographed to give the title compound as a 4:1 mixture with the Z-isomer (410 mg, 8.12 mmol, 42%).

EXAMPLE 37

3-(4-Methylsulfonylphenyl)-5-(1-normon-2-yl) isoxazole A

A mixture of 3-p-methylsulfinylphenyl-5-(1-normon-2-yl) isoxazole A (0.20 g, 0.4 mmol), sodium hydrogen carbonate (75 mg, 0.90 mmol) and m-chloroperbenzoic acid (91 mg, 0.45 mmol) in dichloromethane (10 ml) was stirred for 2 h at 20° C., and then diluted with ethyl acetate. The solution was washed with aqueous sodium bicarbonate, dried (MgSO₄) and evaporated under reduced pressure. The residue was purified by chromatography (silicagel, 0 to 10% methanol in dichloromethane) to give the title compound (90 mg, 1.73 mmol, 43%) as a white foam.

EXAMPLE 38

5-(4-Methylthiophenyl)-2-(1-normon-2-yl) thiazole A

To a solution of 3R,4R-dihydroxy-5S-(2S,3S-epoxy-5S-hydroxy-4S-methylhexyl)tetrahydropyran-2S-yl acetone (151 mg, 0.5 mmol) in dry THF (20 ml) was added triethylamine (0.6 ml, 4.3 mmol), trimethylsilyl chloride (0.5 ml, 4.0 mmol) and a catalytic amount of 4-(N,N-dimethylamino)pyridine. After stirring at room temperature for 2 h the triethylamine hydrochloride was filtered off and the solution concentrated under reduced pressure. The resultant oil was taken up in anhydrous ether, filtered, the solvent removed under reduced pressure, then the oil (the protected ketone) taken up in dry THF ready for the next stage of the reaction.

A solution of 2-methyl-5-(4-methylsulphinylphenyl)-thiazole (0.5 mmol) and butyl lithium (0.5 mmol) in dry THF at −78° C. was stirred for 30 minutes. To the metalated species produced was added trimethylsilyl chloride (64 μl, 0.5 mmol) and this mixture stirred at −78° C. for 15 minutes, followed by a further 15 minutes at −78° to 0° C. The resultant solution was cooled to −78° C. and a further equivalent of butyl lithium (0.49 mmol) added. Stirring was continued for 45 minutes before adding the protected ketone, vide supra, and allowing to warm to room temperature. The mixture was quenched with ammonium chloride then extracted with ethyl acetate and dried (MgSO$_4$). Solvent removal under reduced pressure gave an oil which was taken up in THF/water (100 ml, 4:1) and treated with acid (10 drops, concentrated hydrochloric acid) for 5 min. After this time the mixture was quenched with sodium bicarbonate and extracted with ethyl acetate. Drying (MgSO$_4$) and solvent removal under reduced pressure gave the crude product which was chromatographed using 0 to 5% methanol/dichloromethane as eluant to give the title compound (84 mg, 0.17 mmol, 33%), mp 128°–34° C.

EXAMPLE 39

4,5-Dimethyl-2-(1-normon-2-yl)oxazole A

A solution of 3-[5-(2,3-epoxy-5-hydroxy-4-methylhexyl)-3,4-dihydroxytetrahydropyran-2-yl]propan-2-one (604 mg) in THF (20 ml) was treated with chlorotrimethylsilane (0.84 ml), triethylamine (0.92 ml) and a catalytic amount of 4-N,N-dimethylaminopyridine. After 2 h at 20° C. the reaction mixture was filtered and the filtrate evaporated under reduced pressure. The resultant oil was taken up in anhydrous ether, filtered, the solvent evaporated under reduced pressure, then the oil (the protected ketone) taken up in dry THF ready for the next stage of the reaction.

A solution of 2,4,5-trimethyloxazole (244 mg) in dry THF (20 ml) was cooled to −78° C. under an atmosphere of argon. A solution of n-butyl lithium in hexane (1.8 ml, 1.2M) was added, followed after 10 min by chlorotrimethylsilane (0.30 ml). After 45 min at −78° C. the solution was warmed to 0° C. for 45 min and then recooled to −78° C. A further quantity of n-butyl lithium (1.8 ml) was added and the solution stirred at −78° C. for 45 min. The solution of the protected ketone was added and the reaction mixture allowed to warm to room temperature. The reaction mixture was quenched with ammonium chloride solution, extracted with ethyl acetate and the combined extracts dried (MgSO$_4$). The solvent was removed under reduced pressure and the resulting oil was dissolved in THF/water (4:1, 25 ml) and concentrated hydrochloric acid (6 drops) added. After stirring for 12 min excess sodium bicarbonate solution was added and the mixture extracted with ethyl acetate. The combined organic extracts were dried (MgSO$_4$) and evaporated under reduced pressure to an oil which was purified on silica (10 g) eluting with 0 to 4% methanol in dichloromethane. The title oxazole was isolated as a colourless oil (0.185 g, 23%); $\nu_{max}$ (film) 3400, 1650, 730 cm$^{-1}$; $\lambda_{max}$ 275 nm ($\epsilon_m$ 14,700); $\delta_H$ (CDCl$_3$) 6.11(1H, s, H2), 2.24, 2.09(6H, 2s, Het-CH$_3$), 2.21(3H, s, CH$_3$-15), 1.23(3H, d, CH$_3$-14), 0.92(3H, d, CH$_3$-17); $\delta_C$(CDCl$_3$) 159.3 (C1), 144.9 (C3), 142.1 (oxazole C5), 130.7 (oxazole C4), 113.2 (C2), 75.5 (C5), 7.10 (C13), 70.4 (C7), 68.9 (C6), 65.4 (C16), 61.1 (C11), 55.6 (C10), 42.7 (C4), 42.6 (C12), 39.5 (C8), 31.8 (C9), 20.7 (C14), 19.4 (C15), 12.5 (C17), 11.0 and 9.9 (2 x Het-CH$_3$); m/e (relative intensity) 395 (M$^+$, 9%), 151 (100), 111 (21), 84 (27) (Found: 395.2313. C$_{21}$H$_{33}$NO$_6$ requires 395.2308).

EXAMPLE 40

4-Methyl-2-(1-normon-2-yl)-5-phenyloxazole A

A solution of 2,4-dimethyl-5-phenyloxazole (190 mg) in dry THF (10 ml) was cooled to −78° C. under argon. A solution of n-butyl lithium in hexane (0.9 ml, 1.2M) was added, followed after 10 min by chlorotrimethylsilane (0.15 ml). After 45 min at −78° C. the solution was warmed to 0° C. for 45 min and then recooled to −78° C. A further quantity of n-butyl lithium (0.9 ml) was added and the solution stirred at −78° C. for 45 min. The solution of the protected ketone (1 mM) (prepared as in example 39) was added and the reaction mixture allowed to warm to room temperature. The reaction mixture was quenched with ammonium chloride solution, extracted with ethyl acetate and the combined extracts dried (MgSO$_4$). The solvent was removed under reduced pressure and the resulting oil was dissolved in THF/water (4:1, 25 ml) and concentrated hydrochloric acid (6 drops) added. After stirring for 12 min excess sodium bicarbonate solution was added and the mixture extracted with ethyl acetate. The combined organic extracts were dried (MgSO$_4$) and evaporated under reduced pressure to an oil which was purified on silica (10 g) eluting with 0 to 4% methanol in dichloromethane. The title oxazole was isolated as a white foam (0.25 g, 55%); $\nu_{max}$ (film) 3400, 1655, 910 cm$^{-1}$; $\lambda_{max}$ (EtOH) 225 ($\epsilon_m$ 15,600), 306 nm ($\epsilon_m$ 22,200); $\delta_H$ (CDCl$_3$) 7.25-7.65(5H, m, C$_6$H$_5$), 6.24(1H, s, H2), 2.43(3H, s, Het-CH$_3$), 2.31(3H, s, CH$_3$-15), 1.21(3H, d, CH$_3$-14), 0.95(3H, d, CH$_3$-17); $\delta_C$(CDCl$_3$) 159.4 (C1), 146.4 (C3), 144.2 (Het-C5), 132.3 (Het-C4), 129.2, 128.7, 127.4, 125.1 (C$_6$H$_5$), 113.1 (C2), 75.4 (C5), 71.1 (C13), 70.4 (C7), 68.9 (C6), 65.5 (C16), 61.2 (C11), 55.6 (C10), 42.8 (C4, 12), 39.5 (C8), 31.7 (C9), 20.8 (C14), 19.6 (C15), 13.3 (Het-CH$_3$), 12.6 (C17); m/e (relative intensity) 457 (M$^+$, 6%), 213 (100), 173 (21) (Found: M$^+$457.2448. C$_{26}$H$_{35}$NO$_6$ requires 457.2461).

EXAMPLE 41

4,5-Diphenyl-2-(1-normon-2-yl)oxazole A

A solution of 4,5-diphenyl-2-methyloxazole (0.57 g) in dry THF (20 ml) was cooled to −78° C. under argon. A solution of n-butyl lithium in hexane (1.8 ml, 1.2M) was added, followed after 10 min by chlorotrimethylsilane (0.30 ml). After 45 min at −78° C. the solution was warmed to 0° C. for 45 min and then recooled to −78° C. A further quantity of n-butyl lithium (1.8 ml) was added and the solution stirred at −78° C. for 45 min. The solution of the protected ketone (2 mM) (prepared as in example 39) was added and the reaction mixture allowed to warm to room temperature. The reaction mixture was quenched with ammonium chloride solution, extracted with ethyl acetate and the combined extracts dried (MgSO$_4$). The solvent was removed under reduced pressure and the resulting oil was dissolved in THF/water (4:1, 25 ml) and concentrated hydrochloric acid (6 drops) added. After stirring for 12 min excess sodium bicarbonate solution was added and the mixture extracted with ethyl acetate. The combined organic extracts were dried (MgSO$_4$) and evaporated under reduced pressure to an oil which was purified on silica (10 g) eluting with 0 to 4% methanol in dichloromethane. The title oxazole was isolated as a white foam (0.30 g, 29%); $\nu_{max}$ (film) 3400, 1655, 910 cm$^{-1}$; $\lambda_{max}$ (EtOH) 229 nm ($\epsilon_m$ 20,800), 304 nm ($\epsilon_m$ 18,000); $\delta_H$ (CDCl$_3$) 7.2-7.7(10H, 2m, aryl), 6.31(1H, s, H2), 2.34(3H, s, CH$_3$-15), 1.20(3H, d, CH$_3$-14), 0.92(3H, d, CH$_3$-17); $\delta_C$ (CDCl$_3$) 160.1 (C1), 147.3 (C4″), 144.3 (C3), 135–126 (aryl), 126.3 (C5′), 113.0 (C2), 75.5 (C5), 71.1 (C13), 70.4 (C7), 68.9 (C6), 65.4 (C16), 61.2 (C11), 55.6 (C10), 42.8 (C4, C12), 39.5 (C8), 31.7 (C9), 20.8 (C14), 19.7 (C15), 12.6 (C17); m/e (relative intensity)

519 (M+, 12%), 275 (100), 235 (34) (Found: M+, 519.2646. $C_{31}H_{37}NO_6$ requires 519.2618).

BIOLOGICAL DATA a) Mycoplasma

The activity of the compounds of the Examples against various mycoplasmal organisms was assayed in vitro in Friis broth solidified with 0.9% agarose and inoculated with $10^3$ to $10^5$ C.F.U. The minimum inhibitory concentrations (MIC's) were determined after incubation for 6 days at 37° C. and are shown in Table I.

b) Veterinary Bacteria

The activity of the compounds of the Examples against various veterinarily important bacteria, was assayed in vitro using two-fold serial dilutions in Diagnostic Sensitivity Test Agar inoculated with $10^4$ organisms. The MIC's were determined after incubation for 18 hours at 37° C. and are shown in Table 2.

c) Human Bacteria

The activity of the compounds of the Examples against various bacteria which are important in diseases of humans, was assayed in vitro using serial dilutions in nurient agar with 5% chocolated horse blood. The MIC's were determined after incubation for 18 hours at 37° C. and are shown in Table 3.

TABLE 1

MIC's (μg/ml) against Mycoplasma

| Organism | Compound of Example No. | | | | | | | | | | | | | |
|---|---|---|---|---|---|---|---|---|---|---|---|---|---|---|
| | 1 | 2* | 3 | 4 | 5 | 9 | 10 | 6 | 7 | 11 | 12 | 13 | 14 | 15 |
| M. suipneumoniae NB12 | 1.0 | >10 | 0.1 | 0.5 | 0.05 | 0.5 | 0.05 | 0.05 | >10 | 0.1 | >10 | 0.1 | 5.0 | 0.5 |
| M. suipneumoniae JF 435 | 1.0 | >10 | 0.25 | 1.0 | 0.1 | 0.5 | 0.05 | 0.05 | >10 | 0.25 | >10 | 0.25 | 5.0 | 0.5 |
| M. suipneumoniae HK(2) | 1.0 | 10 | 0.25 | 1.0 | 0.1 | 0.5 | 0.05 | 0.05 | >10 | 0.25 | >10 | 0.25 | 5.0 | 0.5 |
| M. suipneumoniae Str. 11 | 0.5 | 10 | 0.1 | 0.5 | 0.05 | 0.5 | 0.025 | 0.05 | 10 | 0.1 | 10 | 0.1 | 2.5 | 0.5 |
| M. suipneumoniae J2206/183[b] | 1.0 | 10 | 0.25 | 1.0 | 0.1 | 0.5 | 0.05 | 0.05 | >10 | 0.25 | >10 | 0.25 | 5.0 | 0.5 |
| M. suipneumoniae MS 16 | 0.5 | 5.0 | 0.05 | 0.5 | 0.05 | 0.5 | 0.025 | 0.025 | 10 | 0.1 | 10 | 0.1 | 2.5 | 0.25 |
| M. suipneumoniae PW/C/210 | 0.5 | 5.0 | 0.1 | 0.5 | 0.05 | 0.5 | 0.025 | 0.025 | 10 | 0.1 | 10 | 0.1 | 2.5 | 0.25 |
| M. suipneumoniae LABER | 0.5 | 10 | 0.1 | 0.5 | 0.05 | 0.5 | 0.025 | 0.05 | 10 | 0.1 | >10 | 0.1 | 2.5 | 0.5 |
| M. suipneumoniae UCD 1 | 1.0 | 10 | 0.25 | 1.0 | 0.1 | 0.5 | 0.05 | 0.05 | >10 | 0.25 | >10 | 0.25 | 5.0 | 0.5 |
| M. suipneumoniae TAM 6N | 1.0 | >10 | 0.25 | 1.0 | 0.1 | 0.5 | 0.05 | 0.1 | >10 | 0.5 | >10 | 0.25 | 5.0 | 0.5 |
| M. suipneumoniae ATCC 25095 | 0.5 | 10 | 0.1 | 0.5 | 0.05 | 0.5 | 0.025 | 0.05 | 10 | 0.25 | 10 | 0.25 | 2.5 | 0.5 |
| M. suipneumoniae NCTC 10110 | 1.0 | 10 | 0.25 | 1.0 | 0.1 | 0.5 | 0.05 | 0.05 | 10 | 0.25 | >10 | 0.25 | 5.0 | 0.5 |
| M. hyorhinis ATCC 23234 | 0.5 | 10 | 0.1 | 0.5 | 0.05 | 0.5 | 0.025 | 0.025 | 10 | 0.1 | 5.0 | 0.1 | 2.5 | 0.25 |
| M. hyorhinis ATCC 25021 | 0.5 | 5.0 | 0.05 | 0.5 | 0.05 | 0.5 | 0.025 | 0.025 | 10 | 0.1 | 5.0 | 0.1 | 2.5 | 0.25 |
| M. hyosynoviae ATCC 25591 | 0.5 | 5.0 | 0.25 | 0.5 | 0.25 | 0.5 | 0.05 | 0.5 | 5.0 | 0.25 | 5.0 | 0.25 | 5.0 | 0.5 |
| M. bovis NCTC 10131 | ≦0.01 | 0.25 | 0.025 | 0.025 | ≦0.01 | 0.05 | 0.01 | 0.025 | 0.1 | ≦0.01 | 0.05 | ≦0.01 | 0.05 | 0.05 |
| M. bovigenitalium ATCC 14173 | NG | 0.5 | 0.05 | 0.05 | 0.025 | 0.1 | 0.025 | 0.05 | 1.0 | 0.1 | 1.0 | 0.025 | 0.1 | 0.05 |
| M. dispar NCTC 10125 | 0.1 | 2.5 | 0.05 | 0.25 | 0.025 | 0.1 | 0.025 | 0.025 | 2.5 | 0.1 | 5.0 | 0.05 | 0.5 | 0.1 |
| M. gallisepticum S6 | 2.5 | >10 | 0.5 | 2.5 | 0.5 | 1.0 | 0.1 | 1.0 | >10 | 0.5 | >10 | 0.5 | >10 | 1.0 |
| M. pneumoniae ATCC 15492 | 2.5 | NG | 0.5 | NG | 0.25 | 1.0 | 0.1 | 1.0 | >10 | 0.5 | >10 | 0.5, | >10 | 1.0 |

| Organism | Compound of Example No. | | | | | | | | | | | | | |
|---|---|---|---|---|---|---|---|---|---|---|---|---|---|---|
| | 16 | 17 | 18 | 19 | 20 | 21 | 22 | 23 | 24 | 25 | 26 | 27 | 28 | 29 | 30 |
| M. suipneumoniae NB12 | 0.5 | 2.5 | 0.5 | 1.0 | 0.5 | 0.25 | 1.0 | 0.5 | 0.1 | 0.25 | 2.5 | 5.0 | NG | 10 | 5.0 |
| M. suipneumoniae JF 435 | 0.5 | 5.0 | 0.5 | 2.5 | 1.0 | 0.5 | 1.0 | 1.0 | 0.25 | 0.5 | 2.5 | 10 | 1.0 | >10 | 5.0 |
| M. suipneumoniae HK(2) | 0.5 | 10 | 1.0 | 2.5 | 1.0 | 0.5 | 1.0 | 1.0 | 0.25 | 1.0 | 5.0 | 10 | 0.5 | >10 | 2.5 |
| M. suipneumoniae Str. 11 | 0.25 | 2.5 | 0.25 | 1.0 | 0.5 | 0.25 | 0.5 | 0.5 | 0.1 | 0.5 | 2.5 | 5.0 | 0.25 | 10 | 2.5 |
| M. suipneumoniae J2206/183[b] | 0.5 | 5.0 | 1.0 | 5.0 | 1.0 | 0.5 | 1.0 | 1.0 | 0.25 | 1.0 | 5.0 | 10 | 0.5 | >10 | 2.5 |
| M. suipneumoniae MS 16 | 0.25 | 2.5 | 0.25 | 0.5 | 0.25 | 0.25 | 0.5 | 0.5 | 0.1 | 0.25 | 1.0 | 5.0 | 0.25 | 10 | 2.5 |
| M. suipneumoniae PW/C/210 | 0.25 | NG | 0.25 | 0.25 | 0.5 | 0.25 | 0.5 | 0.5 | 0.1 | 0.25 | 1.0 | 5.0 | NG | 10 | NG |
| M. suipneumoniae LABER | 0.25 | 2.5 | 0.25 | 1.0 | 0.5 | 0.25 | 0.5 | 0.5 | 0.1 | 0.25 | 2.5 | 5.0 | 0.25 | 10 | 2.5 |
| M. suipneumoniae UCD 1 | 0.5 | 5.0 | 0.5 | 2.5 | 1.0 | 0.25 | 1.0 | 1.0 | 0.25 | 1.0 | 2.5 | 10 | 0.25 | >10 | 2.5 |
| M. suipneumoniae TAM 6N | 0.5 | 10 | 1.0 | 2.5 | 1.0 | 0.5 | 1.0 | 1.0 | 0.25 | 1.0 | 5.0 | 10 | 0.5 | >10 | 5.0 |
| M. suipneumoniae ATCC 25095 | 0.25 | 5.0 | 0.5 | 1.0 | 0.5 | 0.25 | 1.0 | 0.5 | 0.1 | 0.5 | 2.5 | 5.0 | 0.25 | 10 | 2.5 |
| M. suipneumoniae NCTC 10110 | 0.5 | >10 | 1.0 | 5.0 | 1.0 | 0.5 | 1.0 | 1.0 | 0.25 | 1.0 | 5.0 | 10 | 0.5 | >10 | 2.5 |
| M. hyorhinis ATCC 23234 | 0.25 | 5.0 | 0.25 | 1.0 | 0.5 | 0.25 | 1.0 | 0.5 | 0.1 | 1.0 | 2.5 | 10 | 0.5 | >10 | 0.5 |
| M. hyorhinis ATCC 25021 | 0.25 | 5.0 | 0.5 | 1.0 | 0.5 | 0.25 | 0.5 | 0.5 | 0.1 | 0.5 | 2.5 | 5.0 | 0.5 | 10 | 0.5 |
| M. hyosynoviae ATCC 25591 | 0.5 | >10 | 0.5 | 0.5 | 0.5 | 0.1 | 1.0 | 1.0 | 0.25 | 1.0 | 0.5 | 2.5 | 1.0 | >10 | 1.0 |
| M. bovis NCTC 10131 | 0.05 | 2.5 | 0.05 | 0.025 | ≦0.01 | 0.025 | 0.05 | 0.025 | 0.025 | 0.025 | 0.025 | 0.05 | 0.05 | 0.5 | 0.25 |
| M. bovigenitalium ATCC 14173 | 0.1 | 5.0 | 0.1 | 0.1 | 0.05 | 0.05 | 0.1 | 0.1 | 0.1 | 0.25 | 0.25 | 0.25 | 0.1 | 1.0 | 0.25 |
| M. dispar NCTC 10125 | 0.1 | 2.5 | 0.25 | 0.5 | 0.25 | 0.1 | 0.5 | 0.5 | 0.1 | 0.25 | 1.0 | 2.5 | 0.1 | 2.5 | 0.25 |
| M. gallisepticum S6 | 2.5 | >10 | 1.0 | 10 | 2.5 | 0.25 | 5.0 | 1.0 | 0.5 | 2.5 | 2.5 | >10 | 2.5 | >10 | >10 |
| M. pneumoniae ATCC 15492 | 1.0 | >10 | 1.0 | 10 | 0.5 | 0.25 | 5.0 | 1.0 | 0.5 | 2.5 | 2.5 | 10 | 5.0 | >10 | 10 |

| Organism | Compound of Example No. | | | | | | |
|---|---|---|---|---|---|---|---|
| | 31 | 33 | 34 | 35 | 39 | 40 | 41 |
| M. suipneumoniae NB12 | 10 | 2.5 | 2.5 | NG | >10 | >10 | >10 |
| M. suipneumoniae JF 435 | 10 | 2.5 | 2.5 | >10 | >10 | >10 | >10 |
| M. suipneumoniae HK(2) | 10 | 2.5 | 2.5 | >10 | >10 | >10 | >10 |
| M. suipneumoniae Str. 11 | 5.0 | 1.0 | 1.0 | >10 | >10 | >10 | >10 |
| M. suipneumoniae J2206/183[b] | 10 | 1.0 | 2.5 | >10 | >10 | >10 | >10 |
| M. suipneumoniae MS 16 | 5.0 | 1.0 | 1.0 | >10 | >10 | >10 | >10 |
| M. suipneumoniae PW/C/210 | NG | NG | NG | NG | >10 | >10 | >10 |
| M. suipneumoniae LABER | 10 | 2.5 | 1.0 | >10 | >10 | >10 | >10 |
| M. suipneumoniae UCD 1 | 10 | 1.0 | 2.5 | >10 | >10 | >10 | >10 |
| M. suipneumoniae TAM 6N | 10 | 2.5 | 2.5 | >10 | >10 | >10 | >10 |
| M. suipneumoniae ATCC 25095 | 5.0 | 1.0 | 1.0 | >10 | >10 | >10 | >10 |
| M. suipneumoniae NCTC 10110 | 10 | 1.0 | 1.0 | >10 | >10 | >10 | >10 |
| M. hyorhinis ATCC 23234 | 5.0 | 1.0 | 2.5 | >10 | >10 | >10 | >10 |
| M. hyorhinis ATCC 25021 | 5.0 | 1.0 | 1.0 | >10 | >10 | >10 | >10 |
| M. hyosynoviae ATCC 25591 | 10 | 2.5 | 5.0 | >10 | >10 | >10 | >10 |
| M. bovis NCTC 10131 | 1.0 | 0.25 | 0.25 | 2.5 | 5.0 | 5.0 | 2.5 |

TABLE 1-continued

| | | | | | | | |
|---|---|---|---|---|---|---|---|
| M. bovigenitalium ATCC 14173 | 5.0 | 0.5 | 1.0 | 5.0 | 5.0 | 10 | 5.0 |
| M. dispar NCTC 10125 | 2.5 | 0.5 | 0.5 | >10 | >10 | >10 | >10 |
| M. gallisepticum S6 | >10 | >10 | >10 | >10 | >10 | >10 | >10 |
| M. pneumoniae ATCC 15492 | >10 | 10 | 5.0 | >10 | >10 | >10 | >10 |

*Only the Z-isomer was tested

TABLE 2

MIC's (μg/ml) against Veterinary Bacteria

| Organism | 1 | 2* | 3 | 4 | 5 | 6 |
|---|---|---|---|---|---|---|
| E. coli NCTC 10418 | >80 | >80 | >80 | >80 | >80 | >80 |
| E. coli E1 | >80 | >80 | >80 | >80 | >80 | >80 |
| S. dublin S7 | >80 | >80 | >80 | >80 | >80 | >80 |
| S. typhimurium S18 | >80 | >80 | >80 | >80 | >80 | >80 |
| Bord. bronchiseptica B08 | 80 | >80 | 40 | >80 | 80 | 80 |
| Bord. bronchiseptica B09 | 20 | >80 | 5.0 | 20 | 40 | 20 |
| Past. multocida PA1 | 10 | >80 | 5.0 | 5.0 | 5.0 | 10 |
| Past. multocida PA2 | 1.25 | 20 | 0.625 | 5.0 | 2.5 | 1.25 |
| Past. haemolytica PA5 | 80 | >80 | 10 | 40 | 40 | 80 |
| Erysipelothrix rhusiopathiae NCTC 8163 | 80 | >80 | >80 | >80 | 80 | >80 |
| Corynebacterium pyogenes CY1 | 80 | >80 | 80 | >80 | 80 | >80 |
| Staph. aureus B4 (pen. resistant) | 1.25 | 20 | 0.312 | 5.0 | 1.25 | 1.25 |
| Staph. aureus 152 (pen. sens) | 1.25 | 20 | 0.312 | 5.0 | 0.625 | 1.25 |
| Staph. aureus Oxford | 1.25 | 20 | 0.312 | 0.625 | 0.625 | 1.25 |
| Strep. suis (group D) SPS11 | 20 | >80 | 2.5 | 20 | 10 | 10 |
| Strep. uberis SPU1 | 0.625 | 5.0 | 0.039 | 0.312 | 0.07 | 0.07 |
| Strep. dysgalactiae SPD1 | 0.625 | 10 | 0.312 | 1.25 | 0.312 | 0.625 |
| Strep. agalactiae SPA1 | 1.25 | 20 | 1.25 | NG | 0.625 | 2.5 |
| B. subtilis ATCC 6633 | — | — | — | — | — | — |

| Organism | 7 | 9 | 10 | 11 | 12 |
|---|---|---|---|---|---|
| E. coli NCTC 10418 | >80 | >80 | >80 | >80 | >40 |
| E. coli E1 | >80 | >80 | >80 | >80 | >40 |
| S. dublin S7 | >80 | >80 | >80 | >80 | >40 |
| S. typhimurium S18 | >80 | >80 | >80 | >80 | >40 |
| Bord. bronchiseptica B08 | 40 | 40 | >80 | >80 | >40 |
| Bord. bronchiseptica B09 | 40 | 40 | 40 | 40 | 20 |
| Past. multocida PA1 | 40 | 20 | 5.0 | 5.0 | 2.5 |
| Past. multocida PA2 | 20 | 5.0 | 1.25 | 0.625 | 0.156 |
| Past. haemolytica PA5 | >80 | 40 | 40 | 40 | 40 |
| Erysipelothrix rhusiopathiae NCTC 8163 | >80 | 80 | >80 | >80 | >40 |
| Corynebacterium pyogenes CY1 | >80 | 80 | >80 | >80 | >40 |
| Staph. aureus B4 (pen. resistant) | 5.0 | 1.25 | 5.0 | 5.0 | 2.5 |
| Staph. aureus 152 (pen. sens) | 5.0 | 0.625 | 2.5 | 2.5 | 0.625 |
| Staph. aureus Oxford | 5.0 | 0.625 | 2.5 | 2.5 | 0.625 |
| Strep. suis (group D) SPS11 | 80 | 10 | 10 | 5.0 | 20 |
| Strep. uberis SPU1 | 1.25 | 0.16 | 0.625 | 0.312 | 0.625 |
| Strep. dysgalactiae SPD1 | 2.5 | 0.625 | 2.5 | 1.25 | 0.625 |
| Strep. agalactiae SPA1 | 5.0 | 10 | 2.5 | 2.5 | 20 |
| B. subtilis ATCC 6633 | — | — | — | — | — |

| Organism | 13 | 14 | 15 | 16 | 17 |
|---|---|---|---|---|---|
| E. coli NCTC 10418 | >80 | >80 | >80 | >80 | >80 |
| E. coli E1 | >80 | >80 | >80 | >80 | >80 |
| S. dublin S7 | >80 | >80 | >80 | >80 | >80 |
| S. typhimurium S18 | >80 | >80 | >80 | >80 | >80 |
| Bord. bronchiseptica B08 | >80 | >80 | 80 | >80 | >80 |
| Bord. bronchiseptica B09 | 20 | >80 | 20 | 40 | 40 |
| Past. multocida PA1 | 2.5 | 10 | 10 | 40 | 10 |
| Past. multocida PA2 | 0.312 | 10 | <0.039 | <0.039 | 1.25 |
| Past. haemolytica PA5 | 40 | >80 | 80 | >80 | >80 |
| Erysipelothrix rhusiopathiae NCTC 8163 | >80 | >80 | >80 | 80 | 80 |
| Corynebacterium pyogenes CY1 | >80 | >80 | >80 | >80 | >80 |
| Staph. aureus B4 (pen. resistant) | 1.25 | 10 | 2.5 | 5.0 | 10 |
| Staph. aureus 152 (pen. sens) | 1.25 | 10 | 0.625 | 1.25 | 10 |
| Staph. aureus Oxford | 1.25 | 10 | 1.25 | 1.25 | 20 |
| Strep. suis (group D) SPS11 | 10 | >80 | 20 | 20 | 40 |
| Strep. uberis SPU1 | 0.312 | 2.5 | 0.625 | 0.312 | 1.25 |

TABLE 2-continued

| | MIC's (μg/ml) against Veterinary Bacteria | | | | |
|---|---|---|---|---|---|
| Strep. dysgalactiae SPD1 | 0.625 | 2.5 | 1.25 | 1.25 | 2.5 |
| Strep. agalactiae SPA1 | 10 | >80 | 1.25 | 1.25 | 40 |
| B. subtilis ATCC 6633 | — | — | — | — | — |

| | Compound of Example No. | | | | |
|---|---|---|---|---|---|
| Organism | 18 | 19 | 20 | 21 | 22 |
| E. coli NCTC 10418 | >80 | >80 | >80 | >80 | >80 |
| E. coli E1 | >80 | >80 | >80 | >80 | >80 |
| S. dublin S7 | >80 | >80 | >80 | >80 | >80 |
| S. typhimurium S18 | >80 | >80 | >80 | >80 | >80 |
| Bord. bronchiseptica B08 | 40 | >80 | 80 | 40 | >80 |
| Bord. bronchiseptica B09 | 10 | 20 | 10 | 10 | 40 |
| Past. multocida PA1 | 10 | — | 2.5 | 2.5 | 20 |
| Past. multocida PA2 | 1.25 | NG | 0.312 | 0.625 | 10 |
| Past. haemolytica PA5 | 40 | >80 | 80 | 20 | 80 |
| Erysipelothrix rhusiopathiae NCTC 8163 | 40 | >80 | 80 | 40 | 80 |
| Corynebacterium pyogenes CY1 | >80 | >80 | >80 | >80 | >80 |
| Staph. aureus B4 (pen. resistant) | 0.156 | 1.25 | 0.63 | 1.25 | 1.25 |
| Staph. aureus 152 (pen. sens) | 0.312 | 1.25 | 0.63 | 0.625 | 1.25 |
| Staph. aureus Oxford | 0.625 | 2.5 | 2.55 | 2.5 | 2.5 |
| Strep. suis (group D) SPS11 | 10 | 80 | 40 | 10 | 20 |
| Strep. uberis SPU1 | <0.039 | 0.625 | 0.156 | 0.156 | 0.156 |
| Strep. dysgalactiae SPD1 | 0.156 | 2.5 | 0.625 | 0.625 | 1.25 |
| Strep. agalactiae SPA1 | 0.625 | 10 | 1.25 | 1.25 | 10 |
| B. subtilis ATCC 6633 | — | — | 10 | 2.5 | 0.625 |

| | Compound of Example No. | | | | |
|---|---|---|---|---|---|
| Organism | 23 | 24 | 25 | 26 | 27 |
| E. coli NCTC 10418 | >80 | >80 | >80 | >80 | >80 |
| E. coli E1 | >80 | >80 | >80 | >80 | >80 |
| S. dublin S7 | >80 | >80 | >80 | >80 | >80 |
| S. typhimurium S18 | >80 | >80 | >80 | >80 | >80 |
| Bord. bronchiseptica B08 | >80 | 80 | >80 | 80 | >80 |
| Bord. bronchiseptica B09 | 40 | 40 | 40 | 20 | 80 |
| Past. multocida PA1 | 5.0 | 5.0 | 5.0 | 10 | 20 |
| Past. multocida PA2 | 2.5 | 2.5 | 2.5 | 5.0 | 5.0 |
| Past. haemolytica PA5 | 80 | 40 | 80 | C | C |
| Erysipelothrix rhusiopathiae NCTC 8163 | >80 | 40 | >80 | >80 | >80 |
| Corynebacterium pyogenes CY1 | >80 | 80 | >80 | >80 | >80 |
| Staph. aureus B4 (pen. resistant) | 5.0 | 1.25 | 10 | 2.5 | 2.5 |
| Staph. aureus 152 (pen. sens) | 2.5 | 0.625 | 10 | 2.5 | 10 |
| Staph. aureus Oxford | 10 | 1.25 | 20 | 2.5 | 10 |
| Strep. suis (group D) SPS11 | 10 | 2.5 | 20 | 10 | >80 |
| Strep. uberis SPU1 | 0.625 | 0.312 | 0.625 | 0.156 | 1.25 |
| Strep. dysgalactiae SPD1 | 1.25 | 0.625 | 1.25 | 0.625 | 2.5 |
| Strep. agalactiae SPA1 | 2.5 | 1.25 | 2.5 | 2.5 | 20 |
| B. subtilis ATCC 6633 | 1.25 | 0.312 | 2.5 | 0.312 | 2.5 |

| | Compound of Example No. | | | | |
|---|---|---|---|---|---|
| Organism | 28 | 29 | 30 | 31 | 33 |
| E. coli NCTC 10418 | >80 | >80 | >80 | >80 | >80 |
| E. coli E1 | >80 | >80 | >80 | >80 | >80 |
| S. dublin S7 | >80 | >80 | >80 | >80 | >80 |
| S. typhimurium S18 | >80 | >80 | >80 | >80 | >80 |
| Bord. bronchiseptica B08 | 80 | >80 | >80 | >80 | >80 |
| Bord. bronchiseptica B09 | 20 | >80 | >80 | 80 | >80 |
| Past. multocida PA1 | 20 | >80 | 2.5 | — | 1.3 |
| Past. multocida PA2 | 2.5 | 80 | 0.312 | NG | 0.625 |
| Past. haemolytica PA5 | 80 | >80 | 10 | >80 | 20 |
| Erysipelothrix rhusiopathiae NCTC 8163 | 40 | >80 | >80 | >80 | >80 |
| Corynebacterium pyogenes CY1 | >80 | >80 | >80 | >80 | >80 |
| Staph. aureus B4 (pen. resistant) | 0.156 | 10 | 1.25 | 10 | 1.3 |
| Staph. aureus 152 (pen. sens) | 0.312 | 10 | 2.5 | 10 | 2.5 |
| Staph. aureus Oxford | 0.625 | 10 | 2.5 | 20 | 2.5 |
| Strep. suis (group D) SPS11 | 10 | >80 | >80 | >80 | >80 |
| Strep. uberis SPU1 | <0.039 | 5.0 | 10 | 40 | 5.0 |
| Strep. dysgalactiae SPD1 | 0.312 | 20 | 40 | >80 | 5.0 |
| Strep. agalactiae SPA1 | 1.25 | 40 | 40 | — | 10 |
| B. subtilis ATCC 6633 | 0.07 | — | — | — | — |

Compound of Example No.

TABLE 2-continued

MIC's (μg/ml) against Veterinary Bacteria

| Organism | 34 | 35 | 39 | 40 | 41 |
|---|---|---|---|---|---|
| E. coli NCTC 10418 | >80 | >80 | >80 | >80 | >80 |
| E. coli E1 | >80 | >80 | >80 | >80 | >80 |
| S. dublin S7 | >80 | >80 | >80 | >80 | >80 |
| S. typhimurium S18 | >80 | >80 | >80 | >80 | >80 |
| Bord. bronchiseptica B08 | >80 | >80 | >80 | >80 | >80 |
| Bord. bronchiseptica B09 | 40 | >80 | >80 | >80 | >80 |
| Past. multocida PA1 | — | 80 | 80 | 80 | 40 |
| Past. multocida PA2 | NG | NG | 40 | 80 | 20 |
| Past. haemolytica PA5 | >80 | >80 | 80 | >80 | >80 |
| Erysipelothrix rhusiopathiae NCTC 8163 | >80 | >80 | >80 | >80 | >80 |
| Corynebacterium pyogenes CY1 | >80 | >80 | >80 | 80 | 40 |
| Staph. aureus B4 (pen. resistant) | 2.5 | >80 | >80 | 80 | 40 |
| Staph. aureus 152 (pen. sens) | 2.5 | >80 | >80 | 80 | 40 |
| Staph. aureus Oxford | 5.0 | >80 | >80 | 80 | 40 |
| Strep. suis (group D) SPS11 | 80 | >80 | >80 | >80 | >80 |
| Strep. uberis SPU1 | 5.0 | 80 | >80 | 40 | 10 |
| Strep. dysgalactiae SPD1 | 10 | >80 | >80 | >80 | 20 |
| Strep. agalactiae SPA1 | 40 | >80 | NG | >80 | 40 |
| B. subtilis ATCC 6633 | — | >80 | — | — | — |

*Only the Z-isomer was tested

TABLE 3

MIC's (μg/ml) against Human Bacteria

| Organism | 1 | 2* | 3 | 4 | 5 | 9 | 10 |
|---|---|---|---|---|---|---|---|
| E. coli NCTC 10418 | >100 | >50 | >100 | >100 | >50 | >100 | >128 |
| E. coli ESS | 10 | 25 | 0.5 | 2.5 | 1.2 | 5.0 | 8.0 |
| P. mirabilis 889 | >100 | >50 | 50 | >100 | >50 | >100 | >128 |
| K. aerogenes A | >100 | >50 | 100 | >100 | >50 | >100 | >128 |
| Ps. aeruginosa NCTC 10662 | >100 | >50 | >100 | >100 | >50 | >100 | >128 |
| Pasteurella multocida 1633 | 10 | >50 | 0.5 | 25 | 5.0 | 5.0 | 8.0 |
| Haemophilus influenzae Q1 | 1.0 | 12.5 | 0.1 | 2.5 | 1.2 | 5.0 | 1.0 |
| Haemophilus influenzae Wy21 | 1.0 | 12.5 | 0.1 | 2.5 | 1.2 | 50 | 2.0 |
| Neisseria catarrhalis 1502 | 10 | >50 | 0.5 | 10 | 5.0 | 10 | 8.0 |
| Bacillus subtilis 6633 | 2.5 | 25 | 0.5 | 5.0 | 1.2 | 1.0 | 2.0 |
| Corynebacterium xerosis 9755 | >100 | >50 | >100 | >100 | >50 | >100 | >128 |
| Sarcina lutea 8340 | ≧100 | >50 | >100 | >100 | >50 | >100 | >128 |
| Staph. aureus Oxford | 5.0 | 25 | 0.2 | 2.5 | 1.2 | 2.5 | 8.0 |
| Staph. aureus Russell | 5.0 | >50 | 5.0 | 5.0 | 5.0 | 5.0 | 8.0 |
| Staph. aureus W2827 | 5.0 | >50 | 1.0 | 5.0 | 5.0 | 5.0 | 8.0 |
| Strep. faecalis I | ≧100 | >50 | 50 | >100 | 50 | >100 | >128 |
| Strep. pyogenes R80/421-A | 1.0 | >50 | 0.5 | 5.0 | — | 10 | 8.0 |
| Strep. agalactiae 2788-B | 5.0 | >50 | 0.5 | 5.0 | 2.5 | 10 | 8.0 |
| Strep. spp. 64/848-C | 2.5 | >50 | 0.5 | 5.0 | — | 5.0 | 4.0 |
| Strep. pneumoniae CN33 | 2.5 | >50 | 0.5 | 5.0 | 2.5 | 10 | 8.0 |

| Organism | 6 | 7 | 11 | 12 | 13 | 14 |
|---|---|---|---|---|---|---|
| E. coli NCTC 10418 | >128 | >100 | >128 | >16 | >128 | >128 |
| E. coli ESS | 16 | 0.5 | 128 | >16 | 2.0 | 32 |
| P. mirabilis 889 | >128 | >100 | >128 | >16 | >128 | >128 |
| K. aerogenes A | >128 | >100 | >128 | >16 | >128 | >128 |
| Ps. aeruginosa NCTC 10662 | >128 | >100 | >128 | >16 | >128 | >128 |
| Pasteurella multocida 1633 | 16 | 2.5 | 8.0 | 4.0 | 2.0 | 16 |
| Haemophilus influenzae Q1 | 2.0 | 0.5 | 2.0 | 1.0 | 0.5 | 2.0 |
| Haemophilus influenzae Wy21 | 2.0 | 1.0 | 4.0 | 2.0 | 1.0 | 2.0 |
| Neisseria catarrhalis 1502 | 4.0 | 5.0 | 8.0 | 16 | 4.0 | 16 |
| Bacillus subtilis 6633 | 2.0 | 2.5 | 4.0 | 4.0 | 1.0 | 4.0 |
| Corynebacterium xerosis 9755 | >128 | >100 | >128 | >16 | 64 | >128 |
| Sarcina lutea 8340 | >128 | >100 | >128 | >16 | 128 | >128 |
| Staph. aureus Oxford | 8.0 | 5.0 | 16 | 8.0 | 4.0 | 16 |
| Staph. aureus Russell | 16 | 25 | 16 | 8.0 | 4.0 | 16 |
| Staph. aureus W2827 | 16 | 25 | 16 | 8.0 | 4.0 | 16 |
| Strep. faecalis I | >128 | >100 | >128 | >16 | >128 | >128 |
| Strep. pyogenes R80/421-A | 4.0 | 25 | 4.0 | 16 | 4.0 | 32 |
| Strep. agalactiae 2788-B | 4.0 | 25 | 4.0 | 16 | 2.0 | 32 |
| Strep. spp. 64/848-C | — | 10 | 2.0 | 4.0 | 1.0 | — |
| Strep. pneumoniae CN33 | 4.0 | 25 | 4.0 | 16 | 4.0 | 32 |

| Organism | 15 | 16 | 17 | 18 | 19 | 20 |
|---|---|---|---|---|---|---|
| E. coli NCTC 10418 | >128 | >64 | >64 | >128 | >128 | >128 |
| E. coli ESS | 16 | 32 | 16 | 8.0 | 16 | 4.0 |

TABLE 3-continued

MIC's (μg/ml) against Human Bacteria

| Organism | | | | | | |
|---|---|---|---|---|---|---|
| *P. mirabilis* 889 | >128 | >64 | >64 | >128 | >128 | >128 |
| *K. aerogenes* A | >128 | >64 | >64 | >128 | >128 | >128 |
| *Ps. aeruginosa* NCTC 10662 | >128 | >64 | >64 | >128 | >128 | >128 |
| *Pasteurella multocida* 1633 | 32 | 16 | 8.0 | 16 | 32 | 4.0 |
| *Haemophilus influenzae* Q1 | 4.0 | 2.0 | NG | NG | C | C |
| *Haemophilus influenzae* Wy21 | 4.0 | 2.0 | 2.0 | 4.0 | 4.0 | 0.5 |
| *Neisseria catarrhalis* 1502 | 4.0 | 8.0 | 8.0 | 4.0 | C | C |
| *Bacillus subtilis* 6633 | 2.0 | 1.0 | 32 | 1.0 | 4.0 | 0.5 |
| *Corynebacterium xerosis* 9755 | >128 | >64 | >64 | >128 | 128 | >128 |
| *Sarcina lutea* 8340 | >128 | >64 | NG | NG | 128 | >128 |
| *Staph. aureus* Oxford | 2.0 | 4.0 | 32 | 2.0 | 4.0 | 4.0 |
| *Staph. aureus* Russell | 8.0 | 4.0 | >64 | 8.0 | 4.0 | 4.0 |
| *Staph. aureus* W2827 | 8.0 | 4.0 | >64 | 8.0 | 4.0 | 4.0 |
| *Strep. faecalis* I | >128 | >64 | >64 | >128 | >128 | >128 |
| *Strep. pyogenes* R80/421-A | 8.0 | 4.0 | 4.0 | 2.0 | 2.0 | 0.25 |
| *Strep. agalactiae* 2788-B | 8.0 | 4.0 | 32 | 8.0 | 16 | 2.0 |
| Strep. spp. 64/848-C | — | — | 32 | 4.0 | 16 | 2.0 |
| *Strep. pneumoniae* CN33 | 8.0 | 4.0 | 64 | 4.0 | NG | NG |

| | Compound of Example No. | | | | | |
|---|---|---|---|---|---|---|
| Organism | 21 | 22 | 23 | 24 | 25 | 26 |
| *E. coli* NCTC 10418 | >128 | >128 | >64 | >64 | >128 | >128 |
| *E. coli* ESS | 4.0 | 64 | 4.0 | 4.0 | 4.0 | 8.0 |
| *P. mirabilis* 889 | >128 | >128 | >64 | >64 | >128 | >128 |
| *K. aerogenes* A | >128 | >128 | >64 | >64 | >128 | >128 |
| *Ps. aeruginosa* NCTC 10662 | >128 | >128 | >64 | >64 | >128 | >128 |
| *Pasteurella multocida* 1633 | 8.0 | 32 | 2.0 | 16 | 16 | 16 |
| *Haemophilus influenzae* Q1 | C | C | C | C | C | C |
| *Haemophilus influenzae* Wy21 | 2.0 | 4.0 | 1.0 | 4.0 | 2.0 | 0.25 |
| *Neisseria catarrhalis* 1502 | C | C | C | C | C | C |
| *Bacillus subtilis* 6633 | 1.0 | 4.0 | 2.0 | 4.0 | 2.0 | 0.25 |
| *Corynebacterium xerosis* 9755 | >128 | >128 | >128 | >128 | 128 | >128 |
| *Sarcina lutea* 8340 | >128 | >128 | >128 | >128 | 128 | >128 |
| *Staph. aureus* Oxford | 4.0 | 4.0 | 4.0 | 4.0 | 4.0 | 4.0 |
| *Staph. aureus* Russell | 4.0 | 16 | 16 | 4.0 | 32 | 4.0 |
| *Staph. aureus* W2827 | 4.0 | 16 | 16 | 4.0 | 32 | 4.0 |
| *Strep. faecalis* I | >128 | >128 | >128 | >128 | >128 | >128 |
| *Strep. pyogenes* R80/421-A | 1.0 | 8.0 | 0.5 | 2.0 | 2.0 | 1.0 |
| *Strep. agalactiae* 2788-B | 4.0 | 16 | 2.0 | 2.0 | 2.0 | 2.0 |
| Strep. spp. 64/848-C | 4.0 | 16 | 2.0 | 4.0 | 4.0 | 2.0 |
| *Strep. pneumoniae* CN33 | NG | NG | NG | NG | NG | NG |

| | Compound of Example No. | | | | | |
|---|---|---|---|---|---|---|
| Organism | 27 | 29 | 30 | 31 | 33 | 34 |
| *E. coli* NCTC 10418 | >64 | >100 | >128 | >128 | >128 | >128 |
| *E. coli* ESS | 16 | >100 | 8.0 | 64 | 8.0 | 16 |
| *P. mirabilis* 889 | >64 | >100 | >128 | >128 | >128 | >128 |
| *K. aerogenes* A | >64 | >100 | >128 | >128 | >128 | >128 |
| *Ps. aeruginosa* NCTC 10662 | >64 | >100 | >128 | >128 | >128 | >128 |
| *Pasteurella multocida* 1633 | 32 | >100 | 8.0 | 64 | 2.0 | 64 |
| *Haemophilus influenzae* Q1 | C | 50 | NG | NG | NG | NG |
| *Haemophilus influenzae* Wy21 | 2.0 | 50 | <0.06 | 16 | 0.25 | 2.0 |
| *Neisseria catarrhalis* 1502 | C | 50 | 8.0 | 8.0 | 4.0 | 4.0 |
| *Bacillus subtilis* 6633 | 4.0 | 50 | 8.0 | 64 | 1.0 | 4.0 |
| *Corynebacterium xerosis* 9755 | >64 | >100 | >128 | >128 | >128 | >128 |
| *Sarcina lutea* 8340 | >64 | >100 | NG | NG | NG | NG |
| *Staph. aureus* Oxford | 8.0 | 25 | 8.0 | 64 | 8.0 | 8.0 |
| *Staph. aureus* Russell | 16 | 100 | 16 | 128 | 8.0 | 16 |
| *Staph. aureus* W2827 | 16 | 50 | 16 | 128 | 8.0 | 16 |
| *Strep. faecalis* I | >64 | >100 | >128 | >128 | >128 | >128 |
| *Strep. pyogenes* R80/421-A | 4.0 | 50 | 32 | 128 | 8.0 | 8.0 |
| *Strep. agalactiae* 2788-B | 16 | 50 | 128 | >128 | 64 | 64 |
| Strep. spp. 64/848-C | 16 | 25 | >128 | >128 | 32 | 64 |
| *Strep. pneumoniae* CN33 | NG | 50 | 128 | >128 | 32 | 64 |

| | Compound of Example No. | | | |
|---|---|---|---|---|
| Organism | 35 | 39 | 40 | 41 |
| *E. coli* NCTC 10418 | >128 | >100 | >100 | >100 |
| *E. coli* ESS | 128 | >100 | 100 | 50 |
| *P. mirabilis* 889 | >128 | >100 | >100 | >100 |
| *K. aerogenes* A | >128 | >100 | >100 | >100 |
| *Ps. aeruginosa* NCTC 10662 | >128 | >100 | >100 | >100 |
| *Pasteurella multocida* 1633 | >128 | 50 | 100 | 25 |
| *Haemophilus influenzae* Q1 | C | 5 | 50 | 10 |
| *Haemophilus influenzae* Wy21 | 128 | 2.5 | 50 | 25 |
| *Neisseria catarrhalis* 1502 | C | 25 | 50 | 25 |
| *Bacillus subtilis* 6633 | >128 | >100 | 100 | 100 |
| *Corynebacterium xerosis* 9755 | >128 | >100 | >100 | >100 |
| *Sarcina lutea* 8340 | >128 | >100 | >100 | >100 |
| *Staph. aureus* Oxford | >128 | 100 | 100 | 100 |

TABLE 3-continued

| | MIC's (μg/ml) against Human Bacteria | | | |
|---|---|---|---|---|
| Staph. aureus Russell | >128 | >100 | 100 | >100 |
| Staph. aureus W2827 | >128 | >100 | >100 | >100 |
| Strep. faecalis I | >128 | >100 | >100 | >100 |
| Strep. pyogenes R80/421-A | >128 | — | — | >100 |
| Strep. agalactiae 2788-B | >128 | >100 | >100 | >100 |
| Strep. spp. 64/848-C | >128 | — | — | 100 |
| Strep. pneumoniae CN33 | NG | 100 | >100 | >100 |

*Only the Z-isomer was tested

We claim:

1. A compound of the formula (II)

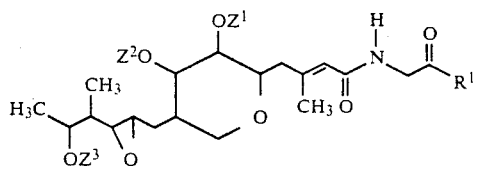

wherein $R^1$ is phenyl unsubstituted or substituted by halo, alkyl of 1 to 6 carbon atoms, alkoxy of 1 to 6 carbon atoms, hydroxy, carboxy, alkoxycarbonyl of 1 to 6 carbon atoms in the alkoxy moiety, carbamoyl, mono- or di-alkyl carbamoyl of 1 to 6 carbon atoms in each alkyl moiety, sulphamoyl, mono-or di-alkyl sulphamoyl, cyano, nitro, amino, mono- or di-alkylamino of 1 to 6 carbon atoms in each alkyl moiety, acylamino of 1 to 6 carbon atoms, ureido, alkoxycarbonylamino of 1 to 6 carbon atoms in the alkoxy moiety 2,2,2-trichloroethoxy carbonyl-amino, alkanoyl of 1 to 6 carbon atoms in the alkyl moiety, alkylthio of 1 to 6 carbon atoms, alkanesulphinyl of 1 to 6 carbon atoms or alkanesulphonyl of 1 to 6 carbon atoms; and $Z^1$, $Z^2$ and $Z^3$ are the same or different and each is hydrogen or a hydroxyl-protecting group.

2. The compound according to claim 1 which is phenacyl monamide A.

3. The compound according to claim 1 which is o-nitrophenacyl monamide A.

4. The compound according to claim 1 which is p-nitrophenacyl monamide A.

5. The compound according to claim 1 which is m-nitrophenacyl monamide A.

6. The compound according to claim 1 which is p-bromophenacyl monamide A.

7. The compound according to claim 1 which is o-cyanophenacyl monamide A.

8. The compound according to claim 1 which is m-(methylthio)phenacyl monamide A.

9. The compound according to claim 1 which is o-(methylthio)phenacyl monamide A.

10. The compound according to claim 1 which is p-hydroxymethylphenacyl monamide A.

* * * * *